(12) United States Patent
Wang et al.

(10) Patent No.: US 6,838,078 B2
(45) Date of Patent: Jan. 4, 2005

(54) FILM-FORMING COMPOSITIONS AND METHODS

(75) Inventors: Danli Wang, Shoreview, MN (US); Matthew T. Scholz, Woodbury, MN (US); Dong-Wei Zhu, Woodbury, MN (US); Triet M. Lu, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 33 days.

(21) Appl. No.: 10/052,158

(22) Filed: Jan. 16, 2002

(65) Prior Publication Data

US 2003/0194415 A1 Oct. 16, 2003

(51) Int. Cl.$^7$ ................... A61K 31/74; A61K 31/765; A61K 7/00; A01N 25/00; A01N 25/34
(52) U.S. Cl. .................. 424/78.02; 424/78.08; 424/78.18; 424/78.19; 424/400; 424/401; 424/404; 424/405
(58) Field of Search ............... 424/78.02, 78.08, 424/405, 400, 401, 404, 78.18, 78.19

(56) References Cited

U.S. PATENT DOCUMENTS

| | | |
|---|---|---|
| 3,216,983 A | 11/1965 | Shelanski et al. |
| 3,380,923 A | 4/1968 | Beach .................. 252/106 |
| 4,199,564 A | 4/1980 | Silver et al. |
| 4,358,567 A | 11/1982 | Hayama et al. .......... 525/359.4 |
| 4,542,012 A | 9/1985 | Dell |
| 4,584,192 A | 4/1986 | Dell et al. |
| 4,597,975 A | 7/1986 | Woodward et al. |
| 4,883,828 A | 11/1989 | Oakes et al. |
| 4,978,527 A | 12/1990 | Brink et al. |
| 5,013,763 A | 5/1991 | Tubesing et al. |
| 5,173,291 A | 12/1992 | Brink et al. |
| 5,235,015 A | 8/1993 | Ali et al. |
| 5,408,022 A | 4/1995 | Imazato et al. |
| 5,437,932 A | 8/1995 | Ali et al. |
| 5,529,770 A | 6/1996 | McKinzie et al. |
| 5,543,074 A | 8/1996 | Hague et al. |
| 5,618,841 A | 4/1997 | Kross |
| 5,621,058 A | 4/1997 | Kondo et al. |
| 5,665,776 A | 9/1997 | Yu et al. |
| 5,681,802 A | 10/1997 | Fujiwara et al. |
| 5,763,412 A | 6/1998 | Khan et al. |
| 5,800,685 A | 9/1998 | Perrault |
| 5,817,344 A | 10/1998 | Hoang et al. |
| 5,874,074 A | 2/1999 | Smith |
| 5,914,300 A | 6/1999 | Fujiwara et al. |
| 5,951,993 A | 9/1999 | Scholz et al. |
| 6,034,129 A | 3/2000 | Mandeville, III et al. |
| 6,039,940 A | 3/2000 | Perrault et al. |
| 6,086,911 A | 7/2000 | Godbey |
| 6,123,933 A | 9/2000 | Hayama et al. |
| 6,194,530 B1 | 2/2001 | Klesse et al. |
| 6,228,354 B1 | 5/2001 | Jeng |
| 6,251,967 B1 | 6/2001 | Perichaud et al. |

FOREIGN PATENT DOCUMENTS

| | | |
|---|---|---|
| GB | 2 344 997 A | 6/2000 |
| JP | 5-295317 | 11/1993 |
| JP | 8-89779 | 4/1996 |
| JP | 8-325538 A2 | 12/1996 |
| JP | 11-228609 | 8/1999 |
| JP | 2983449 B2 | 9/1999 |
| JP | 11-269448 | 10/1999 |
| SU | 15-65855 | 3/1988 |
| WO | WO 86/05391 A1 | 9/1986 |
| WO | WO 94/06297 | 3/1994 |
| WO | WO 96/20227 A1 | 7/1996 |
| WO | WO 01/28572 A1 | 4/2001 |

OTHER PUBLICATIONS

"Airvol Polyvinyl Alcohol" Product Bulletin, available as CELV0L polyvinyl alcohols, Celanese Ltd., Dallas, TX (undated).
ASTM E 1173–93, "Standard Test Method for Evaluation of a Pre–Operative Skin Preparation," *Annual Book of ASTM Standards*, vol. 11.05, Title page and pp. 381–383 (2001).
ASTM D 3278–96, "Standard Test Methods for Flash Point of Liquids by Small Scale Closed–Cup Apparatus," *Annual Book of ASTM Standards*, vol. 06.01, Title page and pp. 366–373 (2002).
Billmeyer, Jr. "Textbook of Polymer Science," 2$^{nd}$ Edition, Wiley–Interscience, Title page, Publication page, Table of Contents and pp. 84–89 (1971).
Block, *Disinfection, Sterilization, and Preservation*, 4$^{th}$ Edition, Lea & Febiger, Philadelphia, PA, Gottardi, "Chapter 8, Iodine and Iodine Compounds," Title page and pp. 152–166 (1991).
Butterfield, "The Selection of a Dilution Water for Bacteriological Examinations," *Journal of Bacteriology*, vol. 23, No. 355, Baltimore, MD, Title page and pp. 355–368 (1932).
Draize, "Dermal Toxicity," *Appraisal of the Safety of Chemicals in Foods, Drugs, and Cosmetics*, Association of Food and Drug Officials of the United States, Topeka, Kansas, Title page and pp. 46–59 (1959).
Providone–Iodine [online] United States Pharmacopeia monograph, USP–NF OnlineAug. 1, 2002–Dec. 31, 2002 [retrieved on Aug. 20, 2002]. Retrieved from the Internet: <URL: www.uspnf.com>.

Primary Examiner—Shelley A. Dodson
(74) Attorney, Agent, or Firm—Nancy M. Lambert

(57) ABSTRACT

Film-forming compositions, as well as methods of making and using, wherein the compositions include an optional active agent, water, a surfactant, and a water-soluble or water-dispersible vinyl polymer comprising amine group-containing side-chains and a copolymerized hydrophobic monomer; wherein the amine equivalent weight of the polymer is at least about 300 grams polymer per equivalent of amine group.

69 Claims, No Drawings ns and Methods

BACKGROUND

The present invention relates to film-forming compositions, particularly to compositions that include at least one active agent, preferably an antimicrobial agent such that the compositions are useful for tissue antisepsis, particularly skin antisepsis.

It is a standard practice in the industrialized world to disinfect the skin prior to any invasive procedure such as surgery, catheterization, or needle puncture in or to reduce the risk of infection. These products are often referred to as skin preps or simply "preps." It is particularly advantageous to customers to have a single product that can be used on both in-tact skin and mucosal tissue (e.g. vaginal, oral, nasal, and ocular tissue). Other sensitive tissues that antimicrobial products have been used on include acute and chronic wounds as well as burns. For all of these skin antiseptics it is desirable to achieve a very rapid microbial reduction so that the clinician can get on with the intended procedure.

Recently, there have been several alcohol-based antiseptics on the market for both presurgical and precatherization antisepsis. These products, while good rapid acting antiseptics due to the high alcohol content (e.g., typically at least about 60 wt-%), are only suitable for use on in-tact skin and are not suitable for use on sensitive tissues such as mucosal tissue, wounds, or burn tissue.

It is well known that none of the commercially available skin antiseptics kill all of the bacteria on the skin. For this reason, recent products have incorporated film-forming polymers that resist wash-off during surgery or exposure to fluids. Prior art attempts to improve the length of antiseptic activity through the use of film-forming polymers is described, for example, in U.S. Pat. Nos. 4,978,527 (Brink et al.) and 5,763,412 (Khan et al.). Many of these products also require an organic remover solution or lotion to get the prep off the skin. This is inconvenient for the clinician and requires significant extra time.

Thus, there is still a need for antiseptics having increased speed and/or length of bactericidal activity on skin in a product that is delivered out of an aqueous solution, that preferably dries to a coating with little or no tack, and that preferably allows adhesion of PSA-coated products. There is also a need for delivery vehicles for a wide variety of active agents.

SUMMARY

The present invention relates to film-forming compositions, preferably that include at least one active agent, which is preferably an antimicrobial agent. Such compositions are typically useful for topical administration of the active agent. Compositions that either have antimicrobial activity inherently or include an antimicrobial agent are intended primarily for tissue antisepsis, and more particularly, skin antisepsis. The compositions of the present invention may also find utility as delivery vehicles for active agents such as delivery of topical pharmaceuticals and cosmetic agents. Furthermore, the compositions of the present invention may be used to deliver systemically active agents through the skin or mucosal tissue.

The film-forming compositions of the present invention are particularly suitable for topical administration to skin and sensitive tissues. They typically include a water-soluble or water-dispersible vinyl polymer that includes amine group-containing side-chains and a copolymerized hydrophobic monomer, wherein the amine equivalent weight of the polymer is at least about 300 grams (g) polymer per equivalent of amine group (preferably in an amount of no greater than about 3000 grams polymer per equivalent of amine group, more preferably in an amount of no greater than about 1500 grams polymer per equivalent of amine group).

In one preferred embodiment, a film-forming composition of the present invention includes: a water-soluble or water-dispersible vinyl polymer that includes amine group-containing side-chains and a copolymerized hydrophobic monomer; wherein the amine equivalent weight of the polymer is at least about 300 grams polymer per equivalent of amine group; water; and a surfactant; wherein the composition possesses at least one of the following characteristics: the polymer is present in an amount greater than the surfactant; or a dry film of the composition is substantive.

Preferably, the composition includes an active agent. Preferably, the active agent is an antimicrobial agent, a pharmaceutical, or a cosmetic agent. If an antimicrobial agent, preferably the active agent is iodine or an iodophor such as povidone-iodine, chlorhexidine, chlorhexidine salts, fatty acid monoesters of glycerin and propylene glycol, chlorinated phenols, triclosan, octenidine, or mixtures thereof.

Preferably, the surfactant is a nonionic surfactant, preferably having an HLB of at least about 14 and more preferably no greater than about 19. In certain embodiments, the compositions also include a surfactant having an HLB of less than about 14 or greater than about 19. In other embodiments, the compositions also include an anionic or amphoteric surfactant, such as one selected from the group consisting of sulfates, sulfonates, phosphates, phosphonates, ammonium sulfonate, amphoterics, and mixtures thereof.

Preferably, the compositions include a hydroxycarboxylic acid buffer, which includes, for example, an alpha-hydroxycarboxylic acid such as lactic acid, malic acid, citric acid, or a mixture thereof.

Preferably, the vinyl polymer has a glass transition temperature of at least about 30° C., and more preferably at least about 50° C. In certain embodiments, the compositions further include a polymer having a higher Tg than that of the vinyl polymer having amine groups. Preferably, such a polymer is polyvinyl alcohol.

The present invention also provides a film-forming composition that includes: a water-soluble or water-dispersible vinyl polymer including amine group-containing side-chains and a hydrophobic monomer; wherein the amine equivalent weight of the polymer is about 300 grams to about 3000 grams polymer per equivalent of amine group (preferably, about 300 grams to about 1500 grams polymer per equivalent of amine group); an active agent; water; and a surfactant; wherein the composition possesses at least one of the following characteristics: the polymer is present in an amount greater than the surfactant; or a dry film of the composition is substantive. Preferably, the active agent is an antimicrobial agent.

Another film-forming composition of the present invention includes: a water-soluble or water-dispersible vinyl polymer prepared from monomers that include an amine group-containing monomer, about 1 wt-% to about 30 wt-% of a (C6–C22)alkyl (meth)acrylic monomer, and about 15 wt-% to about 75 wt-% of a (C1–C4)alkyl (meth)acrylic monomer; wherein the amine equivalent weight of the polymer is about 300 to about 3000 grams polymer per equivalent of amine group; water; and an active agent.

Preferred compositions of the present invention possesses two or more of the following characteristics: the polymer is present in an amount greater than the surfactant; the polymer to active agent weight ratio is at least about 0.25:1; or a dry film of the composition is substantive. More preferred compositions include all of these characteristics.

In certain embodiments, preferred vinyl polymers are prepared from dimethylamine oxide methacrylate, isobutyl methacrylate, methyl methacrylate, and a (C12–18)alkyl methacrylate. In certain other embodiments, preferred vinyl polymers are prepared from trimethylaminioethyl acrylate chloride, butyl acrylate, methyl methacrylate, and a (C12–18)alkyl methacrylate.

The present invention provides methods of disinfecting tissue. In one embodiment, the method includes applying a film-forming composition to tissue, and allowing the film-forming composition to remain on the tissue. In this embodiment, the film-forming composition includes: a water-soluble or water-dispersible vinyl polymer comprising amine group-containing side-chains and a copolymerized hydrophobic monomer; wherein the amine equivalent weight of the polymer is at least about 300 grams polymer per equivalent of amine group; water; and a surfactant; wherein the composition possesses at least one of the following characteristics: the polymer is present in an amount greater than the surfactant; or a dry film of the composition is substantive. Preferably, the composition further includes an antimicrobial agent.

The present invention also provides methods of delivering an active agent to tissue. In one embodiment, the method includes applying a film-forming composition to tissue, and allowing the film-forming composition to remain on the tissue. In this embodiment, the film-forming composition includes: a water-soluble or water-dispersible vinyl polymer comprising amine group-containing side-chains and a copolymerized hydrophobic monomer; wherein the amine equivalent weight of the polymer is at least about 300 grams polymer per equivalent of amine group; water; and an active agent.

Various other methods are provided that use the compositions of the present invention to deliver an active agent. These methods involve applying the composition to tissue and allowing it to remain on the tissue. Such methods are in contrast to the conventional way in which soaps and shampoos are used, which involves immediate dilution during use and thorough rinsing immediately after application. That is, the antiseptic compositions of the present invention are intended to remain on the tissue for a time sufficient to produce the desired effect (e.g., reduce the bacterial load on the tissue). This is possible due to the very low irritation potential of the compositions of the present invention.

The present invention also provides methods of making film-forming compositions. One such method involves combining components that include: a water-soluble or water-dispersible vinyl polymer comprising amine group-containing side-chains and a copolymerized hydrophobic monomer; wherein the amine equivalent weight of the polymer is at least about 300 grams polymer per equivalent of amine group; an active agent; water; and a surfactant. Preferably, the active agent is in a buffered solution and subsequently the vinyl polymer and surfactant are added to the buffered active agent.

Certain film-forming polymers of the present invention are also antimicrobial per se. Thus, the present invention provides a film-forming vinyl polymer having moieties derived from monoethylenically unsaturated monomers that include a quaternary ammonium group-containing monomer and a (C8–C22)alkyl (meth)acrylic monomer; wherein the polymer in an aqueous solution at a concentration of 1 wt-% exhibits at least a 50% reduction (preferably at least a 75% reduction) in antimicrobial activity against *Staphylococcus epidermidis* ATCC strain number 12228 in 30 minutes.

Herein, the following definitions are used:

"dry human skin site" refers to the back or abdomen of a person;

"film-forming" refers to a composition when allowed to dry under ambient conditions (e.g., 23° C. and 50% relative humidity (RH)) on in-tact skin forms a continuous layer that does not flake off after simple flexing of the tissue;

"hydroxycarboxylic acid" refers to free acids, as well as lactones thereof, salts thereof, or derivatives thereof as described in greater detail below;

"normal skin flora" refers to resident skin flora present on the skin of a healthy person and often consists of predominantly of *Staphylococcus epidermidis*;

"polymer" includes homopolymers and copolymers and "copolymer" includes a polymer of any length (including oligomers) of two or more types of polymerizable monomers, and therefore includes terpolymers, tetrapolymers, etc., which can include random copolymers, block copolymers, or sequential copolymers;

"side-chain" refers to the portion of a monomer which following polymerization forms a branch off the polymer backbone (i.e., main chain); in a vinyl polymer, it is a group of two or more atoms that branch off from the straight chain of carbon atoms formed by vinyl polymerization;

"stable" refers to an antiseptic composition that shows no signs of visible gross phase separation (precipitation, phase split, settling, etc.) after storage at 50° C. for 5 days (preferably 10 days, more preferably 20 days, and most preferably 30 days); certain samples may become slightly cloudy during storage at 50° C. for 5 days, however, since there is no gross precipitation and/or settling these samples are considered to be physically stable, but the most stable samples show no visible changes, i.e., no changes in clarity, color, etc.;

"substantially nontacky" refers to a dry film of about 4 milliggrams composition per square centimeter (mg/cm$^2$) of skin on a inner forearm that demonstrates little or no tack to a dry thumb (washed with a lotion-free soap such as IVORY bar soap (Proctor and Gamble, Cincinnati, Ohio) and dried thoroughly immediately prior to use) when pressed onto the dry film and immediately removed;

"substantive" as it applies to a composition (or a film-forming polymer) means that when a composition (or a film-forming polymer in solution) is applied to human skin as a uniform wet film in an amount of approximately 4 milligram per square centimeter (mg/cm$^2$) clean dry skin on an inner forearm and allowed to thoroughly dry (e.g., at least 10 minutes at 23° C. and 50% relative humidity), it resists removal under running tap water at a temperature of about 23° C. to about 24° C. and a flow rate of about 2.4–2.5 liters/minute (L/min) falling from a height of 15 centimeters (cm) and striking the skin immediately above the dry composition (not directly on the dry composition) and then flowing over the dry composition for at least about 15 seconds; and "wound" refers to an injury to mammalian tissue that involves breaking of a membrane such as the skin or mucosal surface usually with damage to underlying tissue arising from, but not limited to, a surgical incision, puncture, laceration, or burn.

DETAILED DESCRIPTION OF PREFERRED EMBODIMENTS

Desirable compositions, particularly antiseptic compositions, are aqueous-based and have the following characteristics: relatively high levels of bacterial kill if an antimicrobial agent is present (or the composition is inherently antimicrobial); relatively short dry times; generally clear viewing of the underlying tissue; good adhesion to the skin when dry; little or no tack when dry; capable of releasing an active agent such as an antimicrobial agent over a period of time; good adhesion of pressure sensitive adhesive (PSA) coated products such as incise drapes, tapes, wound dressings, and the like; resist lift off of PSA-coated products while under stress as typically occurs during retraction in surgery; allow adhesion of PSA-coated products for long periods of time, e.g., hours to days; suitable for use on sensitive tissues such as mucosal tissue; and can be removed relatively easily, preferably without the need for organic solvent-based removers.

Preferred compositions of the present invention possess all of the above-mentioned characteristics. Significantly, they provide rapid microbial kill (if the composition of the present invention is an antiseptic composition), and they dry to low tack or nontacky films, which allow good adhesion of PSA-coated products. Furthermore, they are gentle to tissue and can be removed with a water-soaked fabric, such as a towel or simple gauze.

Furthermore, preferred compositions of the present invention are very stable and can survive prolonged exposure to elevated temperatures, e.g., 50° C. and even as high as 60° C., for prolonged periods of time, e.g., for often greater than 7 days. The most stable samples show no visible changes at all such as changes in color, turbidity, and the like. Also, preferred compositions of the present invention are very stable upon exposure to low temperatures, e.g., 4° C., and even during repeated freeze/thaw cycles, e.g., 2 or more cycles.

Preferred compositions of the present invention are also generally substantive. More preferred compositions of the present invention are substantive while in moist environments, such as the vaginal vault and remain in the vagina for longer periods of time than typical antiseptics such as BETADINE 10% povidone-iodine solution (Purdue Frederick, Norwalk, Conn.). A "substantive" composition is one that when tested as described above resists removal for at least about 15 seconds. Preferably, the compositions are even more substantive and resist being removed under the same conditions for at least about 30 seconds, more preferably at least 45 seconds, and most preferably at least about 60 seconds. This is conveniently determined by imparting color to the composition (e.g., inclusion of a small amount of a dye or a colored active such as povidone-iodine in sufficient concentration that a relatively dark color results on the skin that can be easily seen as present or not).

The dried films of compositions of the present invention are generally flexible and durable. That is, they do not crack or flake off as brittle films might do. Significantly, the film-forming vinyl polymer contributes to achieving a delicate balance between low tack and flexibility.

Preferred compositions of the present invention also possess viscosities that ensure the formulations go on easily and form a relatively thin film that can dry rapidly. Preferably, the Brookfield viscosity (as described in the Examples Section) of a composition is no greater than about 1000 Centipoise (cps), more preferably no greater than about 500 cps, even more preferably no greater than about 250 cps, even more preferably no greater than about 100 cps, and most preferably no greater than about 50 cps, when measured at 23° C. using a Brookfield RVT ROTOVISCO viscometer and the procedure described in the Examples Section. This low viscosity ensures that the composition can be painted on the skin with little effort in a uniform thin film that will dry rapidly.

Dry times are preferably no greater than about 5 minutes, more preferably no greater than about 3 minutes, even more preferably no greater than about 2 minutes, and most preferably no greater than about 1.5 minutes on skin measured at 23° C. at 45–55% relative humidity. Dry time is measured as the minimum time for a composition applied with gauze in a uniform thin film of about 3 mg composition/cm$^2$ of skin to be visibly dry, demonstrate no transfer of the composition to a latex gloved covered hand, and have a minimum level of tack. An average of at least five subjects is typically used.

A particularly important property of the compositions of the present invention if an antimicrobial agent is included (or if the composition is inherently antimicrobial) is the ability to reduce the bacterial load on tissue, particularly skin, i.e., to kill the natural skin flora, rapidly. Preferably, antiseptic compositions of the present invention are capable of reducing normal skin flora by at least about 1 log (10-fold), more preferably by at least about 1.5 log, and most preferably by at least about 2 logs (100-fold), in 2 minutes on a dry human skin site (typically, skin on an abdomen or back) using ASTM testing method E1173-93 and a 30-second scrub with gauze soaked in the composition using moderate pressure.

Any number of antimicrobial agents may be used as described in more detail below. Preferred antimicrobial agents include iodine, iodophors, chlorhexidine salts such as chlorhexidine gluconate, and triclosan. The surprising rapid and high antimicrobial activity of the most preferred compositions is provided through the use of iodine or an iodophor as the active antimicrobial agent in combination with one or more hydroxycarboxylic acid buffers in particularly high use concentrations. The "use" concentration as used herein refers to the actual concentration of the composition that is applied to the tissue. Concentrates are contemplated.

The hydroxycarboxylic acid buffer in certain preferred compositions of the present invention contributes significantly to such good bacterial kill. By comparison, a composition of the present invention reduces normal skin flora by at least about 0.5 log more than the same composition without the hydroxycarboxylic acid present. This "same" composition includes additional water instead of the hydroxycarboxylic acid and would be adjusted to the same pH as the composition with the hydroxycarboxylic acid.

Generally, compositions are applied to the tissue, typically skin, and allowed to dry and remain in place for at least 2 minutes, and often for several hours to days. Significantly, many of the antiseptic compositions of the present invention maintain very low bacterial counts on the tissue, typically skin, for long periods of time, e.g., often up to 6 hours, and even up to 24 hours.

Film-Forming Polymers

One or more film-forming polymers are included in the compositions of the present invention to improve substantivity (e.g., resistance to wash off by blood and body fluid exposure), improve adhesion of PSA-coated products, and/ or reduce the tack of the compositions. Preferred film-forming polymers of the compositions of the present invention are substantive and resist removal by prolonged exposure to fluids such as water, saline, and body fluids, yet can be easily and gently removed without the need for organic solvents.

The film-forming polymers described herein are particularly unique for use in tissue antisepsis, particularly skin antisepsis. Previous attempts that used quaternary ammonium polymers, such as those described in U.S. Pat. No. 5,013,763 (Tubesing et al.) and 5,543,074 (Hague et al.), have failed since the quaternary ammonium vinyl polymers employed include all hydrophilic monomers in addition to the hydrophilic quaternary ammonium monomers. The compositions of the present invention incorporate film-forming polymers that have both hydrophilic and hydrophobic moieties. Preferably, the film-forming polymers are prepared from at least two monomers (i.e., a hydrophilic monomer and a hydrophobic monomer), and more preferably from at least three monomers.

More preferably, the film-forming polymer is a vinyl polymer that includes amine group-containing (i.e., amine-containing) side-chains and hydrophobic character. The term vinyl polymer refers to a polymer prepared from monoethylenically unsaturated monomers. The amine groups can be quaternary amine (i.e., quaternary ammonium) groups, amine oxide groups, and/or protonated tertiary amine groups.

With certain additives, such as iodine and iodophors, it is highly desirable to formulate a composition having a low pH, e.g., about 3 to about 5. Some conventional compositions attempt to use carboxylic acid functional polymers that may be protonated at these pH values and thus not ionized, however, these are not soluble. Unlike these materials, the polymers used in the compositions of the present invention rely upon amine groups which are permanently charged in the case of quaternary ammonium groups, protonated and thus cationic in the case of protonated tertiary amine groups, or nonionic and/or cationic in the case of amine oxide groups. For example, preferred amine oxide-containing polymers appear to be approximately 100% protonated and thus positively charged at a pH of about 4. The quaternary ammonium and amine oxide groups are believed to contribute to stability over a broad pH range, e.g., about 2 to about 12. The tertiary amine groups are believed to contribute to composition stability over a pH range of about 2 to about 9.

Preferred monoethylenically unsaturated amine group-containing monomers are monoethylenically unsaturated quaternary ammonium, amine oxide, and/or protonated tertiary amine group-containing monomers. Most preferred side-chain amine group-containing monomers are monoethylenically unsaturated quaternary amine, amine oxide, tertiary amine, or protonated tertiary amine group-containing (meth)acrylic monomers. The most preferred monoethylenically unsaturated amine group-containing monomers from which the film-forming polymers are formed are quaternary ammonium and amine oxide group-containing monomers. If desired, the tertiary amine group-containing monomers can be easily converted to protonated tertiary amine groups, amine oxide groups, or quaternary ammonium groups prior to or after polymerization by the appropriate chemical reaction as described herein. In the case of quaternary ammonium group-containing polymers, it is preferred that the polymer be prepared from the quaternary ammonium group-containing monomer. In the case of protonated tertiary amine group- and amine oxide group-containing polymers, it is preferred to first make the polymer from the corresponding tertiary amine and to subsequently covert the tertiary amine groups on the polymer to the protonated tertiary amine or amine oxide group.

For certain preferred film-forming polymers, the amine group-containing monomers used to prepare the film-forming polymers are typically used in an amount of at least about 15 wt-%, preferably at least about 20 wt-%, more preferably at least about 25 wt-%, and most preferably at least about 30 wt-%, based on the total weight of polymerizable composition (preferably, based on the total weight of the polymer). The amine group-containing monomers used to prepare the film-forming polymers are typically used in an amount of no greater than about 70 wt-%, preferably no greater than 65%, more preferably no greater than about 60 wt-%, and most preferably no greater than about 55 wt-%, based on the total weight of polymerizable composition (preferably, based on the total weight of the polymer).

The amine equivalent weight of the polymer is preferably at least about 300, more preferably at least about 350, even more preferably at least about 400, and most preferably at least about 500, grams polymer per equivalent of amine group. The amine equivalent weight of the polymer is preferably no greater than about 3000, more preferably no greater than about 1500, even more preferably no greater than about 1200, and most preferably no greater than about 950, grams polymer per equivalent of amine group.

Particularly preferred monoethylenically unsaturated amine group-containing monomers have the following general Formulae (I and II):

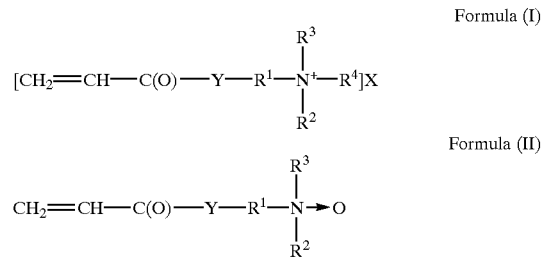

wherein: $R^1$ is a (C2–C8)alkylene group (saturated linear, branched, or cyclic alkylene group) optionally substituted with N, O, or S atoms; $R^2$ and $R^3$ are each independently a (C1–C8)alkyl group (saturated linear, branched, or cyclic alkyl group), a (C6–C12)aryl group, or a (C8–C15)aralkyl or alkaryl group (with saturated straight, branched, or cyclic alkyl groups), wherein optionally $R^2$ and/or $R^3$ can be joined together to form a heterocyclic ring system with the amine nitrogen, such as quarternary amines or amine oxides of alkyl morpholine, alkyl imidazole, alkyl piperazine, and the like; and $R^4$ is hydrogen, a (C1–C8)alkyl group (saturated linear, branched, or cyclic alkyl group), or a (C6–C12)aryl group, or a (C8–C15)aralkyl or alkaryl group (with saturated straight, branched, or cyclic alkyl groups); Y is O or $NR^5$ wherein $R^5$ is hydrogen or methyl; and X is a counterion and may be selected from any compatible counterion such as a halogen, (C1–C16)alkyl sulfate (preferably methyl or ethyl sulfate), (C1–C6)alkyl carboxylate, (C1–C16)alkyl phosphate, (C1–C16)alkyl sulfonate, or (C1–C16)alkyl phosphonate group present in the proper stoichiometry to ensure that the net charge on the molecule is neutral. The $R^4$ group preferably includes at least 1 carbon atom, on average. Preferably, $R^2$, $R^3$, and $R^4$ are each methyl.

Preferably, the monoethylenically unsaturated amine group-containing monomers of Formula I are acrylic monomers. The acrylic monomers are understood to include (meth)acrylate (i.e., acrylate or methacrylate) and/or (meth)acrylamide (i.e., acrylamide or methacrylamide) monomers. Preferred monomers include salts of trimethylaminoethylmethacrylate, trimethylaminoethylacrylate, trimethylaminopropyl acrylamide, trimethylaminopropyl methacrylamide, and protonated salts of dimethylaminoethylmethacrylate. Particularly preferred monomers are the chloride and methosulfate salts of trimethylaminoethylmethacrylate.

Preferably, the monoethylenically unsaturated amine group-containing monomers of Formula II are (meth)acrylate and/or (meth)acrylamide monomers. Preferred monomers include amine oxides of dimethylaminoethylmethacrylate, dimethylaminoethylacrylate, dimethylaminopropylacrylamide, and dimethylaminopropylmethacrylamide. Other amine oxide-containing monomers and polymers suitable are disclosed in U.S. Pat. No. 6,123,933 (Hayama et al.).

The amine group-containing monomers of the present invention are present in a concentration sufficient to ensure water solubility or water dispersibility and substantivity of the composition. As used herein the term "water-soluble" means that the polymer in the composition dissolves (perhaps after heating) in an amount of about 1% by weight or more in deionized water to form a transparent or translucent solution having a transmission of at least 70% in a 1 cm×1 cm cuvette measured at 650 nanometers (nm). The term "water-dispersible" means that the polymer in the composition is present as a fine particulate dispersion that is stable to storage at 50° C. for at least 30 days.

The amine-group containing monomer provides hydrophilic character to the polymer, However, other non-amine group-containing hydrophilic monomers may be used to prepare the film-forming polymer to assist in water solubility and/or stability. These include hydroxy-functional acrylates, polyethylene glycol-functional acrylates, vinyl-lactams such as N-vinylpyrrolidone and N-vinyl caprolactam, acrylamide, methacrylamide, hydrolyzed vinyl acetate (vinyl alcohol) and other monomers whose homopolymers result in water-soluble polymers. Note that vinyl-lactams and PEG-containing monomers are known to complex with iodine to form iodophors. This may or may not be advantageous for a particular composition.

In addition to an amine group-containing monomer, at least one hydrophobic monomer is used to prepare the film-forming polymers useful in the compositions of the present invention. The term "hydrophobic monomer" as used herein refers to a monomer which, if homopolymerized, would not be soluble in water at room temperature to more than about 0.25 wt-%. Preferably, such polymers have a molecular weight of about 8,000 Daltons to about 250,000 Daltons when examining for solubility.

In one embodiment, the invention provides a composition, particularly an antiseptic composition, that includes a vinyl polymer including amine group-containing side-chains as well as alkyl-Y-containing side-chains, wherein Y is O or $NR^6$. In these side-chains, $R^6$ is a H or $CH_3$ and wherein the alkyl group of the alkyl-Y-containing side-chain has 1 to 22 carbon atoms on average in a cyclic, branched-chain, or straight-chain configuration and optionally includes one or more heteroatoms, provided that a homopolymer of the alkyl-Y-containing side-chain monomer would be insoluble in water or a mixture of water and an active agent.

One preferred class of vinyl polymers used in the compositions of the present invention contains at least one copolymerized hydrophobic monoethylenically unsaturated alkyl (meth)acrylic monomer. As used herein, the "monoethylenically unsaturated" term in the alkyl (meth)acrylic monomer refers to the acrylic unsaturation. Preferably, "alkyl (meth)acrylic" monomers include (meth)acrylamides (e.g., octylacrylamide), (meth)acrylates, and combinations thereof. More preferably, the alkyl (meth)acrylic monomer is an alkyl (meth)acrylic acid ester (i.e., an alkyl acrylate or alkyl methacrylate), wherein the alkyl group has at least one carbon atom (on average). Preferably, the alkyl group has no greater than 50 carbon atoms, more preferably, no greater than 36 carbon atoms, and most preferably, no greater than 22 carbon atoms (on average). Alternatively stated, these alkyl (meth)acrylate monomers are (meth)acrylic acid esters of alkyl alcohols (preferably, non-tertiary alkyl alcohols), the alkyl groups of which preferably include 1 to 22 carbon atoms (on average). Of these, one preferred alkyl group includes 1 to 4 carbon atoms. Another preferred alkyl group includes 6 to 22 carbon atoms, more preferably 8 to 22 carbon atoms, and even more preferably 8 to 18 carbon atoms (on average). The alkyl group can optionally contain heteroatoms and can be linear, branched, or cyclic.

Preferred alkyl (meth)acrylate monomers have the following general Formula (III):

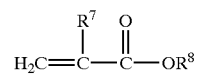

Formula (III)

wherein: $R^7$ is H or $CH_3$, the latter corresponding to where the (meth)acrylate monomer is a methacrylate monomer, and $R^8$ is broadly selected from linear, branched, or cyclic alkyl groups and optionally includes one or more heteroatoms (e.g., N, O, or S). The number of carbon atoms in the $R_8$ group is as outlined above for the alkyl group of the monoethylenically unsaturated alkyl (meth)acrylic monomer.

Examples of suitable alkyl (meth)acrylate monomers having shorter alkyl groups (C1–C4) useful in the present invention include, but are not limited to methyl acrylate, methyl methacrylate, ethyl acrylate, ethyl methacrylate, and n-propyl methacrylate, n-butyl acrylate, and isobutyl acrylate, isobutyl methacrylate, t-butyl methacrylate, and the like. Particularly preferred of these are methyl methacrylate and isobutyl methacrylate.

Examples of suitable alkyl (meth)acrylate monomers having longer alkyl groups (C6–C22) useful in the present invention include, but are not limited to cyclohexyl methacrylate, decyl acrylate, 2-ethylhexyl acrylate, n-hexyl acrylate, isoamyl acrylate, isodecyl acrylate, isononyl acrylate, isooctyl acrylate, lauryl acrylate, lauryl methacrylate, stearyl acrylate, stearyl methacrylate, behenyl methacrylate, 2-methylbutyl acrylate, 4-methyl-2-pentyl acrylate, ethoxy ethoxyethyl acrylate, isobornyl acrylate, mixtures thereof, and the like. Particularly preferred of these are isobutyl methacrylate, n-butyl acrylate, 2-ethylhexyl acrylate, isooctyl acrylate, lauryl methacrylate, stearyl methacrylate, and mixtures thereof.

Preferably the monoethylenically unsaturated alkyl (meth)acrylic monomer(s) can be used in an amount of at least about 35 weight percent, and more preferably at least about 45 wt-%, and most preferably at least 50% wt-%, based on the total weight of the polymerizable composition (and preferably, based on the total weight of the polymer). Preferably, the monoethylenically unsaturated alkyl (meth) acrylic monomer(s) can be used in an amount of no greater than about 85 wt-%, more preferably no greater than about 75 wt-%, and most preferably no greater than about 65 wt-%, based on the total weight of the polymerizable composition (and preferably, based on the total weight of the polymer).

Certain combinations of the amine group-containing monomers with long chain monomers are particularly useful in the present invention. The long chain alkyl monomers help to lower the glass transition temperature (Tg) of the polymer system and to improve substantivity of the polymer and composition. In general, this lower Tg helps to promote both adhesion to skin and especially adhesion of PSA-coated products over the composition. The long chain alkyl monomers (if homopolymerized) would form a polymer having a Tg of less than about 25° C. and preferably less than about 10° C.

Preferably, the vinyl polymers have a Tg of at least about 30° C., and more preferably at least about 50° C. One method of measuring the Tg of a polymer may involve the utilization of a Differential Scanning Calorimeter (DSC, e.g., the PYRIS 7-Series Thermal Analyzer, Perkin-Elmer, Shelton, CN) in the range of −100° C. to +100° C. at a rate of 20° C. per minute.

Polymers prepared from these amine group-containing monomers in combination with long chain monomers may be pressure sensitive adhesives such as those described in Applicants' Assignee's copending U.S. patent application Ser. No. 10/052,032, filed on even date herewith, entitled PRESSURE SENSITIVE ADHESIVES HAVING QUATERNARY AMMONIUM FUNCTIONALITY, ARTICLES, AND METHODS.

Other examples of film-forming substantive polymers that are PSAs at room temperature include those based on side-chain functional amine group monomers in combination with long chain alkyl acrylate polymers and optionally other hydrophilic monomers. For example, a particularly effective polymer that is a PSA includes 80% 2-ethylhexyl acrylate and 20% trimethylaminoethyl methacrylate chloride, based on the total weight of the polymerizable composition (and preferably, based on the total weight of the polymer). Another PSA polymer in this class includes 75% 2-ethylhexyl acrylate, 20% trimethylaminoethyl methacrylate chloride, and 5% of a methoxy polyethylene glycol (about 9 ethyleneoxy units) monoacrylate, which is commercially available from Shin-Nakamura Chemicals, Wakayama City, Japan under the trade designation AM-90G.

As stated previsouly, however, preferred compositions, have no or relatively low tack. Particularly preferred film-forming polymers of the present invention are formed from at least amine group-containing monomers, long chain (meth)acrylic monomers, and short chain (meth)acrylic monomers.

For these particularly preferred embodiments, the amine group-containing monomers are preferably present to provide a polymer with an amine equivalent weight of at least about 300, more preferably at least about 350, even more preferably at least about 400, and most preferably at least 500, grams polymer per equivalent of amine, wherein the amine group is selected from quaternary amine groups, amine oxide groups, tertiary amine groups, and combinations thereof. Preferably the amine equivalent weight of the polymer is no greater than about 4000, more preferably no greater than about 3000, even more preferably no greater than about 1500, even more preferably no greater than about 1200, and most preferably no greater than about 950, grams polymer per equivalent of amine group.

For these particularly preferred embodiments, the long chain (meth)acrylic monomer (e.g., a (C6–C22)alkyl (meth) acrylic monomer) is preferably used to prepare the polymer in an amount of at least about 1 wt-%, more preferably at least about 3-wt-%, and most preferably at least about 5 wt-%, based on the total weight of the polymerizable composition (and preferably, based on the total weight of the polymer). The long chain (meth)acrylic monomer is preferably used to prepare the polymer in an amount of no greater than about 40 wt-%, more preferably no greater than about 30 wt-%, even more preferably no greater than about 20 wt-%, and most preferably no greater than about 15 wt-%, based on the total weight of the polymerizable composition (and preferably, based on the total weight of the polymer). Most preferred polymers include about 5 wt-% to about 15 wt-% long chain (meth)acrylic monomer.

For these particularly preferred embodiments, the short chain (meth)acrylic monomer (e.g., a (C1–C4)alkyl (meth) acrylic monomer) is preferably used to prepare the polymer in an amount of at least about 15 wt-%, more preferably at least about 25 wt-%, and most preferably at least about 30 wt-%, based on the total weight of the polymerizable composition (and preferably, based on the total weight of the polymer). The short chain acrylic monomer is preferably used to prepare the polymer in an amount of no greater than about 75 wt-%, more preferably no greater than about 65 wt-%, and most preferably no greater than about 60 wt-%, based on the total weight of the polymerizable composition (and preferably, based on the total weight of the polymer). Most preferred polymers include about 30 wt-% to about 60 wt-% short chain (meth)acrylic monomer.

The most preferred film-forming polymers are formed from two different short chain acrylic monomers. The first is a (C1–C2)alkyl (meth)acrylic monomer such as methyl methacrylate and the second is a (C3–C4)alkyl (meth)acrylic monomer such as n-, t-, or iso-butyl acrylate. The very short chain monomer is present to increase the glass transition temperature to reduce the tack of the composition as well as provide some hydrophobicity. The (C3–C4)alkyl (meth) acrylic monomer is present to provide hydrophobicity as well as some flexibility to the film-forming polymer to ensure it does not easily flake off in use.

Certain of the film-forming vinyl polymers of the present invention are themselves antimicrobial (i.e., they are inherently antimicrobial). U.S. Pat. No. 5,408,022 (Imazato et al.) teaches that certan quatemary amine functional polyacrylates have antimicrobial activity. In general, these include quaternary amine groups containing at least one organic moiety having at least 6 contiguous carbon atoms. Surprisingly, it has been discovered that acrylic polymers based on short chain quaternary ammonium groups (all 4 organic substituents having less than 6 contiguous carbon atoms) can also have significant antimicrobial activity if copolymerized with monomers having alkyl groups having at least 8, and preferably at least 12 contiguous carbon atoms. Preferably, the alkyl groups have at most 22 carbon atoms, and more preferably at most 18 carbon atoms. For example, polyacrylate polymers based on trimethylaminoethyl methacrylate and 2-ethylhexyl acrylate show surprising antimicrobial activity. In addition, polyacrylate polymers based on trimethylaminoethyl methacrylate chloride salt and lauryl methacrylate appear to have even higher antimicrobial activity. In particular, polymers based on trimethylaminoethyl methacrylate chloride salt, lauryl methacrylate, and methyl methacrylate are particularly effective antimicrobial agents.

Preferably, the viscosity of a composition of the present invention is no greater than about 1000 cps when measured at 23° C. using a Brookfield RVT ROTOVISCO viscometer.

Therefore, the film-forming polymers of the present invention preferably have an inherent viscosity of no greater than about 0.75, and preferably no greater than about 0.5 when measured in tetrahydrofuran according to the method in the Examples Section. In order to ensure sufficient substantivity, however, the inherent viscosity of the film-forming polymer is preferably at least about 0.1, as measured in tetrahydrofuran according to the method in the Examples Section.

The molecular weight of the vinyl polymers is also preferably kept low in order to maintain a low viscosity composition. Preferably, the molecular weight of the vinyl polymers is generally no greater than about 350,000 Daltons, more preferably no greater than about 250,000 Daltons, even more preferably no greater than about 150,000 Daltons, and most preferably no greater than about 100,000 Daltons.

One or more substantive film-forming vinyl polymers are present in the compositions of the present invention in a total amount of at least about 2 wt-%, preferably at least about 3 wt-%, and more preferably at least about 5 wt-%, based on the total weight of composition. One or more substantive film-forming vinyl polymers are present in the composition in a total amount of no greater than about 10 wt-%, and more preferably no greater than about 8 wt-%, based on the total weight of composition.

Higher concentrations of the substantive film-forming vinyl polymer appear to promote adhesion of PSA-coated products. In certain compositions, however, higher concentrations may not be possible due to instability especially when exposed to temperatures above 50° C.

Preferably, the substantive film-forming vinyl polymer is present in an amount greater than the surfactant. More preferably the ratio of the substantive film-forming vinyl polymer to surfactant is at least about 1:1, more preferably at least about 1.3:1, and most preferably at least about 1.6:1.

Preferably, the weight ratio of the substantive film-forming polymer to the active agent weight ratio is greater than about 0.2:1, and more preferably within a range of about 0.25:1 to about 5:1, and most preferably in the range 0.5:1 to about 2:1.

Methods of Making Film-Forming Polymers

The film-forming polymers described above can be prepared by a wide variety of conventional free radical polymerization methods, including solution and emulsion polymerizations. Specific polymerization methods used in this invention are discussed in the Examples Section.

In one solution polymerization method, the alkyl (meth) acrylic monomer, amine group side-chain monomer (preferably, quaternary ammonium monomer or tertiary amine monomer), and optional other monomers (e.g. poly (alkylene oxide) monomer), along with a suitable thermal polymerization initiator, optional chain transfer agent, and solvent are charged into a glass vessel. The reaction vessel is then purged with nitrogen to create an inert atmosphere. Once purged, the solution within the vessel is heated to decompose the added thermal initiator, and the mixture is stirred during the course of the reaction. A conversion of about 98 percent to about 99 percent is typically obtained in about 20 hours. If desired, solvent can be removed and the polymer stored as a solid or dissolved/dispersed in an alternate solvent. For example, the polymer could be polymerized in ethanol, water added, and the ethanol removed by distillation. Suitable organic solvents, if required, may be any organic liquid that is inert to the reactants and product and will not otherwise adversely affect the reaction. Such solvents include methanol, ethanol, ethyl acetate, acetone, methyl ethyl ketones, and mixtures thereof. The amount of solvent is generally about 30 wt-% to about 80 wt-%, based on the total weight of the reactants and solvents.

For polymers containing an amine oxide side-chain group the polymer is preferably formed first using the corresponding tertiary amine monomer. Once the polymerization is complete the tertiary amine is oxidized to the amine oxide using a suitable oxidizing agent. The oxide forming reaction may be carried out at a temperature of about 20° C. to about 100° C. or higher for about 10 minutes to several days. A number of oxidizing agents may be employed including peroxides, ozone, and other oxidizing agents. For example, hydrogen peroxide, ammonium persulfate, peracetic acid, metachloroperbenzoic acid, benzoyl peroxide, t-butylhydroperoxide, and the like, are suitable. A preferred oxidizing agent is hydrogen peroxide since this may decompose without potentially toxic by-products.

It may be desirable to oxidize all or part of the tertiary amine. The oxidizing agents may be added at about 0.5 equivalent to about 3.0 equivalents of oxidizing agent per mole of tertiary amine. Preferably, greater than about 50%, more preferably greater than about 60%, even more preferably greater than about 70%, and most preferably greater than about 80%, of the tertiary amine is oxidized by using the oxidizing agent in excess. In general, when using hydrogen peroxide it has been have found that it is desirable to use about 0.6 to about 1.3 equivalents hydrogen peroxide/mole of tertiary amine. The hydrogen peroxide is added to the polymer solution and heated to about 60° C. to about 80° C. for about 3 hours to about 20 hours with stirring. In some applications the residual oxidizing agent may need to be removed. It may also be possible to form the amine oxide polymers of the present invention using monomers comprising amine oxide side-chain group containing monomers.

Active Agents

The compositions of the present invention are advantageously compatible (i.e., retain biological activity and emulsion stability) with at least one active agent, whether incorporated into the composition or contacted by the composition. Active agents typically include antimicrobials such as antibacterials, antivirals, antifungals, as well as corticosteroids such as hydrocortisone, and topical anesthetics. Various combinations of active agents can be used in the compositions of the present invention.

It may be desirable to add systemically active pharmaceutical agents to the compositions of the present invention to produce transdermal drug delivery vehicles, which are preferably substantive. When applied to the skin the pharmaceutical agent would be transported across the skin into the bloodstream. Exemplary pharmaceutical agents are disclosed in U.S. Pat. No. 6,086,911 (Godbey).

A preferred active agent is an antimicrobial. Although certain compositions of the present invention can have antimicrobial activity without any additional antimicrobial agents because of the incorporation of film-forming polymers that are inherently antimicrobial, additional antimicrobials can be added to the composition if desired.

Examples of antimicrobial agents include iodine and its complexed forms, which are commonly referred to as iodophors. Iodophors are complexes of elemental iodine or triiodide with certain carriers. These iodophors function to not only increase the iodine solubility but to reduce the level of free molecular iodine in solution and to provide a type of sustained release reservoir of iodine. Iodophors have been formed using carriers of polymers such as polyvinylpyrrolidone (PVP), copolymers of N-vinyl lactanis with other unsaturated monomers such as, but not limited to, acrylates and acrylamides, various polyether glycols (PEGs) including polyether-containing surfactants such as nonylphenolethoxylates and the like, polyvinyl alcohols, polycarboxylic acids such as polyacrylic acid, polyacrylamides, polysaccharides such as dextrose, and the like. Also reported in U.S. Pat. No. 4,597,975 (Woodward et al.) are protonated amine oxide surfactant-triiodide complexes that are also suitable iodophors for use in the present invention.

A preferred iodophor is povidone-iodine. This can be obtained commercially as povidone-iodine USP, which is a complex of K30 polyvinylpyrrolidone, iodine, and iodide wherein the available iodine is present at about 9 wt-% to about 12 wt-%.

Other antimicrobial agents may be included as long as they are compatible with the compositions. These include, but are not limited to, chlorhexidine salts such as chlorhexidine gluconate (CHG), parachlorometaxylenol (PCMX), triclosan, hexachlorophene, fatty acid monoesters of glycerin and propylene glycol such as glycerol monolaurate, glycerol monocaprylate, glycerol monocaprate, propylene glycol monolaurate, propylene glycol monocaprylate, propylene glycol moncaprate, phenols, surfactants and polymers that include a (C12–C22) hydrophobe and a quaternary ammonium group, polyquaternary amines such as polyhexamethylene biguanide, quaternary silanes, silver, silver salts such as silver chloride, silver oxide and silver sulfadiazine, methyl, ethyl, propyl and butyl parabens, octenidene, and the like, as well as combinations thereof. Various combinations of antimicrobial agents can be used in the compositions of the present invention.

Other active agents that may be delivered to the skin using a composition of the present invention include components of cosmetic compositions. These include, but are not limited to, emollients, humectants, conditioners, moisturizers, vitamins, herbal extracts, antioxidants, steroids or other anti-inflammatory agents, vasodilators, exfoliants such as α-hydroxy acids or β-hydroxy acids, growth factors, enzymes, bleaching or coloring agents, emulsifiers, artificial tanning agents, tanning accelerants, skin soothing agents, skin tightening agents, anti-wrinkle agents, skin repair agents, sebum inhibiting agents, sebum stimulators, protease inhibitors, anti-itch ingredients, agents for inhibiting hair growth, agents for accelerating hair growth, skin sensates, antiacne treatments, depilating agents, astringents, hair removers, or corn, callus or wart removers, decorative agents such as glitters, fragrances including aromatherapy agents, perfumes, sunscreen agents, insect repellants, deodorants and antiperspirants, hair colorants, bleaching agents, antidandruff agents. Various combinations of active agents can be used in the compositions of the present invention.

Preferably, one or more active agents are present in compositions of the present invention at a level of at least about 0.05 wt-%, and more preferably at least about 0.25 wt-%, based on the total weight of the composition. One or more active agents are preferably present at a level of no greater than about 10.0 wt-%, and more preferably, no greater than about 8.0 wt-%, based on the total weight of the composition.

For certain compositions that include iodophors, it is usually more convenient to describe the concentration in terms of the available iodine level. Preferably, whether from iodine or an iodophor or a combination thereof, the available iodine concentration is at least about 0.25 wt-%, and more preferably at least about 0.5 wt-%, based on the total weight of the composition. The available iodine is preferably present at not more than about 1.5 wt-%, and preferably not more than about 1 wt-%, based on the total weight of the composition.

The available iodine for most compositions may be determined by following the method in the United States Pharmacopeia Official Monographs for Povidone Iodine. Certain formulations may contain components that can interact with the method such as other anionic species. For this reason, the proper standards must be ran to ensure accuracy, and solvent systems or reagents may need to be changed to ensure accuracy. One skilled in the art would appreciate these considerations.

In order to ensure substantivity of water-soluble active agents, the weight ratio of film-forming polymer to active agent is preferably at least about 0.25:1, and more preferably at least about 0.5:1. Preferably, the weight ratio of film-forming polymer to active agent is no greater than about 5:1, and more preferably no greater than about 2:1.

Surfactants

It is particularly desirable when formulating with a film-forming polymer to include one or more surfactants to enhance solubility and stability of the polymer in the composition. In addition, surfactants help the compositions to wet the skin and ensure a smooth uniform coating. It is particularly important to provide a thin uniform coating that has complete coverage to ensure easy error-free application that will dry rapidly due to the thinness of the coating.

If used, one or more surfactants are generally added to the compositions of the present invention in an amount of at least about 0.5 wt-%, based on the total weight of the composition. Preferably, one or more surfactants are generally added to the compositions of the present invention in an amount of no greater than about 10 wt-%, more preferably no greater than about 7 wt-%, even more preferably no greater than about 5 wt-%, and most preferably no greater than about 3 wt-%, based on the total weight of the composition. Too little surfactant results in an unstable composition especially upon exposure to elevated temperatures. Too much surfactant can undermine the substantivity of the dried composition on skin. For this reason, the surfactant level is generally chosen as slightly above the minimum level of total surfactant required to ensure stability at 50° C.

Furthermore, it is preferred to use surfactants having low inorganic salt impurities such as sodium chloride, sodium sulfate, etc. Preferably, such salt content should be sufficiently low such that a 20% solution of the surfactant in water has a conductivity of less than about 100 micromhos/cm, more preferably less than about 85 micromhos/cm, and most preferably less than about 75 micromhos/cm.

The following types of surfactants can be used if desired:

a. Nonionic Surfactants. Particularly useful surfactants are nonionic surfactants. It has been found that polyalkoxylated, and in particular polyethoxylated, nonionic surfactants can stabilize the film-forming polymers of the present invention in aqueous solutions particularly well. In general, useful polyalkoxylated nonionic surfactants preferably have a hydrophile/lipophile balance (HLB) of at least about 14, and more preferably at least about 16. Useful polyalkoxylated nonionic surfactants preferably have an HLB of no greater than about 19. When using combinations of nonionic surfactants a weight average HLB is used to determine the HLB of the nonionic surfactant system. As used herein, the HLB is defined as one-fifth the weight percentage of ethylene oxide segments in the surfactant molecule.

Surfactants of the nonionic type that have been particularly useful include:

1. Polyethylene oxide extended sorbitan monoalkylates (i.e., Polysorbates). In particular, a Polysorbate 20 commercially available as NIKKOL TL-10 (from Barret Products) is very effective.

2. Polyalkoxylated alkanols. Surfactants such as those commercially available under the trade designation BRIJ from ICI Specialty Chemicals, Wilmington, Del. having an HLB of at least about 14 have proven useful. In particular, BRIJ 78 and BRIJ 700, which are stearyl alcohol ethoxylates having 20 and 100 moles of polyethylene oxide, respectively, have proven very useful. Also useful is a ceteareth 55, which is commercially available under the trade designation PLURAFAC A-39 from BASF Corp., Performance Chemicals Div., Mt. Olive, N.J.

3. Polyalkoxylated alkylphenols. Useful surfactants of this type include polyethoxylated octyl or nonyl phenols having HLB values of at least about 14, which are commercially available under the trade designations ICONOL and TRITON, from BASF Corp., Performance Chemicals Div., Mt. Olive, N.J. and Union Carbide Corp., Danbury, Conn., respectively. Examples include TRITON X100 (an octyl phenol having 15 moles of ethylene oxide available from Union Carbide Corp., Danbury, Conn.) and ICONOL NP70 and NP40 (nonyl phenol having 40 and 70 moles of ethylene oxide units, respectively, available from BASF Corp., Performance Chemicals Div., Mt. Olive, N.J.). Sulfated and phosphated derivatives of these surfactants are also useful. Examples of such derivatives include ammonium nonoxynol-4-sulfate, which is commercially available under the trade designation RHODAPEX CO-436 from Rhodia, Dayton, N.J.

4. Polaxamers. Surfactants based on block copolymers of ethylene oxide (EO) and propylene oxide (PO) have been shown to be effective at stabilizing the film-forming polymers of the present invention and provide good wetting. Both EO-PO-EO blocks and PO-EO-PO blocks are expected to work well as long as the HLB is at least about 14, and preferably at least about 16. Such surfactants are commercially available under the trade designations PLURONIC and TETRONIC from BASF Corp., Performance Chemicals Div., Mt. Olive, N.J. It is noted that the PLURONIC surfactants from BASF have reported HLB values that are calculated differently than described above. In such situation, the HLB values reported by BASF should be used. For example, preferred PLURONIC surfactants are L-64 and F-127, which have HLBs of 15 and 22, respectively. Although the PLURONIC surfactants are quite effective at stabilizing the compositions of the present invention and are quite effective with iodine as the active agent, they may reduce the antimicrobial activity of compositions using povidone-iodine as the active agent.

5. Polyalkoxylated esters. Polyalkoxylated glycols such as ethylene glycol, propylene glycol, glycerol, and the like may be partially or completely esterified, i.e., one or more alcohols may be esterified, with a (C8–C22)alkyl carboxylic acid. Such polyethoxylated esters having an HLB of at least about 14, and preferably at least about 16, are suitable for use in compositions of the present invention.

6. Alkyl Polyglucosides. Alkyl polyglucosides, such as those described in U.S. Pat. No. 5,951,993 (Scholz et al.), starting at column 9, line 44, are compatible with the film-forming polymers of the present invention and may contribute to polymer stability. Examples include glucopon 425, which has a (C8–C16)alkyl chain length with an average chain length of 10.3 carbons and 1–4 glucose units.

b. Amphoteric Surfactants. Surfactants of the amphoteric type include surfactants having tertiary amine groups which may be protonated as well as quaternary amine containing zwitterionic surfactants. Those that have been particularly useful include:

1. Ammonium Carboxylate Amphoterics. This class of surfactants can be represented by the following formula:

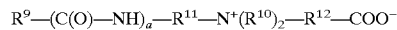

wherein: a=0 or 1; $R^9$ is a (C7–C21)alkyl group (saturated straight, branched, or cyclic group), a (C6–C22)aryl group, or a (C6–C22)aralkyl or alkaryl group (saturated straight, branched, or cyclic alkyl group), wherein $R^9$ may be optionally substituted with one or more N, O, or S atoms, or one or more hydroxyl, carboxyl, amide, or amine groups; $R^{10}$ is H or a (C1–C8)alkyl group (saturated straight, branched, or cyclic group), wherein $R^{10}$ may be optionally substituted with one or more N, O, or S atoms, or one or more hydroxyl, carboxyl, amine groups, a (C6–C9)aryl group, or a (C6–C9) aralkyl or alkaryl group; and $R^{11}$ and $R^{12}$ are each independently a (C1–C10)alkylene group that may be the same or different and may be optionally substituted with one or more N, O, or S atoms, or one or more hydroxyl or amine groups.

More preferably, in the formula above, $R^9$ is a (C1–C16) alkyl group, $R^{10}$ is a (C1–C2)alkyl group preferably substituted with a methyl or benzyl group and most preferably with a methyl group. When $R^{10}$ is H it is understood that the surfactant at higher pH values could exist as a tertiary amine with a cationic counterion such as Na, K, Li, or a quaternary amine group.

Examples of such amphoteric surfactants include, but are not limited to: certain betaines such as cocobetaine and cocamidopropyl betaine (commercially available under the trade designations MACKAM CB-35 and MACKAM L from McIntyre Group Ltd., University Park, Ill.); monoacetates such as sodium lauroamphoacetate; diacetates such as disodium lauroamphoacetate; amino- and alkylaminopropionates such as lauraminopropionic acid (commercially available under the trade designations MACKAM 1L, MACKAM 2L, and MACKAM 151L, respectively, from McIntyre Group Ltd.).

2. Ammonium Sulfonate Amphoterics. This class of amphoteric surfactants are often referred to as "sultaines" or "sulfobetaines" and can be represented by the following formula

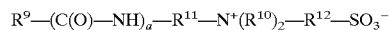

wherein $R^9$–$R^{12}$ and "a" are defined above. Examples include cocamidopropylhydroxysultaine (commercially available as MACKAM 50-SB from McIntyre Group Ltd.).

c. Anionic Surfactants. Surfactants of the anionic type that have been particularly useful include:

1. Sulfonates and Sulfates. Suitable anionic surfactants include sulfonates and sulfates such as alkyl sulfates, alkylether sulfates, alkyl sulfonates, alkylether sulfonates, alkylbenzene sufonates, alkylbenzene ether sulfates, alkylsulfoacetates, secondary alkane sulfonates, secondary alkylsulfates and the like. Many of these can be represented by the formulas:

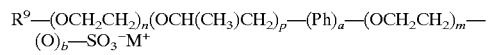

and

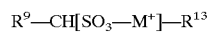

wherein: a and b=0 or 1; n, p, m=0–100 (preferably 0–40, and more preferably 0–20); $R^9$ is defined as above; $R^{13}$ is a (C1–C12)alkyl group (saturated straight, branched, or cyclic group) that may be optionally substituted by N, O, or S atoms or hydroxyl, carboxyl, amide, or amine groups;

PH=phenyl; and M is a cationic counterion such as Na, K, Li, ammonium, a protonated tertiary amine such as triethanolamine or a quaternary ammonium group.

In the formula above, the ethylene oxide groups (i.e., the "n" and "m" groups) and propylene oxide groups (i.e., the "p" groups) can occur in reverse order as well as in a random, sequential, or block arrangement. Preferably, for this class, $R^9$ includes an alkylamide group such as $R^{14}$—C(O)N(CH$_3$)CH$_2$CH$_2$— as well as ester groups such as —OC(O)—CH$_2$—wherein $R^{14}$ is a (C8–C22)alkyl group (saturated branched, straight, or cyclic group).

Examples include, but are not limited to: alkyl ether sulfonates such as lauryl ether sulfates such as Polystep B12 (n=3–4, M=sodium) and B22 (n=12, M=ammonium) available from Stepan Company, Northfield, Ill. and sodium methyl taurate (available under the trade designation NIKKOL CMT30 from Nikko Chemicals Co., Tokyo, Japan); secondary alkane sulfonates such as Hostapur SAS which is a Sodium (C14–C17)secondary alkane sulfonates (alpha-olefin sulfonates) available from Clariant Corp., Charlotte, N.C.; methyl-2-sulfoalkyl esters such as sodium methyl-2-sulfo(C12–16)ester and disodium 2-sulfo(C12–C16)fatty acid available from Stepan Company under the trade designation ALPHASTE PC-48; alkylsulfoacetates and alkylsulfosuccinates available as sodium laurylsulfoacetate (under the trade designation LANTHANOL LAL) and disodiumlaurethsulfosuccinate (STEPANMILD SL3), both from Stepan Company; alkylsulfates such as ammoniumlauryl sulfate commercially available under the trade designation STEPANOL AM from Stepan Company.

2. Phosphates. Suitable anionic surfactants also include phosphates such as alkyl phosphates, alkylether phosphates, aralkylphosphates, and aralkylether phosphates. Many may be represented by the formula:

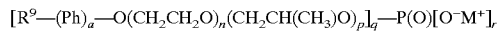

$[R^9—(Ph)_a—O(CH_2CH_2O)_n(CH_2CH(CH_3)O)_p]_q—P(O)[O^-M^+]_r$ wherein: PH, $R^9$, a, n, p, and M are defined above; r is 0–2; and q=1–3; with the proviso that when q=1, r=2, and when q=2, r=1, and when q=3, r=0. As above, the ethylene oxide groups (i.e., the "n" groups) and propylene oxide groups (i.e., the "p" groups) can occur in reverse order as well as in a random, sequential, or block arrangement.

Examples include a mixture of mono-, di- and tri-(alkyltetraglycolether)-o-phosphoric acid esters generally referred to as trilaureth-4-phosphate commercially available under the trade designation HOSTAPHAT 340KL from Clariant Corp., as well as PPG-5 ceteth 10 phosphate available under the trade designation CRODAPHOS SG from Croda Inc., Parsipanny, N.J.

3. Amine Oxides. Suitable anionic surfactants also include amine oxides including alkyl and alkylamidoalkyldialkylamine oxides of the following formula:

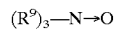

$(R^9)_3—N \rightarrow O$ wherein $R^9$ is defined above and each $R^9$ may be the same or different.

Optionally, the $R^9$ groups can be joined to form a heterocyclic ring with the nitrogen to form surfactants such as amine oxides of alkyl morpholine, alkyl piperazine, and the like. Preferably two $R^9$ groups are methyl and one $R^9$ group is a (C12–C16)alkyl or alkylamidopropyl group.

Examples of amine oxide surfactants include those commercially available under the trade designations AMMONYX LO, LMDO, and CO, which are lauryldimethylamine oxide, laurylamidopropyldimethylamine oxide, and cetyl amine oxide, all from Stepan Company.

Combinations of various surfactants can be used if desired. For example, nonionic surfactants in combination with certain anionic surfactants described above can be used for certain advantage. For example, one preferred surfactant system is based on a combination of a polysorbate and a polyethoxylated alkyl alcohol (Polysorbate 20+steareth-100).

Certain preferred anionic surfactants include a polyalkoxylate group. These include the sulfonates, sulfates, phosphates, and phosphonates.

For certain embodiments, it is desirable to select one or more surfactants that associate or potentially associate with other components in the composition after dry down may be tolerated better. For example, certain anionic surfactants such as methyl-2-sulfoalkyl esters (e.g., sodium methyl-2-sulfo(C12–16) ester and disodium 2-sulfo(C12–C16)fatty acid available from Stepan Company under the trade designation ALPHASTEP PC-48) in combination with polyamine oxide film-forming polymers appear to increase the substantivity of a dried film of the composition and adhesion of PSA-coated products. Certain of the sulfate and sulfonate containing surfactants also appear to significantly reduce dry times. The mechanism for this is not clear. While not intending to be bound by theory these surfactants may associate with cationic amine groups on film-forming polymers forming a more hydrophobic complex during dry down. Sulfates and sulfonates, phosphates and phosphonates, as well as the sulfobetaine type surfactants have been shown to reduce the dry time significantly.

Vehicle

Suitable liquid vehicles for the compositions of the present invention include water, optionally in combination with acetone or an alcohol, particularly a (C1–C4)alcohol (i.e., a lower alcohol) such as ethanol, 2-propanol, and n-propanol, and mixtures thereof. The preferred vehicle is injectable-grade water, i.e., USP grade "water for injection", however, other forms of purified water may be suitable such as distilled and deionized water.

For applications to in-tact skin, however, it may be desirable to include a lower alcohol such as ethanol, isopropanol, or n-propanol. These alcohols are well known to contribute to rapid microbial kill. For these applications the alcohol to water ratio is preferably at least about 60:40, and more preferably at least about 70:30, by weight. Addition of alcohol in these high concentrations will also decrease the dry time of the composition.

When a lower alcohol is used, incorporation of surfactants (as discussed in greater detail below) may or may not be necessary. In some cases elimination of the surfactant may allow for better adhesion of PSA-coated products over the dried film.

Particularly preferred compositions include water and are substantially free (i.e., less than about 10 wt-%) of volatile organic solvents (i.e., those having a closed-cap flash point of greater than about 140° F. (60° C.)), such as acetone, lower alcohols, alkanes, volatile silicones, etc.

Aqueous formulations are preferred since these formulations are gentle to both skin and mucosal tissue and may even be suitable for use on open wounds as a wound cleanser. Furthermore, compositions containing organic solvents may also be flammable, which is typically a consideration in shipping and handling the product.

Preferred compositions of the present invention include less than about 5 wt-% volatile organic solvents, and more preferably less than about 3 wt-% volatile organic solvents, based on the total weight of the composition. These preferred aqueous compositions typically are nonflammable, having a closed-cup flash point of greater than about 140° F. (60° C.). The addition of lower alcohols (C1–C4) at less than about 4 wt-% may improve wetting of the compositions and yet maintain a flashpoint above about 140° F. (60° C.). Flashpoint is measured according to test method ASTM D3278-96.

Optional Hydroxycarboxylic Acid Buffers

The compositions of the present invention are preferably buffered to prevent pH drift during storage. For example, it is well known that for iodine-containing systems it is important to maintain the pH at about 2 to about 6, and preferably at about 3 to about 5. As the pH is raised above about 6, the iodine can be rapidly converted to iodide, thus inactivating the antimicrobial effectiveness. Much below about a pH of about 2 and the composition may become irritating. In the compositions of the present invention, the pH is preferably adjusted to about 3.0 to about 4.5, and more preferably to about 3.5 to about 4.2.

While conventional compositions have included a buffer concentration of about 0.1 wt-% to about 2 wt-%, preferred compositions of the present invention can include certain hydroxycarboxylic acid buffers that can be used in much higher buffer concentrations. Preferably, the hydroxycarboxylic acid buffer is present in an amount of at least about 5 wt-%, and more preferably at least about 6 wt-%, based on the total weight of the composition.

Surprisingly, these compositions (i.e., with a pH preferably adjusted to about 3.0 to about 4.5, and more preferably to about 3.5 to about 4.2, and a relatively high hydroxycarboxylic acid buffer concentration—at least about 5 wt-%, and more preferably at least about 6 wt-%) are substantially nonirritating to tissue (e.g., skin and mucosal tissue), as indicated by studies conducted by instilling aliquots (of use concentrations) into rabbit eyes. This is illustrated in the examples, which indicates that compositions of the present invention when tested according to the Rabbit Eye Irritation Test produce very little, if any, corneal opacity, with substantially complete return to normal (i.e., clear or having a Draize score of zero) in no greater than about 96 hours, and preferably no greater than about 72 hours. This indicates that the compositions would be very gentle for use on skin and mucosal tissue. This is very surprising since previous reports have indicated that high levels of alpha-hydroxy acids at an acidic pH can be irritating to the skin.

This level of buffer is particularly desirable for antiseptic compositions that include povidone-iodine (particularly povidone-iodine USP) as the antimicrobial agent. In these systems the level of rapid microbial kill increases significantly and for some systems in a linear fashion with the molar concentration of the hydroxycarboxylic acid.

Suitable hydroxycarboxylic acid buffers include those described in Applicants' Assignee's copending U.S. patent application Ser. No. 10/051,719, entitled ANTISEPTIC COMPOSITIONS AND METHODS.

The hydroxycarboxylic acid buffers of the present invention preferably include beta- and alpha-hydroxy acids (BHAs, AHAs, respectively, collectively referred to as hydroxy acids (HAs)), their salts, lactones, and/or derivatives thereof. These may include mono-, di-, and tri-functional carboxylic acids. Particularly preferred are HAs having 1 or 2 hydroxyl groups and 1 or 2 carboxylic acid groups. Suitable HAs include, but are not limited to, lactic acid, malic acid, citric acid, 2-hydroxybutanoic acid, 3-hydroxybutanoic acid, mandelic acid, gluconic acid, tartaric acid, salicylic acid, as well as derivatives thereof (e.g., compounds substituted with hydroxyls, phenyl groups, hydroxyphenyl groups, alkyl groups, halogens, as well as combinations thereof)). Preferred HAs include lactic acid, malic acid, and citric acid. These acids may be in D, L, or DL form and may be present as free acids, lactones, or salts thereof. Other suitable HAs are described in U.S. Pat. No. 5,665,776 (Yu et al.). The preferred HAs for use with iodine and in particular with povidone-iodine are lactic and malic acid. Various combinations of hydroxycarboxyiic acids can be used if desired.

A hydroxycarboxylic acid buffer is preferably present in a molar concentration of at least about 0.3 molar, more preferably at least about 0.45 molar, and most preferably at least about 0.6 molar. For formulations where very rapid microbial kill on skin is desired the hydroxycarboxylic acid buffer concentration is in excess of 0.7 molar.

Typically, the concentration of hydroxycarboxylic acid buffer in weight percent of the use composition is at least about 5 wt-% and often at least about 7 wt-%, based on the weight of the composition. The concentration of hydroxycarboxylic acid buffer is preferably no greater than about 15 wt-%, more preferably no greater than about 10 wt-%, and most preferably no greater than about 5 wt-%, based on the weight of the composition. It may also be convenient in some applications to supply concentrates that have much higher concentration of hydroxycarboxylic acid buffer but when diluted to the use concentration fall within the specified ranges.

Preferably, the ratio of hydroxycarboxylic acid ("HA") buffer (free acids, as well as lactones thereof, salts thereof, or derivatives thereof) to antimicrobial agent (for antiseptic compositions) is at least about 4.0 grams HA buffer per gram available iodine, more preferably, at least about 6.5 grams HA buffer per gram available iodine, and most preferably, at least about 9.0 grams HA buffer per gram available iodine.

Other Optional Ingredients

In addition to hydroxycarboxylic acid buffers, a variety of other ingredients may be added to the compositions of the present invention for desired effect. These include, but are not limited to, skin emollients and humectants such as those described in U.S. Pat. No. 5,951,993 (Scholz et al.), fragrances, colorants, tackifiers, plasticizers, etc.

For certain embodiments, particularly those that include systemically active pharmaceutical agents, it may be particularly appealing to add penetration-enhancing agents. Certain of these agents are preferably included in an oil phase, such as lauryl alcohol, oleyl alcohol, lauramide DEA, lauryl pyrrolidone-5-carboxylate, and ascorbyl palmitate, whereas others are preferably included in an aqueous phase, such as glycerin, propylene glycol, and tetraglycol. Other penetration enhancing agents are disclosed in U.S. Pat. No. 6,086,911 (Godbey).

Formulation of Preferred Embodiments With Low or No Tack

The preferred compositions of the present invention provide low tack or nontacky dry films, which can be removed with a water-soaked fabric such as a towel or simple gauze. Low tack is desirable to prevent skin from attaching together, such as beneath a breast or in a skin-fold.

The tack can be measured by spreading a film of about 4 milligrams (mg) of the composition per square centimeter of skin on an inner forearm and allowing this to dry thoroughly. A dry thumb (washed with IVORY soap and dried thoroughly before testing) is then pressed onto the dry film and immediately removed. In preferred formulations there is essentially no perception of tack similar to the performance of a 10% povidone-iodine solution (such as that commercially available under the trade designation BETADINE Surgical Solution from Purdue Frederick Company, Norwalk Conn.). The most preferred preps can also be evaluated by pressing a facial tissue such as a KLEENEX brand tissue available from Kimberly-Clark, Roswell, Ga. over the prep and releasing. The tissue should fall off under its own weight. Due to the variability in skin types this should be done with multiple subjects painted with the test compositions and multiple evaluators.

Tack of the dried composition can be due to various factors such as the Tg of the film-forming substantive polymer, and the level of hydrophilic additives (e.g., glycols, certain low molecular weight organic acids, certain surfactants, antimicrobial agents, and the like) in the formulation which may plasticize the film. For example, certain iodophors such as PEG- or PVP-based iodophors can be plasticized by low molecular weight hydrophilic compounds. These compounds can further retain water in the films and contribute to tack.

Despite their very hydrophilic nature, however, the preferred organic acid buffers of the present invention do not contribute significantly to higher tack. While not intending to be bound by theory this may be due to hydrogen bond association between the carboxylic acid and the pyrrolidone ring carbonyl or the ether oxygen of the iodophor.

The tack of the dried compositions can be particularly high if the formulations contain film-forming substantive polymers that are pressure sensitive adhesives at skin temperature. For such compositions, as well as others that may be tacky, certain excipients that can be added to reduce the tack. For example, the tack can be controlled by the addition of: high Tg polymers; certain polyfunctional acids; and certain surfactants.

Certain high Tg polymers, such as those having a Tg of at least about 30° C., preferably at least 50° C., more preferably at least 55° C., and most preferably at least about 70° C., can reduce the tack of a composition of the present invention significantly. Suitable such polymers include polyvinyl alcohols. A preferred high Tg polymer for reducing tack is hydrolyzed polyvinyl alcohol (PVA) having a degree of hydrolysis greater than about 97%. Such a material is commercially available under the trade designation CELVOL 305 as a 98–98.8% hydrolyzed PVA from Celanese Ltd., Dallas, Tex. (Tg reported as 75–80° C.). This material is particularly desirable because it is of a relatively low molecular weight having a viscosity in water at 4% at 23° C. of only 4.5–5.5 cps. Also, although it is rather hydrophilic, hydrolyzed PVA does not detrimentally affect the substantivity of a dried composition of the present invention. While not being bound by theory, it is believed that the high degree of hydrolysis contributes to low tack without detrimentally affecting substantivity due to the fact that these polymers are not cold water soluble and thus once dried may resist going back into solution.

It has also been found that certain polyfunctional acids can dramatically reduce the tack of a composition of the present invention. For example, malic acid may reduce the tack of a formulation compared a similar formulation having lactic acid in an equivalent molar amount. Molecules having 3 or more carboxylic acids are particularly effective in reducing the tack of certain compositions. For example, certain compositions having PSA film-forming polymers that include quaternary ammonium side-chain functional group monomers and long chain alkyl group monomers can be detackifed by the addition of citric acid. Formulations that are aggressively tacky can be modified to have very low tack at 3% citric acid and essentially no tack at 5% citric acid. While not being bound by theory, it is believed that these polyfunctional acids may be forming ionic crosslinks with the quaternary ammonium groups on the film-forming polymer.

Certain surfactants can reduce the tack of compositions of the present invention. Particularly effective are silicone copolyol surfactants, which are surfactants based on poly-dialkylsiloxanes having pendant side-chains of polyalkyleneglycols. Many of these surfactants dramatically reduce the tack of the formulations, however, most of these surfactants also inhibited the adhesion of PSA-coated products over the dry prep. Certain low molecular weight silicone copolyols, such as that commercially available under the trade designation MASIL SF-19CG from PPG Industries, are able to reduce the tack of the compositions and yet not significantly inhibit the adhesion of PSA-coated products.

Also, the tack of the compositions can be reduced by using polymers that are not PSA in nature. These polymers generally have a glass transition temperature of greater than about 30° C. For example, polymers having higher amounts of short chain alkyl group tend to have higher glass transition temperatures and thus can yield substantially nontacky compositions. For example, one class of preferred polymers is based on at least a ternary combination of side-chain amine group functional monomers copolymerized with both short chain alkyl (meth)acrylate hydrophobic monomers and long chain alkyl (meth)acrylate hydrophobic monomers.

In particular, the following two groups of polymers are highly desirable:

Polymer System A:

| Monomer | Class | Weight % Range | Weight % Preferred Range |
|---|---|---|---|
| Dimethylamine oxide methacrylate | amine group | 25–60 | 35–55 |
| Isobutyl methacrylate | long chain alkyl | 10–30 | 10–25 |
| Methyl methacrylate | short chain alkyl | 10–45 | 10–25 |
| (C12–C18)alkyl methacrylate | long chain alkyl | 0–30 | 5–15 |

Preparation of the amine oxide containing polymers is described later in the Example Section, however, it should be noted that the above percentages are given on a basis that all tertiary amine is converted to amine oxide. This may not always be the case. In preferred polymers at least about 50%, more preferably at least about 60%, and most preferably at least about 70%, of the tertiary amine is converted to the amine oxide. The most preferred polymer of this class is that commercially available under the trade designation DIAFORMER Z-731 from Clariant Corp., Mt Holly, N.C.

Polymer System B:

| Monomer | Class | Weight % Range | Weight % Preferred Range |
|---|---|---|---|
| Trimethylaminoethyl acrylate chloride | amine group | 20–50 | 35–45 |
| Methyl methacrylate | short chain alkyl | 10–55 | 40–50 |
| (C12–C18)alkyl acrylate | long chain alkyl | 0–30 | 2–15 |
| Butyl acrylate | long chain alkyl | 0–80 | 5–20 |

The most preferred polymer of this class includes 40% trimethylaminoethyl methacrylate chloride, 45% methyl methacrylate, 5% lauryl acrylate, and 10% butyl acrylate where all percentages are weight percent of the polymerizable composition.

Application and Use

The compositions of the present invention may be applied to the skin using any suitable means. Ordinarily an absorbent of some type such as gauze, foam sponges, non-woven fabrics, cotton fabrics, cotton swabs or balls, and the like, are soaked with the composition which is used to wipe the composition over the intended site. With very high activity compositions having exceptional wetting properties (e.g., higher alcohol content formulations), a single stroke prep may be all that is necessary. In most cases, however, it is believed that it helps to wipe the soaked absorbent across the skin several times, preferably in various directions, in order to thoroughly wet the skin and ensure good coverage into the finer details of the skin. In general, however, extensive scrubbing is not called for as is recommended by prior art products due to the enhanced activity resulting from the high concentration of organic buffer. For example, the manufacturer of BETADINE Surgical Scrub (Purdue Frederick Company, Norwalk, Conn.) specifies that the user scrub thoroughly for 5 minutes. The compositions of the present invention require scrubbing for less than about 60 seconds, preferably less than about 45 seconds, and most preferably for less than about 30 seconds, followed by a 2-minute wait without blotting. In order to maintain strict asepsis, however, the applier of a preoperative patient skin prep should start at the proposed site of the incision and work outward never returning to the incision site with a "dirty" applicator. The most preferred compositions of the present invention can be wiped on the skin in a simple overlapping motion taking care to cover each spot at least two or three times as the user works outward such that essentially no scrubbing is required.

For some applications it may be desirable to place a PSA-coated article over a film of the dried composition. For example, if the composition is used as a skin prep for precatheterization it is generally recommended to cover the puncture site to maintain sterility. This is generally done by placing gauze and tape or a wound dressing over the puncture site and on top of the dried composition. These products are PSA-coated articles and adhesion to the dried composition is important to maintain asepsis. Similarly, if the compositions are used as preoperative skin preps it is often desirable to place a PSA-coated drape (a so-called incise drape) over the dried prep. The purpose of the adhesive-coated drape is to seal off the nonsterile skin and provide the surgeon with a sterile surface. The surgeon makes the incision through this drape. Thus, it is important that the drape adhere to the dried composition and resist lift during the procedure.

In order to achieve good initial and prolonged adhesion of PSA-coated products such as tapes, wound dressings, incise drapes, and the like, it is highly desirable and preferable to formulate compositions with the following characteristics: a relatively low surfactant concentration (preferably no greater than about 10 wt-%, more preferably no greater than about 7 wt-%, even more preferably no greater than about 5 wt-%, and most preferably no greater than about 4 wt-%); one or more surfactants that associate or potentially associate with other components in the composition during and/or after dry down; one or more film-forming polymers with higher content of hydrophobic monomer; a relatively high film-forming polymer concentration (preferably at least about 2 wt-%, more preferably at least about 3 wt-%, and most preferably at least 5 wt-%); and a relatively low hydroxycarboxylic acid concentration (preferably no greater than about 15 wt-%, more preferably no greater than a bout 12.5 wt-%, and most preferably no greater than about 10 wt-%).

Medical tapes and dressings that adhere particularly well to the compositions of the present invention when dry include those utilizing acrylate-based pressure sensitive adhesives, block copolymer-based pressure sensitive adhesives (e.g., adhesives based on KRATON polymers commercially available from Kraton Polymers, Houston, Tex.), and rubber-based pressure sensitive adhesives. Examples include tapes and dressings commercially available from 3M Company, St. Paul, Minn., under the trade designations TRANSPORE, BLENDERM, STERI-STRIPS, MICROPORE, TEGADERM, STERIDRAPE, and IOBAN 2.

A pressure sensitive adhesive tape applied over the dried compositions of the present invention on skin preferably adheres at a level of at least about 50% of the level of adhesion of the pressure sensitive adhesive tape applied over dried povidone-iodine solutions (specifically BETADINE Surgical Scrub (7.5% povidone-iodine solution) and BETADINE Surgical Solution (10% povidone-iodine solution), both of which are commercially available from Purdue Frederick Company, Norwalk, Conn.). This can be measured by applying a thin uniform amount of the test composition to skin as described in the Examples Section, allowing the film to dry, applying the PSA-coated tape (such as 0.5 inch (1.27 cm) wide samples of 3M IOBAN 2 Antimicrobial Incise Drape (3M Company, St. Paul, Minn.)), and rolling with a 4.5-pound (2.1-kg), 2-inch (5.1-cm) wide roller. After waiting at least 1 minute, and preferably 5 minutes, the PSA-coated tape is removed at a peel angle of 180 degrees at a speed of 12 inches/minute (30.5 cm/minute). Due to the variability in skin types, a statistically relevant sample is employed, which is typically at least 8 subjects where at least 2 strips are applied to the backs of each subject.

The compositions of this invention, if applied in a thin film to the skin and allowed to dry, preferably allow immediate adhesion of medical adhesive products. That is, typically and preferably, within about 3 minutes of application of a thin film (or once the composition is dry to the touch), a PSA-coated product can be applied over the composition that will exhibit good adhesion in as little as about 5 minutes, preferably in as little as about 120 seconds, and most preferably in as little as about 60 seconds. Furthermore the adhesion is maintained for at least several hours after application.

For the present invention, the principal mode of failure of PSA-coated products, such as incise drapes, over dried skin preps is primarily exposure to moisture. Moisture that can dissolve part or all of the composition and contribute to lift may come from patient transpiration, perspiration, or from external sources such as surgical irrigation fluid, blood, catheter related edema and fluid, and the like.

EXAMPLES

The objects, features, and advantages of the present invention illustrated in the following examples, which incorporate particular materials and amounts, should not be construed to unduly limit this invention. All materials are commercially available unless otherwise stated or apparent. All parts, percentages, ratios, etc., in the examples are by weight unless otherwise indicated.

GLOSSARY

| Abbreviation | Name | Source |
|---|---|---|
| EHA | 2-ethylhexyl acrylate | BASF Corporation, Mt. Olive, NJ |
| LMA | lauryl methacrylate: SR313B | Sartomer, Exton, PA |
| SMA | stearyl methacrylate | Rohm and Haas, Philadelphia, PA |
| BA | butyl acrylate | Hoechst Celanese, Dallas, TX and ICI, Wilmington, DE |
| IBMA | isobutyl methacrylate | Monomer-Polymer & Dajac Lab. Inc., Feasterville, PA |
| IBOA | isobonyl acrylate | Shin-Nakamura Chemicals, Wakayama City, Japan |
| AA | acrylic acid | BASF Corporation |
| ACM | acrylamide | Cytec Industries, Inc., West Paterson, NJ |
| DMAEAMC or DMAEAM.Cl | dimethylaminoethyl acrylate methyl chloride quaternary salt (AGAFLEX FA1Q80MC) Also referred to as trimethylaminoethylmethacrylate chloride salt; 80% aqueous solution | Ciba Specialty Chemicals, Woodbridge, NJ |
| DMAEAMS | dimethylaminoethyl acrylate methyl sulfate | Ciba Specialty Chemicals |
| DMAEMA | dimethylaminoethyl methacrylate | Ciba Specialty Chemicals |
| DMAEA | dimethylaminoethyl acrylate (AGEFLEX FA1) | Ciba Specialty Chemicals |
| AM-90G | methoxy(polyethylene oxide) acrylate, EOA-9 (approximately 450 MW) | Shin-Nakamura Chemicals |
| MA | methyl acrylate | ICI |
| MMA | methyl methacrylate | ICI |
| EtOH | ethanol SDA-3A, anhydrous | Eastman |
| EtOH | ethanol N-190 | Worum Chemicals, Minneapolis, MN |
| $H_2O_2$ | hydrogen peroxide, 50% aqueous solution | Sigma-Aldrich Fine Chemicals, Inc., St. Louis, MO |
| VAZO 67 | 2,2'-azobis (2-methylbutanenitrile) | E. I. du Pont de Nemours and Company, Wilmington, DE |
| Ascorbic Acid | ascorbic acid, vitamin C | Amend Drug & Chemical Co. |
| NaOH | sodium hydroxide | Sigma-Aldrich Fine Chemicals, Inc. |
| D-C Additive 62 | Dow-Corning Additive 62 defoamer | Dow-Corning, Midland, MI |
| TBHP | t-butyl hydroperoxide, 70% in water | Arco Chemicals |
| SFS | sodiumformaldehyde sulfoxylate hydrate | Fluka |
| PLURONIC | PLURONIC block copolymer of poly(ethylene oxide) and poly(propylene oxide) | BASF Corporation |
| TBA | tertiary buty alcohol | Sigma-Aldrich Fine Chemicals |
| PVP-I | povidone-iodine USP | BASF Corporation |
| POLYSTEP B22 | ammonium laureth 12 sulfate | Stepan Company, Northfield, IL |
| LA | L lactic acid, High Pure 88, USP | Purac America, Lincolnshire IL |
| MLA | DL malic acid | Universal Preserv-a-Chem, Edison, NJ |
| SILWET L-7614 | Silicone copolyol | Witco Corporation, Greenwich, CT |
| DIAFORMER Z711, Z712, Z731, Z751 | aminoxide side-chain group acrylate | Clariant Corporation, Charlotte, NC |
| CELVOL 103, 305, 321 | 98–98.8% hydrolyzed polyvinyl alcohol | Celanese Ltd., Dallas, TX |
| CELVOL 502, 523 | 88% hydrolyzed polyvinyl alcohol | Celanese Ltd. |
| MACKAM | coco betaine | McIntyre Group Ltd., University Park, IL |
| CB-35 | | |
| THF | tetrahydrofuran | Sigma-Aldrich Fine Chemicals |
| DI water | deionized water | |
| CA | citric acid | Universal Preserv-a-Chem, Edison, NJ |
| MDA | mandelic acid | Sigma-Aldrich Fine Chemicals |
| MMB | MMB glycol | CBC (America) Corp. New York, NY |
| TL10 | NIKKOL TL-10 | Barnet Products Corp., Englewood Cliffs, NJ |
| | TWEEN 20 | ICI |
| | BRIJ 700 | ICI |
| PLURAFAC A39 | ceteareth 55 | BASF Corporation |
| SURFONIC N-150 | nonylphenolethoxylate having an HLB of 15 | Huntsman Corp., Austin TX |

Test Protocols

Inherent Viscosity (IV)

The inherent viscosity of a polymer is measured in accordance with the protocol described by Fred Billmeyer, Jr. at pages 84–85 of the textbook entitled "Textbook of Polymer Science," Second Edition, published by Wiley-Interscience (1971). Briefly, solution viscosity is measured by comparing the efflux time (t) required for a specified volume of polymer solution to flow through a capillary tube with the corresponding efflux time ($t_0$) for the solvent. The measured variables t, $t_0$, and solute concentration (c) are then used to calculate inherent viscosity (also know as Logarithmic Viscosity) using the equation:

$$\eta = (\ln t/t_0)/c$$

For the examples of the present invention, IV was determined as a 0.15 to 0.50 weight percent solution of the film-forming polymer in tetrahydrofuran (THF). Amine oxide containing polymers are not soluble in THF alone and thus are measured at a 0.15–0.5 weight percent solution in 50/50 THF/methanol by weight.

Molecular Weight Measurement

The polymer is diluted to 5 milligrams per milliliter (mg/mL) in THF and filtered with a 0.45 micron (i.e., micrometer) membrane; Mobile Phase: THF; Flow Rate: 1.0 milliliter per minute (mL/min); Detector: Waters 410 Refractive Index; Columns: UltraStyragel-6, 30×7.8 millimeters (mm) each; Standards: Polystyrene, narrow dispersity; ranging $7.5 \times 10^6$–580 molecular weight of polystryrene.

Human Skin Antimicrobial Activity

Many of the compositions were checked for antimicrobial activity in a method similar to ASTM testing method E-1173-93 Standard Test for Evaluation of a Pre-operative Skin Preparation except that the compositions were applied to the backs (considered a "dry" site) of healthy volunteers and the baseline bacterial flora counts as put forth in section 7.1 of the ASTM method were not as high. Preps were always compared to the 2-step application of BETADINE Surgical Scrub (7.5% povidone-iodine, Purdue Frederick Company, Norwalk, Conn.) and BETADINE Surgical Solution ("paint," 10% povidone-iodine, Purdue Frederick Company, Norwalk, Conn.) per the manufacturer's instructions. All studies were randomized block designs. On the Study Day, two samples for baseline microbial counts were taken, one from the upper back and one from the lower back, on opposite sides of the spine. The test formulations and the control were randomized on the back-usually four across the upper back and four across the lower back. The residual bacteria were sampled from all sites 2.0 minutes after completion of application. All test samples were applied using sterile gauze saturated with the test composition (fully wet and dripping) applied in one of two ways. In one method an approximately 2×2 inch (5.1×5.1 cm) area was "scrubbed" for 30 seconds using moderate pressure. In a second method the prep was applied by simply painting the site with moderate pressure 3 times in a continuous motion without stopping. BETADINE Surgical Scrub and BETADINE Surgical Solution were applied following manufacturer's directions. Briefly, BETADINE Surgical Scrub was applied with saturated gauze and scrubbed for 5 minutes, wiped off; and the BETADINE Surgical Solution applied in an outward spiral from center. The compositions of the invention, therefore, had a much shorter time to kill than did the BETADINE scrub and paint procedure. A minimum of 8 subjects were used in accordance with sections 8.2–8.3 of ASTM testing method E1173. All subjects refrained from using antimicrobial products for a minimum of 2 weeks. The log reduction from baseline was determined for each composition. If multiple sites were run the log reduction for each site was determined. Results are reported in average log reductions (numerical average of the log reduction values). Note that an appropriate neutralizer was first determined for each formulation tested in accordance with ASTM testing method E1173-93 section 6.7. For most polymer systems the following neutralizing sampling solution was used: 0.4 g potassium dihydrogen phosphate, 10.1 g sodium hydrogen phosphate, 1.0 g TRITON X100 surfactant available from Union Carbide Corp., Houston Tex., 4.5 g lecithin (CAS # 8002-43-5, available from Fisher Scientific, Fairlawn, N.J. as Cat No. 03376-250), 45.0 g TWEEN 80 (ICI), 1.0 g sodium thiosulfate, and deionized water to bring the total volume to 1 liter. The sampling solution was prepared by adding all components together and heating with stirring to approximately 60° C. until dissolved. It was then placed in containers and steam sterilized.

Certain of the quaternary polymers have been shown to have antimicrobial activity and require appropriate neutralizers as described herein. Polyanionic polymers such as polysulfonic acid polymers capable of precipitating out the quaternary polymers work well. The preferred polysulfonic acid polymers are available as AQ polyesters from Eastman Chemical Company, Kingsport Tenn., and particularly preferred is AQ 55S, which is reported to be a linear amorphous polyester based on sodium sulfoisophthalic acid. EASTMAN AQ 55S polymer is further described as a relatively high molecular weight having a dry Tg of about 55° C. This was dispersed in water at 30% by weight in water prior to addition to the naturalization media. When necessary this was added to the sampling solution as 70 g of the 30% wt/wt solution of AQ55S in water prior to adjusting the final volume to 1 liter with water.

Substantivity Test

Selected compositions were applied to the forearms of healthy volunteers. The composition was applied as a uniform wet coating in an amount of approximately 4 milligrams per square centimeter ($mg/cm^2$) and allowed to thoroughly dry (typically a minimum of 5 minutes) over an area of approximately 5×5 cm. The dried composition was exposed to running tap water at a temperature of 23° C.–24° C. and a flow rate of about 2.5 liters/minute (L/min). The water was allowed to hit the arm immediately above the test site and run down over the site. The arm was held at an angle of approximately 45 degrees and the water was allowed to drop from approximately 15 cm before it hits the arm. The time for complete loss of color was recorded. BETADINE Surgical Solution (10% povidone-iodine, "paint") was often used as a control and this typically lasts for less than 5 seconds. Compositions that are not colored may be tested by addition of a suitable colorant. The colorant should not adversely affect the substantivity and thus pigments are often employed.

Certain samples were evaluated qualitatively by applying samples in the same manner and checking for resistance to wash off, however, the time was not recorded. For these samples "very good" refers to compositions that resist wash off very well and are believed to have a substantivity value in excess of 60 seconds, "good" refers to compositions that have a substantivity value of greater than 30 seconds, and "low" refers to compositions that have a substantivity value of 15–30 seconds.

Tack Test

The tack of dried compositions was evaluated after applying to the forearms of healthy volunteers and allowing the compositions to dry. A composition was applied as a uniform wet coating in an amount of approximately 4 $mg/cm^2$ and allowed to thoroughly dry (typically a minimum of 5 minutes (min)). The tack was evaluated by pressing a clean finger or thumb (washed and dried thoroughly) onto the composition with moderate pressure for 3–5 seconds and releasing. The tack was rated subjectively as no tack (equivalent to BETADINE Surgical Solution, i.e., 10% povidone-iodine, "paint")), very low tack (very slight sticking to the test finger, little and no visible skin deformation of the coated skin upon removal of the test finger, KLEENEX tissue can be pressed on and falls off under its own weight), low tack (slight sticking to the test finger with some upward deformation of the coated skin indicating adhesion, KLEENEX tissue can be pressed on and removed with slight or no fibers), moderate tack (sticks to the test finger with visible deformation of the coated skin upon removal, KLEENEX tissue will tear upon removal), or high tack (sticks so much that the coated skin visibly pulls up significantly as the test finger is slowly removed).

Incise Drape Adhesion Test

The adhesion of adhesive products over the compositions of the present invention was evaluated by both a qualitative use test and a quantitative peel test.

Qualitative Test: In the qualitative test, a sample was applied to the forearm as described above for the Substantivity test to one side of a forearm. On the lateral side was painted BETADINE Surgical Scrub ("scrub," 7.5% povidone-iodine) and BETADINE Surgical Solution ("paint," 10% povidone-iodine) per the manufacturer's instructions. Both were allowed to dry for at least 5 minutes. A sample of 3M IOBAN 2 Antimicrobial Incise Drape (3M Company, St. Paul, Minn.) was applied over the dried test sites and the drape worn for about 2 hours. After the wear period any lift of the incise drape was noted. The drape was removed by peeling and the adhesive was qualitatively evaluated based on the force needed to remove and the paint felt upon removal as low (less than BETADINE scrub and paint solutions), moderate (equivalent to BETADINE scrub and paint solutions), or good (better than BETADINE scrub and paint solutions).

Quantitative Test: Sixteen (16) volunteers had the test compositions applied to their backs by simply painting the site with gauze saturated with the test composition using moderate pressure three times in a continuous circular motion. The prep was allowed to dry for 5 minutes after which ½ inch (1.27 cm) wide strips of 3M IOBAN 2

Antimicrobial Incise Drape were very gently applied over the dry composition. Within 5 minutes the samples were rolled with a 4.5-lb (2.1-kilogram (kg)), 2-inch (5.1 cm) roller to ensure uniform application pressure. The drape samples were removed 10 minutes after application using a force-measuring instrument at a peel angle of 180 degrees (unless otherwise noted) and a speed of 12 inches/min (30.5 cm/min). The average force required to remove the sample over a 3-inch (7.6-cm) length was recorded. The reported value is the average of the values from all 16 subjects.

Brookfield Viscosity Test

The viscosity was measured using a Brookfield RVT ROTOVISCO viscometer commercially available from Engineering Labs Inc. (Middleboro, Mass.) with a small sample adapter (ULA adapter) LVDVI+. Measurements were taken at 23° C.–25° C. using spindle size 00 at a speed of 30 revolutions per minute (rpm).

Rabbit Eye Irritation Test

Compositions were evaluated for their potential for eye irritation compared to commercially available antiseptics: BETADINE Surgical Scrub (7.5% povidone-iodine) and BETADINE Sterile Ophthalmic Prep Solution (5% povidone-iodine). The test involved instilling into the eyes of adult New Zealand White albino rabbits weighing 2.0–3.5 Kg of either sex. Proper husbandry of the animals prior to testing is ensured including clean housing, high fiber rabbit diets (No. 5326 Purina Mills, Inc.), proper clean watering, proper environmental control (16° C.–22° C., 30%–70% relative humidity, and a 12 hour light/12 hour dark cycle). All animals were acclimated for at least 5 days and were given various cage-enrichment devices. Eyes were examined using sodium fluorscein dye on the day before the test material administration to ensure no sign of corneal injury or eye abnormality was present. Each test material was administered to three rabbits with 0.1 mL of undiluted test material/eye for two consecutive days. The eyelids were gently held together for 1 second before releasing to prevent loss of the material. The eyes of the rabbits remained unflushed for approximately 24 hours following instillation of the test material. The right eye of each animal was treated while the left eye remained untreated as a control. The eyes were examined for ocular irritation at 1, 4, 24, 48, and 72 hours after their respective treatment. Additional observations were made at 96 and 120 hours if irritation was present at 72 hours. Sodium Fluoroscein was used to aide in revealing possible corneal injury for each animal beginning with the 24-hour examination and each continuing examination until a negative response was attained. Irritation was scored using the Ocular Draize Technique (J. H. Draize: "Dermal Toxicity," *Appraisal of the Safety of Chemicals in Foods, Drugs and Cosmetics*, Association of Food and Drug Officials of the U.S., 1959, pages 46–59) with some modification. The maximum total score for these examples was the sum of scores obtained only from the conjunctivae. Total maximum score possible is 60 (20 per eye times three eyes). Notes were made with respect to the Cornea opacity, but this was not included in the scoring.

Starting Materials

Preparation Polymer A

The amounts of each chemical compound given in Table 1a were weighed into a quart-size bottle (1.06 liters) and mixed together into a homogeneous solution.

TABLE 1a

Materials used in Polymer A Preparation

| Amount (grams) | Description |
| --- | --- |
| 150.0 | 2-EHA |
| 50.0 | DMAEAMC |
| 10.0 | AM-90G |
| 0.5 | VAZO 67 |
| 190.0 | EtOH (N-190) |

The mixture in the bottle was purged with nitrogen to remove oxygen and sealed with a TEFLON fluoropolymer resin (E. I. du Pont de Nemours and Company) lined metal cap. The bottle was placed in an apparatus for rotating closed containers in a thermostatically controlled water bath at 60° C. for 24 hours. The inherent viscosity (IV) of the polymer was determined (see Test Protocol for inherent viscosity) to be 0.11 in THF. The conversion of monomer to polymer was 99.6%.

Deionized (DI) water (450 grams (g)) was added to the bottle to disperse the polymer to 23.5% solids. The dispersion was neutralized to pH=6–7 by addition of 10% NaOH solution. Next the dispersion was scavenged to reduce residual monomer levels with TBHP/SFS ratios of 700/600, 700/600, 700/500 parts per million (ppm) three times at 60° C. The scavenging reaction was performed by: 1) adding the first charge of TBHP (2.8 g of a 5% ethanol solution) and stirring for 10 minutes; 2) adding the first charge of SFS (2.4 g of a 5% aqueous solution) and stirring for another 30 minutes; 3) repeating 1) and 2) two additional times. The resulting dispersion was neutralized to pH=7–8 by addition of 10% NaOH solution, followed by stripping of ethanol under reduced pressure at 60° C. to 70° C. in a water bath. About 150 g of DI water was added during the stripping process to make up of the distilled ethanol. The final properties for the polymer dispersion were: solids, 26.8%, Mw/Mn=58.2/16.5K; Inherent Viscosity, 0.13 in THF; residual monomers, all monomers were below 10 ppm.

Preparation of Polymer B

The amounts of each chemical compound given in Table 1b were weighed into a quart-size bottle (1.06 liter) and mixed together into a homogeneous solution.

TABLE 1b

Materials used in Polymer B Preparation

| Amount (grams) | Description |
| --- | --- |
| 7.5 | LMA |
| 15.0 | BA, ICI |
| 75.0 (80% in water) | DMAEAMC |
| 67.5 | MMA |
| 0.375 | VAZO 67 |
| 207.0 | EtOH, anhydrous |
| 3.0 | DI water |

The mixture was degassed, sealed and polymerized as described in Preparation for Polymer A. The conversion of monomer to polymer was greater than 99.5%. DI water (375 g) was added to the bottle to disperse the polymer to 20% solids. The dispersion was scavenged to reduce residual monomer levels with TBHP/SFS ratios of 1000/1000, 800/700, 800/700 ppm three times at 60° C. as described in Preparation of Polymer A. The scavenged dispersion was distilled to remove ethanol at atmospheric pressure. D-C Additive 62 (at 0.30% based on solids) was added to control the foaming during the distillation process. The final sample was thick and clear. The analytical results for the polymer dispersion were: solids, 20.5%; Brookfield Viscosity, 6000 cps; pH=3.9; residual monomers, none except for 3 ppm DMAEAMC.

Preparation of Polymer C

The amounts of each chemical compound given in Table 1c were weighed into a quart-size bottle (1.06 liter) and mixed together into a homogeneous solution.

TABLE 1c

Materials used in Polymer C Preparation

| Amount (grams) | Description |
|---|---|
| 7.5 | LMA |
| 37.5 | IBMA |
| 52.5 | DMAEMA |
| 52.5 | MMA |
| 0.75 | VAZO 67 |
| 350 | EtOH, anhydrous |

The mixture was degassed, sealed, and polymerized as described in Preparation for Polymer A except at 75° C. for 16 hours. The conversion of monomer to polymer was 97.4% and the inherent viscosity was 0.33 in THF.

Next 25 g of a 50% aqueous solution of $H_2O_2$ ($H_2O_2$/amine molar ratio of 1.1) was added to the polymer to oxidize the tertiary amine to amine oxide at 60° C. for 20 hours.

The oxidized polymer was mixed with DI water in equal parts to form a clear aqueous dispersion. The dispersion was scavenged with TBHP/SFS ratios of 1000/1000, 1000/1000, 1000/1000 ppm at 60° C. three times as was described in Preparation of Polymer A. Next ethanol was stripped off under reduced pressure with about 0.05% D-C Additive 62 defoamer. The stripped ethanol was replaced with 155 g of DI water. The final dispersion had the following properties: solids, 17.1%; Brookfield viscosity, 19600 cps; pH=7.7; residual monomers, LMA/IBMA/DMAEMA/MMA=570/770/none detected/75 ppm based on polymer solids.

General Composition Preparation for Examples

The compositions of the present invention were prepared in the following manner. For compositions incorporating povidone-iodine (PVP-I) the PVP-I was first dissolved in DI water at 30% solution by weight. In general, the addition order is not critical, however, it is preferred to follow the general order listed below:

a. Weigh into the sample jar all hydrolytically stable nonionic surfactants especially those that may be solids and may require heating to dissolve, e.g., BRIJ 700.
b. Add the water, mix, and heat if necessary (e.g., to about 60° C.) to dissolve any surfactants/polymers which may take 1-2 hours.
c. Add in buffer components one at a time with complete mixing in between additions.
d. Adjust pH by addition of 5N sodium hydroxide to about 2.5-6.0, preferably 3.5-4.0.
e. Optionally, add in any surfactants that may not be as hydrolytically stable, e.g., surfactants comprising ester linkages.
f. Optionally add in any anionic surfactants.
g. Add antimicrobial or other active agent, e.g. PVP-I as a 30% solution concentrate in water.
h. Add the film-forming polymer solution and mix.
i. Make any final pH adjustments that may be necessary.

Examples 1–10

Examples 1–10 illustrate the use of a quaternary ammonium side-chain functional polyacrylate polymer having an additional hydrophilic monomer (a polyethoxylated acrylate, AM-90G) and an amine equivalent weight of 1039 g polymer/equivalent quaternary amine, which is a PSA at room temperature. These compositions were prepared as outlined above for Preparation Polymer A and the General Composition Preparation using the components listed in Tables 2a and 2b.

Compositions were evaluated for human skin antimicrobial activity on human volunteers as described in the test protocol using the 30-second "scrub" application technique. Compositions were also evaluated for substantivity, tack, and incise drape adhesion as outlined in the test protocols. The results are shown in Table 2a and 2b. All component quantities are shown on a solids basis.

TABLE 2a

Compositions and Results of the Antimicrobial Activity, Substantivity, Tack, and Incise Drape Adhesion for Examples 1–4P

| Component | Example Number | | | | | |
|---|---|---|---|---|---|---|
| (Amount in wt-%) | 1 | 2 | 2P[1] | 3 | 4 | 4P |
| 75/20/5 of 2-EHA/DMAEAMC/AM-90G | 5.00 | 5.00 | 5.00 | 5.00 | 5.00 | 5.00 |
| PVP-I | 7.50 | 7.50 | 0.00 | 7.50 | 7.50 | 0.00 |
| PVP 30K | 0.00 | 0.00 | 0.00 | 0.00 | 0.00 | 7.50 |
| POLYSTEP B22 | 5.00 | 0.00 | 0.00 | 0.00 | 0.00 | 0.00 |
| Ethanol | 3.30 | 5.00 | 5.00 | 5.00 | 5.00 | 5.00 |
| Lactic Acid | 6.00 | 5.00 | 5.00 | 0.00 | 3.00 | 3.00 |
| Citric Acid | 0.00 | 6.00 | 6.00 | 8.00 | 3.00 | 3.00 |
| Malic acid | 0.00 | 0.00 | 0.00 | 5.00 | 5.00 | 5.00 |
| NIKKOL TL10 | 0.00 | 5.00 | 5.00 | 5.00 | 5.00 | 5.00 |
| Water | 73.2 | 66.50 | 74.00 | 64.50 | 66.50 | 66.50 |
| pH | 3.5–4 | 3.5–4 | 3–4 | 3–4 | 3–4 | 3–4 |
| Substantivity (sec) | >60 | >60 | >60 | >60 | >60 | >60 |
| Tack | High | Moderate | | Low | Moderate | |
| Microbial kill (log reduction) | 1.9 | 2.35 | 0.6 | 1.9 | 1.8 | 1.4 |
| Incise Drape Adhesion (g/2.54 cm) | | 36 | | | | |
| BETADINE kill (log reduction) | 2.5 | 2.3 | 2.3 | 2.3 | 2.3 | 2.3 |

[1]Placebo of Example with same number

TABLE 2b

Compositions and Results of the Antimicrobial Activity, Substantivity, and Tack for Examples 5–10

| Component | Example Number | | | | | |
|---|---|---|---|---|---|---|
| (Amount in wt-%) | 5 | 6 | 7 | 8 | 9 | 10 |
| 75/20/5 of 2-EHA/DMAEAMC/AM-90G | 3.50 | 3.50 | 3.50 | 3.50 | 3.50 | 2.50 |
| PVP-I | 6.50 | 7.50 | 7.50 | 7.50 | 7.50 | 7.50 |
| Ethanol | 5.00 | 3.00 | 3.00 | 0.00 | 0.00 | 0.00 |
| Lactic Acid | 5.00 | 4.00 | 5.00 | 5.00 | 4.00 | 4.50 |
| Citric Acid | 3.00 | 0.00 | 3.00 | 1.00 | 0.00 | 0.00 |
| Malic acid | 0.50 | 4.00 | 3.00 | 3.00 | 3.00 | 2.50 |
| NIKKOL TL10 | 3.50 | 1.25 | 1.25 | 1.25 | 1.25 | 1.25 |
| BRIJ 700 | 0.00 | 1.00 | 0.00 | 1.00 | 1.00 | 1.00 |
| PLURONIC F127 | 0.00 | 0.00 | 1.00 | 0.00 | 0.00 | 0.00 |
| PLURONIC L64 | 0.00 | 0.00 | 0.00 | 0.00 | 0.30 | 0.30 |
| CELVOL 103 | 0.00 | 0.00 | 0.00 | 0.00 | 0.00 | 0.80 |
| SILWET L-7614 | 0.00 | 1.00 | 0.00 | 0.00 | 0.00 | 0.00 |

TABLE 2b-continued

Compositions and Results of the Antimicrobial Activity, Substantivity, and Tack for Examples 5–10

| Component | Example Number | | | | | |
|---|---|---|---|---|---|---|
| (Amount in wt-%) | 5 | 6 | 7 | 8 | 9 | 10 |
| Water | 73.00 | 74.75 | 72.75 | 77.75 | 79.45 | 79.65 |
| pH | 3–4 | 3–4 | 3–4 | 3–4 | 3–4 | 3–4 |
| Substantivity (sec) | | >60 | >60 | >60 | >60 | >60 |
| Tack | | Low | Moderate | Moderate | Moderate | Low |
| Microbial kill (log reduction) | 2.2 | 2.4 | 2.0 | 2.4 | 1.3 | 1.1 |
| BETADINE kill (log reduction) | 1.9 | 1.9 | 1.9 | 1.9 | 1.7 | 1.7 |

Results: Example 1 illustrates a composition with a quaternary ammonium side-chain polyacrylate film-forming polymer in combination with an anionic surfactant. The composition was found to be stable to prolonged storage (greater than 30 days) at 4° C., 45° C., 50° C., and 60° C. The composition was checked for antimicrobial activity twice. While the average log reduction appears less than BETADINE, the composition had biocidal activity statistically equivalent to BETADINE due to variability in the test method. This is surprising since the compositions of the present invention had a much abbreviated application time (2.5 min total contact time for Example 1 compared to a 5-min scrub with BETADINE Surgical Scrub followed by blotting, painting with BETADINE Solution, and allowing this to dry for a total time of greater than about 7 min). Examples 2, 2P (placebo), 3, 4, 4P (placebo), and 5 illustrate the use of a highly concentrated buffer systems based on lactic acid, malic acid, and citric acid in combination with the quaternary ammonium side-chain functional polymer in the presence of a nonionic surfactant. The compositions were found to be stable after 1 week of storage at 60° C. As expected, the active compositions, Examples 2 and 4, had better microbial kill than did the placebos, Example 2P and 4P. The "kill" of the placebo samples may be due to simply removing bacteria due to the application of the composition and subsequent sampling of the site. Examples 9 and 10 appeared to have relatively low antimicrobial activity apparently due to the presence of the PLURONIC L64. This surfactant has a relatively low HLB (15 reported by BASF, 8 by the standard calculation of % EO/5), which may account for this effect.

Example 1 had relatively high tack. Examples 2, 4, 7, 8, and 9 had moderate tack. The presence of the citric acid appears to help reduce the tack as seen in Example 3. The use of silicone copolyol surfactants also appears to reduce tack, however, Example 6 had low qualitative incise drape adhesion whereas Examples 7 and 8 had good qualitative incise drape adhesion. Example 10 also had lower tack due to the lower level of polyacrylate film-forming polymer and the presence of the PVA.

Example 2 was also evaluated in the quantitative adhesion test and found to remove easier than an incise drape applied over BETADINE Solution (36 vs. 55 g/2.54 cm).

All active containing formulations were applied to human skin and found to wet well and coat uniformly. The compositions could be easily painted uniformly on human skin due to the low viscosity. The dried films formed on skin were flexible, durable, and did not crack. The substantivity of all formulations was excellent with substantivity values greater than 60 seconds. Despite the good substantivity the samples could be easily removed by wiping with a wet paper towel. Furthermore, despite the lower polymer level (polymer/active ratio of 0.47 vs. a polymer/active ratio of 0.67 in Examples 1–4) in Examples 5–9, the compositions still had very good substantivity.

Examples 11–13

Examples 11–13 illustrate the use of a quaternary ammonium side-chain functional polymer, which is not a PSA at room temperature due to the high level of higher glass transition monomers (addition of MMA). These compositions were prepared as outlined above for Preparation Polymer A and the General Composition Preparation using the components listed in Table 3.

Compositions were evaluated for human skin antimicrobial activity on human volunteers as described in the test protocol using the 3-wipe paint application technique. Compositions were also evaluated for substantivity, tack, and incise drape adhesion as outlined in the test protocols. The results are shown in Table 3.

All components quantities are shown on a solids basis. By this it is meant that if a particular component is added as a solution in water the water is not included in the quantity of this component but rather reflected in the total amount of water in the composition.

TABLE 3

Compositions and Results of the Antimicrobial Activity, Substantivity, and Tack for Examples 11–13

| Component | Example Number | | | | |
|---|---|---|---|---|---|
| (Amount in wt-%) | 11 | 11P | 12 | 12P | 13 |
| 65/20/5/10 of 2-EHA/DMAEAMC/AM-90G/MMA | 3.50 | 3.50 | 3.50 | 3.50 | 3.50 |
| PVP-I | 7.50 | 0.00 | 7.50 | 0.00 | 7.50 |
| PVP 30K | 0.00 | 7.50 | 0.00 | 7.50 | 0.00 |
| Lactic Acid | 4.50 | 4.50 | 4.50 | 4.50 | 5.00 |
| Malic acid | 2.50 | 2.50 | 2.50 | 2.50 | 2.00 |
| NIKKOL TL10 | 2.50 | 2.50 | 1.50 | 1.50 | 1.50 |
| BRIJ 700 | 2.00 | 2.00 | 1.00 | 1.00 | 1.00 |
| CELVOL 103 | 0.50 | 0.50 | 0.50 | 0.50 | 0.00 |
| MACKAM CB-35 | 0.00 | 0.00 | 0.00 | 0.00 | 1.00 |
| Water | 77.00 | 77.00 | 79.00 | 79.00 | 78.50 |
| pH | 3–4 | 3–4 | 3–4 | 3–4 | 3–4 |
| Substantivity (sec) | >60 | | >60 | | >60 |
| Tack | Low | | Low | | Low |
| Microbial kill (log reduction) | 1.70 | 0.80 | 2.60 | 1.10 | 1.70 |
| BETADINE kill (log reduction) | 2.4 | 2.4 | 2.4 | 2.4 | 2.4 |

In general, the tack of these formulations was less than that of Examples 1–10 due to the higher glass transition polymer added (PVA). The microbial kill of Examples 11 and 12 were good and significantly higher than the placebo formulations. Example 12 killed as well as a BETADINE scrub and paint despite the very short exposure time. This is assisted by the high buffer level present in the samples. All samples had very good substantivity. Despite the good substantivity the samples could be easily removed by wiping with a wet paper towel. The compositions of Examples 11–13 could be easily painted uniformly on human skin due to the low viscosity. The dried films formed on skin were flexible, durable, and did not crack.

Examples 14–21

Examples 14–21 illustrate the use of high levels of organic acid buffer in combination with preferred quaternary amine and amine oxide side-chain functional substantive film-forming polymers. These compositions were prepared as outlined above for Preparation Polymer A (2-EHA) and Preparation Polymer C (LMA) and the General Composition Preparation using the components listed in Table 4a and 4b. The composition of DIAFORMER Z731 was analyzed by carbon NMR (determined by dissolving 100 milligrams (mg) dry polymer in 3 milliliters (mL) of a 50 micromolar ($\mu$M) Cr(OOCCH$_3$)$_3$ solution in CDCl$_3$) and found to be: 48.7% amine oxide of dimethylaminoethylmethacrylate, 18.8% IBMA, 20.8% MMA, 6.8% longer chain methacrylate (mixture of lauryl and stearyl), 0.9% dimethylaminoethanol, and 4.0% dimethylaminoethylmethacrylate. Titration of an aqueous solution of Diaformer Z731 in water with HCl and back again with NaOH showed that the amine oxide groups of the polymer are virtually 100% protonated at a pH of 4. Compositions were evaluated for human skin antimicrobial activity on human volunteers as described in the test protocol using the 3-wipe paint application technique. Compositions were also evaluated for substantivity and tack as outlined in the test protocols. The results are shown in Table 4a and 4b. All component quantities are shown on a solids basis.

TABLE 4a

Compositions and Results of the Antimicrobial Activity, Substantivity, and Tack for Examples 14–16

| Component (Amount in wt-%) | 14 | 14P | 15 | 15P | 16 | 16P |
|---|---|---|---|---|---|---|
| 15/35/50 2 EHA/DMAEAMC/MMA | 0.00 | 0.00 | 3.50 | 3.50 | 2.00 | 2.00 |
| 5/10/40/45 LMA/BA/DMAEAMC/MMA | 3.50 | 3.50 | 0.00 | 0.00 | 0.00 | 0.00 |
| DIAFORMER Z-731 | 0.00 | 0.00 | 2.50 | 2.50 | 2.00 | 2.00 |
| PVP-I | 7.50 | 0.00 | 7.50 | 0.00 | 7.50 | 0.00 |
| PVP 30K | 0.00 | 7.50 | 0.00 | 7.50 | 0.00 | 7.5 |
| Lactic Acid | 5.00 | 5.00 | 5.00 | 5.00 | 5.00 | 5.00 |
| Malic Acid | 2.00 | 2.00 | 2.00 | 2.00 | 2.00 | 2.00 |
| NIKKOL TL10 | 1.50 | 1.50 | 1.50 | 1.50 | 1.25 | 1.25 |
| BRIJ 700 | 1.50 | 1.50 | 1.50 | 1.50 | 1.00 | 1.00 |
| Water | 79.00 | 79.00 | 76.50 | 76.50 | 79.25 | 79.25 |
| pH | 3–4 | 3–4 | 3–4 | 3–4 | 3–4 | 3–4 |
| Microbial kill (log reduction) | 2.0 | 0.9 | 1.6 | 0.9 | 1.3 | 1.1 |
| BETADINE kill (log reduction) | 2.3 | 2.3 | 1.8 | 1.8 | 1.8 | 1.8 |
| Substantivity | >60 | | >60 | | >60 | |
| Tack | Very low | | Very low | | Very low | |

TABLE 4b

Compositions and Results of the Antimicrobial Activity, Substantivity, and Tack for Examples 17–21

| Component (Amount in wt-%) | 17 | 17P | 18 | 18P | 19 | 20 | 21 |
|---|---|---|---|---|---|---|---|
| 15/35/50 2-EHA/DMAEAMC/MMA | 0.00 | 0.00 | 3.50 | 3.50 | 3.50 | 0.00 | 3.50 |
| 5/10/40/45 LMA/BA/DMAEAMC/MMA | 2.00 | 2.00 | 0.00 | 0.00 | 2.50 | 0.00 | 0.00 |
| DIAFORMER Z-731 | 1.50 | 1.50 | 0.00 | 0.00 | 0.00 | 5.00 | 0.00 |
| PVP-I | 7.50 | 0.00 | 7.50 | 0.00 | 7.50 | 7.50 | 7.50 |
| PVP 30K | 0.00 | 7.50 | 0.00 | 7.50 | 0.00 | 0.00 | 0.00 |
| Lactic Acid | 5.00 | 5.00 | 5.00 | 5.00 | 5.00 | 5.00 | 5.00 |
| Malic Acid | 2.00 | 2.00 | 2.00 | 2.00 | 2.00 | 2.00 | 2.00 |
| NIKKOL TL10 | 1.50 | 1.50 | 1.50 | 1.50 | 1.50 | 1.50 | 1.00 |
| BRIJ 700 | 1.00 | 1.00 | 1.00 | 1.00 | 1.00 | 0.85 | 1.50 |
| Water | 79.50 | 79.50 | 79.50 | 79.50 | 77.00 | 78.15 | 79.50 |
| pH | 3–4 | 3–4 | 3–4 | 3–4 | 3–4 | 3–4 | 3–5 |
| Microbial kill (log reduction) | 1.7 | 0.6 | | | | | |
| BETADINE kill (log reduction) | 2.3 | 2.3 | | | | | |
| Substantivity | >60 | | >60 | | >60 | >60 | >60 |
| Tack | Very low | | Very low | | Very low | Very low | Very low |

The substantivity and tack results of all compositions were excellent. Despite the good substantivity the samples could be easily removed by wiping with a wet paper towel. The microbial kill of Examples 14–17 shows that the iodine containing formulations have good kill (log reduction greater than >1.5) in a panel of 8 participants where the average baseline was only 2.5–3.5) indicating that the high buffer level is promoting rapid antimicrobial activity. Furthermore, the high antimicrobial activity of these examples also demonstrates that the nonionic polyethoxylated alcohol and polyethoxylate sorbitan ester surfactants are compatible with the active ingredient povidone iodine. The placebo formulations (14P–17P) had relatively low microbial kill indicating that the iodine is the primary active ingredient. The viscosity of all of these examples was very low. The viscosity of formulations in Examples 14 and 20 were measured in accordance with the viscosity test and found to be 7.4 and 10 cps, respectively. Visually the viscosity values of the other examples were comparable. The low viscosity dramatically simplifies easy delivery of the prep over skin using a typical sponge type applicator. The compositions of Examples 14–21 could be painted easily and uniformly on human skin due to the low viscosity. The dried films formed on skin were flexible, durable, and did not crack.

Examples 22–24

Examples 22–24 illustrate the effect of the surfactant system on the stability of compositions comprising high levels of organic acid buffer. The quaternary ammonium side-chain functional polymer used in these examples was made according to the procedure of Preparation Polymer A and the General Composition Preparation using the components listed in Table 5. All component quantities are shown on a solids basis.

TABLE 5

Compositions and Stability of Examples 22–24

| Component (Amount in wt-%) | 22 | 23 | 24 |
|---|---|---|---|
| Citric acid | 5.0 | 5.0 | 5.0 |
| Water | 66.9 | 71.9 | 71.9 |

TABLE 5-continued

Compositions and Stability of Examples 22–24

| Component | Example Number | | |
|---|---|---|---|
| (Amount in wt-%) | 22 | 23 | 24 |
| Lactic Acid | 5.0 | 5.0 | 5.0 |
| Ethanol | 5.0 | 5.0 | 5.0 |
| NIKKOL TL10 (HLB= 16.7) | 5.0 | 0.0 | 0.0 |
| BRIJ 58 (HLB = 15.7) | 0.6 | 0.0 | 0.0 |
| BRIJ 76 (HLB = 12.4) | 0.0 | 0.6 | 0.0 |
| BRIJ 700 (HLB = 18.8) | 0.0 | 0.0 | 0.6 |
| 75/20/5 2EHA/DMAEMAC/AM90G | 5.0 | 5.0 | 5.0 |
| Povidone-Iodine USP | 7.5 | 7.5 | 7.5 |
| Surfactant System HLB | 16.6 | 12.4 | 18.8 |
| Stability | stable | unstable | unstable/floating precipitate |

The composition of Example 22 was only stable in the presence of the polysorbate 20 (NIKKOL TL10) at an intermediate HLB value. The high HLB single surfactant system of Example 24 and the low HLB single surfactant system of Example 23 both resulted in unstable compositions.

Examples 25–33

Examples 25–33 further illustrate the importance of HLB to ensure stability of the compositions comprising high organic acid buffer level and a substantive polymer. The polymer was an amine group functional side-chain polymer. The polymer used in these examples was made according to the procedure of Preparation Polymer A and the General Composition Preparation using the components listed in Tables 6a and 6b. Compositions were evaluated for stability as described below, as well as tack and incise drape adhesion as outlined in the test protocols. The results are shown in Tables 6a and 6b. All component quantities are shown on a solids basis. The HLB refers to that of the surfactant system.

The stability of the compositions was evaluated by two methods. In the first method the vial was held up to a bright over-head fluorescent light to evaluate clarity and color. In the second method the vial full of composition was evaluated using a very bright small illuminator (Model 78103, Vaginal Illuminator System F/58001, Welch-Allyn, Skaneateles Falls, N.Y.) The illuminator light source was placed directly on the bottom of the vial and the sample evaluated paying particular attention to the light path. Completely transparent samples, such as a solution of 10% povidone-iodine USP, appeared transparent with a light path that went almost straight through the vial with very little light diffraction. Samples that appeared cloudy by the fluorescent light evaluation method when tested with the illuminator often showed a light path that was conical and more diffuse. The stability was evaluated initially and after 4 days at 23° C. and 60° C.

The terms used to describe stability are: transparent means that the composition was a completely stable transparent solution when evaluated by both the fluorescent light and the illuminator; cloudy means that the composition appeared cloudy under the fluorescent light and illuminator and showed a diffuse light path with the illuminator. These samples were physically stable with no separation unless otherwise noted. Since they were not transparent a possible interaction may have occurred; precipitate means that a phase separation occurred usually accompanied by settling, which was usually visible under the fluorescent light and definitely visible under the illuminator; mocha means a more opaque appearance similar to mocha chocolate drinks under the fluorescent light. With the illuminator these mocha samples may or may not have appeared cloudy; and hazy means slightly cloudy under the fluorescent light but when evaluated with the illuminator the composition appeared transparent, but still was stable with no phase separation.

TABLE 6a

Composition and Results of Stability Test, Tack Test, and Incise Drape Adhesion Test for Examples 25–29

| Component | Example Number | | | | |
|---|---|---|---|---|---|
| (Amount in weight percent) | 25 | 26 | 27 | 28 | 29 |
| Citric acid | 3.0 | 0.0 | 3.0 | 0.0 | 2.0 |
| Lactic Acid | 5.0 | 4.0 | 5.0 | 4.0 | 4.0 |
| Malic Acid | 1.0 | 4.0 | 1.0 | 4.0 | 4.0 |
| NIKKOL TL10 | 2.0 | 2.2 | 2.0 | 1.0 | 1.0 |
| BRIJ 700 | 1.0 | 0.0 | 2.0 | 2.0 | 1.0 |
| PLURONIC F68 | 0.0 | 1.0 | 0.0 | 0.0 | 0.0 |
| POLYSTEP B22 | 0.0 | 0.0 | 0.0 | 0.0 | 3.0 |
| 75/20/5 of 2 EHA/DMAEAMC/AM-90G | 3.5 | 3.4 | 3.5 | 3.5 | 3.5 |
| Povidone-Iodine USP | 7.5 | 7.5 | 7.5 | 7.5 | 7.5 |
| Ethanol | 3.0 | 3.0 | 3.0 | 3.0 | 0.0 |
| Water | 74.0 | 74.9 | 73.0 | 75.0 | 74.0 |
| Stability | transparent/stable; color turned a little brown in 1week | cloudy/mocha color; precipitate after a few days | little precipitation over night at room temp/stable at 60° C. | | cloudy at room temp/stable at 60° C. with a muddy color |
| Tack | no tack | | | | |
| Incise Drape Adhesion Test | good adhesion | good adhesion better than Example 25 | | | |
| Surfactant System HLB | 17.27 | 20.41 | 17.65 | 18.03 | NA |

TABLE 6b

Compositions and Results of Stability Test for Examples 30–33.

| Component | Example Number | | | |
|---|---|---|---|---|
| (Amount in weight percent) | 30 | 31 | 32 | 33 |
| Lactic Acid | 4.0 | 4.0 | 4.0 | 4.0 |
| Malic Acid | 4.0 | 4.0 | 4.0 | 4.0 |
| NIKKOL TL10 | 1.0 | 1.0 | 1.0 | 1.0 |
| PLURONIC F127 | 1.0 | 1.0 | 1.0 | 1.0 |
| PLURAFAC A-39 PRILL | 0.0 | 1.0 | 0.0 | 0.0 |
| SURFONIC N-150 | 0.0 | 0.0 | 1.0 | 0.0 |
| PLURONIC P 65 | 0.0 | 0.0 | 0.0 | 1.0 |
| 75/20/5 of 2-EHA/DMAEAMC/AM-90G | 3.5 | 3.5 | 3.5 | 0.0 |
| Povidone-Iodine USP | 7.5 | 7.5 | 7.5 | 7.5 |
| Ethanol | 3.0 | 3.0 | 3.0 | 3.0 |
| Water | 76.0 | 75.0 | 75.0 | 78.5 |
| Stability | dark and transparent/stable | dark and transparent/stable | cloudy but stable solution | cloudy but stable solution |
| Surfactant System HLB | 15.75 | 16.75 | 12.25 | 13.25 |

The examples show that compositions with a surfactant system HLB of 12.25–18 are stable. However, it is believed that the most stable compositions are those that result in transparent solutions such as those of examples 25, 30, and 31, which have a surfactant system HLB of 15.75–17.27.

Examples 34–38

Examples 34–38 illustrate the use of a high Tg polymer dissolved in the composition to reduce the tack. The high Tg polyvinylalcohols added to the compositions were first dissolved as a concentrate in water at 10% by weight by adding the PVA to water and heating in a sealed vessel to 90° C. with occasional agitation until dissolved. The percent hydrolysis and viscosity as reported by Air Products Bulletin for a 4% aqueous solution at 20° C. are shown in Table 7a for the CELVOL polyvinylalcohols from Celanese Ltd., Dallas, Tex.

TABLE 7a

Percent Hydrolysis and Viscosity for CELVOL Polyvinyl Alcohols

| Polyvinyl Alcohol | Percent Hydrolysis | Viscosity[1] (cps) |
|---|---|---|
| CELVOL 321 | 98–98.8 | 16.5–20.5 |
| CELVOL 103 | 98–98.8 | 3.5–4.5 |
| CELVOL 305 | 98–98.8 | 4.5–5.5 |
| CELVOL 502 | 88 | 3–3.7 |
| CELVOL 523 | 88 | 23–27 |

[1]As reported by Air Products Bulletin for a 4% aqueous solution at 20° C.

The examples were made according to the General Composition Preparation using the components listed in Table 7b. Compositions were evaluated for stability as described for Examples 25–33, as well as, substantivity, tack and incise drape adhesion as outlined in the test protocols. The results are shown in Table 7b. All component quantities are shown on a solids basis.

TABLE 7b

Compositions and Results of Stability, Substantivity, Tack, and Incise Drape Adhesion for Examples 34–38

| Component | Example Number | | | | |
|---|---|---|---|---|---|
| (Amount in weight percent) | 34 | 35 | 36 | 37 | 38 |
| CELVOL 321 (PVA) | 1.00 | 0.00 | 0.00 | 0.00 | 0.00 |
| CELVOL 103 (PVA) | 0.00 | 1.00 | 0.00 | 0.00 | 0.00 |
| CELVOL 305 (PVA) | 0.00 | 0.00 | 1.00 | 0.00 | 0.00 |
| CELVOL 502 (PVA) | 0.00 | 0.00 | 0.00 | 1.00 | 0.00 |
| CELVOL 523 (PVA) | 0.00 | 0.00 | 0.00 | 0.00 | 1.00 |
| Water | 79.50 | 79.50 | 79.50 | 79.50 | 79.64 |
| Lactic Acid | 4.48 | 4.48 | 4.48 | 4.48 | 4.49 |
| Malic Acid | 2.50 | 2.50 | 2.50 | 2.50 | 2.50 |
| NIKKOL TL10 | 1.50 | 1.50 | 1.50 | 1.50 | 1.50 |
| BRIJ 700 | 1.02 | 1.02 | 1.02 | 1.02 | 0.87 |
| 75/20/5 of 2-EHA/DMAEAMC/AM-90G | 2.50 | 2.50 | 2.50 | 2.50 | 2.50 |
| Povidone-Iodine USP | 7.50 | 7.50 | 7.50 | 7.50 | 7.50 |
| Stability at 23° C. | Good | Very good | Poor | Very good | Poor |
| Substantivity | Very good | Very good | | Good | |
| Tack | Low | Very low | Low | Very low | Low |
| Incise Drape Adhesion | | Good | | Good | |
| Surfactant System HLB | 17.6 | 17.6 | 17.6 | 17.6 | 17.6 |

The substantivity of Examples 34 and 35 containing PVA with a very high degree of hydrolysis was very good. Note that the PVA components of these formulations are not cold water soluble due to the high degree of hydrolysis. Despite the good substantivity the samples could be easily removed by wiping with a wet paper towel.

Example 35 appeared to have the best adhesion of a PSA-coated product (incise drape) as tested by the qualitative test described above. It is not clear why the CELVOL 305 and 523 compositions were not stable in Examples 36 and 38.

Examples 39–42

Examples 39–42 illustrate the use of triclosan (Irgasan from Ciba Geigy) and chlorhexidine gluconate (CHG) as active ingredients. The film-forming substantive polymer was made according to the procedure of Preparation of Polymer A except the monomer ratios were 77/18/5 of 2-EHA/DMAEMA.C1/AM90G. The examples were made according to the General Composition Preparation using the components listed in Table 8. Compositions were evaluated for stability as described for Examples 25–33 and the results are shown in Table 8. All component quantities are shown on a solids basis.

TABLE 8

Compositions and Stability Results for Examples 39–42

| Component (Amount in weight percent) | Example Number | | | |
|---|---|---|---|---|
| | 39 | 40 | 41 | 42 |
| CHG[1] | 0.0 | 0.0 | 0.0 | 1.0 |
| Triclosan[2] | 1.0 | 0.4 | 0.5 | 0.0 |
| 77/18/5 of 2-EHA/DMAEMA. | 4.0 | 4.0 | 5.0 | 5.0 |
| Cl/AM90G | | | | |
| PVP-I | 0.0 | 0.0 | 7.5 | 0.0 |
| EtOH | 0.0 | 66.3 | 46.6 | 0.0 |
| Water | 95.0 | 29.3 | 40.4 | 94.0 |
| Stability | precipitate | transparent | dark solution | precipitated slowly |

[1]chlorhexidine gluconate was added as a 21% weight/volume solution in water
[2]triclosan was added as a 20% by weight solution in ethanol Precipitation is believed to be due to the antimicrobial coming out of solution. The results show that for these examples the triclosan is more stable in high alcohol containing systems due to solubility. Organic soluble actives such as triclo san may also be stabilized by the use of appropriate surfactants and hydrotropes. Note that triclosan was also stable in the presence of PVP-I illustrating the use of two active ingredients. The CHG sample was stable for a period of time but slowly formed a precipitate which is believed to be chlorhexidine chloride formed by the ion exchange with the chloride counterion from the film-forming polymer. This could be eliminated by choosing a counterion for the polymer which forms a soluble salt with chlorhexidine such as gluconate.

Examples 43–48

Examples 43–48 illustrate the use of the amine group side-chain containing substantive polymers in hydroalcoholic solvent systems. The polymers of these examples were made according to the Preparation of Polymer A with the monomer ratios altered to 80/15/5 2-EHA/DMAEME.C1/AM90G for Examples 44 and 46. The compositions were prepared according to the General Composition Preparation using the components listed in Table 9. Compositions were evaluated for stability as described for Examples 25–33 and the results are shown in Table 9. All component quantities are shown on a solids basis.

TABLE 9

Compositions and Stability Results for Examples 43–48

| Component (Amount in weight percent) | Example Number | | | | | |
|---|---|---|---|---|---|---|
| | 43 | 44 | 45 | 46 | 47 | 48 |
| Ethanol | 48.5 | 48.5 | 65.1 | 65.1 | 75.0 | 70.0 |
| 75/20/5 2-EHA/DMAEMA.C1/AM-90G | 6.0 | 0.0 | 6.0 | 0.0 | 3.3 | 4.6 |
| 80/15/5 2-EHA/DMAEMA.C1/AM-90G | 0.0 | 6.0 | 0.0 | 6.0 | 0.0 | 0.0 |
| PVP-I | 7.5 | 7.5 | 7.5 | 7.5 | 7.5 | 7.5 |
| Water | 38.0 | 38.0 | 21.4 | 21.4 | 14.2 | 17.9 |
| Ethanol:water by weight | 56:44 | 56:44 | 75:25 | 75:25 | 84:16 | 80:20 |
| Stability | dark solution | precipitate | dark solution | precipitate | precipitate | hazy |

The results indicate that at both the lower and intermediate ethanol concentration of Examples 43/44 and 45/46 (ethanol:water ratio of 56:44 for examples 43/44 and 75:25 for Examples 45/46) the substantive polymer with higher quaternary monomer (20%) was significantly more stable. Increasing the alcohol level further to a ratio of 80:20 resulted in a hazy solution in Example 48 and finally to 84:16 resulted in an unstable composition in Example 47.

Examples 49–50

Examples 49–50 illustrate the use of the quaternary ammonium biocidal active, benzethonium chloride in combination with povidone-iodine USP and a quaternary amine group side-chain containing substantive polymer in aqueous solution. The polymer of these examples was made according to the Preparation of Polymer A. The compositions were prepared according to the General Composition Preparation using the components listed in Table 10. Compositions were evaluated for stability as described for Examples 25–33. The substantivity was evaluated by applying the compositions to human skin according to the substantivity test. The results are shown in Table 10. All component quantities are shown on a solids basis.

TABLE 10

Compositions, Appearance, and Substantivity Test for Examples 49 and 50

| Components | Example Number | |
|---|---|---|
| (Amount in weight percent) | 49 | 50 |
| 70/25/5 2-EHA/DMAEMA.C1/AM-90G | 11.1 | 9.4 |
| PVP-I | 5.5 | 5.3 |
| Citric Acid | 1.7 | 1.1 |
| Isopropanol | 3.7 | 2.7 |
| Benzethonium Chloride USP | 2.5 | 1.9 |
| HOSTAPON CMT 30 (lauryl taurate) | 1.2 | 0.0 |
| RHODAPEX CO-436 (ammonium nonoxynol 4 sulfate) | 0.0 | 1.9 |
| Water | 74.3 | 77.7 |
| pH | 4.0 | 4.0 |
| Appearance | soluble/viscous | soluble/viscous |
| Substantivity | Low | Low |

The compositions of Examples 49 and 50 formed stable transparent but somewhat viscous solutions. The benzethonium chloride active ingredient appeared to detrimentally effect substantivity.

Examples 51–53

Examples 51–53 illustrate the use of various amine oxide side-chain group containing substantive film-forming polymers in compositions of the present invention. Preparation of amine oxide containing polymers is described in U.S. Pat. No. 6,123,933 (Hayama et al.). The compositions were prepared according to the General Composition Preparation using the components listed in Table 11. Compositions were evaluated for stability as described for Examples 25–33. The compositions were also evaluated for substantivity and tack as described in the test protocols. The results are shown in Table 11. All component quantities are shown on a solids basis.

TABLE 11

Compositions and Results of Stability Test, Tack Test, and Substantivity Test for Examples 51–53

| Components | Example Number | | |
|---|---|---|---|
| (Amount in weight percent) | 51 | 52 | 53 |
| BRIJ 700 | 1.00 | 1.00 | 1.00 |
| Malic Acid | 2.50 | 2.00 | 2.00 |
| Lactic Acid | 5.00 | 5.00 | 5.00 |
| NIKKOL TL10 | 1.50 | 1.24 | 1.24 |
| DIAFORMER Z-711 | 5.00 | 0.00 | 0.00 |
| DIAFORMER Z-731 | 0.00 | 5.10 | 0.00 |
| DIAFORMER Z-751 | 0.00 | 0.00 | 5.10 |
| Ethanol | 7.60 | 7.70 | 7.70 |
| PVP-I | 7.50 | 7.50 | 7.50 |
| Water | 69.90 | 70.46 | 70.46 |
| Stability at 23° C. for 1 week | Stable | Stable | Stable |
| Tack | Very Low | Very Low | Moderate |
| Substantivity | Low | Good | Good |

Based on NMR analysis it is believed that the composition of DIAFORMER Z711 and Z731 are as follows:

| | Z711 | Z731 |
|---|---|---|
| Amine oxide of dimethylaminoethylmethacrylate | 43.8 | 48.7 |
| Isobutylmethacrylate | 22.2 | 18.8 |
| Methylmethacrylate | 27.2 | 20.8 |
| long chain alkyl methacrylates[1] | 4.3 | 6.8 |
| Dimethylaminoethylmethacrylate | 1.6 | 4.0 |

[1]The long chain alkylmethacrylates are a mixture of lauryl and stearyl methacrylates. DIAFORMER Z751 is also an amine oxide side group containing polymer, however, the composition was not analyzed.

Substantivity was evaluated according to the substantivity test except that the time was not recorded. All three compositions are believed to have substantivity values in excess of 60 seconds (sec), however, the substantivity of Example 51 was less than that of Examples 52 and 53.

The results indicate that all samples produced stable compositions, however, the presence of the long chain acrylate monomers in the substantive polymer of Example 52 appeared to help improve the substantivity. The tack of Examples 51 and 52 was very low while that of Example 53 was moderate.

Examples 54–61

Examples 54–61 illustrate the us e of triclosan and chlorhexidine gluconate (CHG) as actives in compositions comprising amine oxide (DIAFORMER Z731, Examples 58–61) and quaternary amine (Examples 54–57) side-chain group functional substantive film-forming polymers. The quaternary polymer of Examples 54–57 was made according to the Preparation of Polymer C with the monomer ratios altered to 5/10/40/45 for LMA/IBMA/DMAEAMC/MMA. The compositions were prepared according to the General Composition Preparation using the components listed in Table 12. Compositions were evaluated for stability as described for Examples 25–33 and the results are shown in Table 12. All component quantities are shown on a solids basis.

TABLE 12

Compositions and Results of Stability Test for Examples 54–61

| Components | Example Number | | | | | | | |
|---|---|---|---|---|---|---|---|---|
| (Amount in grams) | 54 | 55 | 56 | 57 | 58 | 59 | 60 | 61 |
| BRIJ 700 (10%) | 7.50 | 7.50 | 7.50 | 7.50 | 5.00 | 5.00 | 5.00 | 5.00 |
| Water | 21.18 | 21.18 | 21.18 | 21.18 | 18.43 | 18.43 | 18.43 | 18.43 |

TABLE 12-continued

Compositions and Results of Stability Test for Examples 54–61

| Components | Example Number | | | | | | | |
|---|---|---|---|---|---|---|---|---|
| (Amount in grams) | 54 | 55 | 56 | 57 | 58 | 59 | 60 | 61 |
| DIAFORMER Z731 (17%) | 0.00 | 0.00 | 0.00 | 0.00 | 14.71 | 14.71 | 14.71 | 14.71 |
| NIKKOL TL-10 | 0.75 | 0.75 | 0.75 | 0.75 | 0.75 | 0.75 | 0.75 | 0.75 |
| LMA/IBMA/DMAEAMC/ MMA 5/10/40/45 (18.5%) | 9.46 | 9.46 | 9.46 | 9.46 | 0.00 | 0.00 | 0.00 | 0.00 |
| Triclosan (IRGASAN) | 0.50 | 1.00 | 0.00 | 0.00 | 0.50 | 1.00 | 0.00 | 0.00 |
| Chlorhexidine Gluconate (18% weight/volume in water) | 0.00 | 0.00 | 5.56 | 11.11 | 0.00 | 0.00 | 5.56 | 11.11 |
| Water | 10.61 | 10.11 | 5.55 | 0.00 | 10.61 | 10.11 | 5.56 | 0.00 |
| Total Weight | 50.00 | 50.00 | 50.00 | 50.00 | 50.00 | 50.00 | 50.00 | 50.00 |
| Stability | milky | milky | precipitate | precipitate | milky | milky | transparent | transparent |

The results indicate that compositions containing triclosan produced milky dispersions due to the low solubility of triclosan in water. The solubility may can be altered by addition of appropriate surfactants. The triclosan dispersions appeared "milky", which means that they looked like milk but were physically stable and did not phase split. CHG was stable in Examples 60 and 61 which included the amine oxide side-chain functional polymers but were not stable in the presence of the quaternary amine side-chain functional polymer in Examples 56 and 57. In these compositions a slight precipitate formed gradually over time. This is believed to be due to ion exchange of the gluconate and chloride ions resulting in precipitation of chlorhexidine chloride. For this reason, it is preferred to that if quaternary amine side-chain functional polymers are used in the presence of quaternary actives which may become unstable due to ion exchange that the counterion on the quaternary amine functional polymer be compatible with the active ingredient. In the case of CHG, suitable counterions include but are not limited to methosulfate, lactate, gluconate, acetate, and the like. The preferred counterion for use with chlorhexidine is methosulfate since dimethosulfate can be used to quaternize the tertiary amine to leave a suitable counterion and no ion exchange is necessary.

Example 62

Example 62 illustrates the use of protonated tertiary amine side-chain functional substantive film-forming polymer. The polymer was made according to the Preparation of Polymer A with the monomers and ratios altered to lauryl methacrylate/butyl acrylate/dimethylaminoethylacrylate/methylmethacrylate in a weight ratio of 5/10/40/45, respectively, and the polymer was left in ethanol (40% solids) and not inverted into water. The compositions were prepared according to the General Composition Preparation using the components listed in Table 13. All component quantities are shown on a solids basis.

TABLE 13

Composition and pH of Example 62

| | Example 62 | |
|---|---|---|
| Components | Weight in Percent by solids | Weight in grams |
| BRIJ 700 (20%) | 0.85 | 1.28 |
| Water | | 13.94 |

TABLE 13-continued

Composition and pH of Example 62

| | Example 62 | |
|---|---|---|
| Components | Weight in Percent by solids | Weight in grams |
| DIAFORMER Z731(17.1% in Water) | | |
| 5/10/40/45 lauryl methacrylate/ BA/DMAEA/ MMA (40% in EtOH) | 5.00 | 3.75 |
| Malic Acid | 2.00 | 0.60 |
| LacticAcid (88%) | 5.00 | 1.70 |
| 5N NaOH | 2.60 | 0.78 |
| TL-10 | 1.50 | 0.45 |
| PVP-I (30%) | 7.50 | 7.50 |
| Total | | 30.00 |
| pH | 4.15 | |

The composition was evaluated according to the Substantivity test except that the compositions were painted onto both 4 mil (0.1016 mm) biaxally oriented PET and 3M PANAFLEX 930 PVC (3M Company, Maplewood, Minn.) and allowed to dry according to the test method. The substantivity time was greater than 120 seconds for both samples. The film was very dark and well adhered even after 120 seconds. The sample on PET was still very well adhered and simple rubbing did not remove it. The samples were not painted on skin due to unknown residual monomer levels, however, they outperformed many of the quaternary amine and amine oxide functional polymer compositions when tested on these substrates for substantivity. These examples show that protonated tertiary amine functional polymers perform very well.

Examples 63–82 and Comparative Examples C1–C2

Examples 63–82 and Comparative Examples C1–C2 illustrate the use of various quaternary amine side-chain functional polymers in aqueous compositions comprising povidone-iodine USP as an active ingredient. Polymers were prepared as described in Preparation of Polymer A, except Example 82, which was prepared as described in Preparation of Polymer C and in the ratios indicated in Tables 14a, 14b, and 14c. The compositions were prepared according to the General Composition Preparation using the components listed in Tables 14a, 14b, and 14c. Substantivity was evaluated according to the substantivity test except that the time was not recorded. Tack was also evaluated as put forth in the Tack Test. The results are shown in Tables 14a, 14b, and 14c.

In the following tables the term "AEW" refers to Amine Equivalent Weight given in grams polymer/equivalent amine. All component quantities are shown on a solids basis.

TABLE 14a

Compositions and Results of the Substantivity and Tack Test for Examples 63–68 and Comparative Examples C1 and C2

| Components (Amount in weight percent) | C1 | C2 | 63 | 64 | 65 | 66 | 67 | 68 |
|---|---|---|---|---|---|---|---|---|
| 5/5/90 DMAEAMC/AM-90G/MA; AEW = 4154 | 5.0 | 0.0 | 0.0 | 0.0 | 0.0 | 0.0 | 0.0 | 0.0 |
| 80/20 2-EHA/DMAEAMC; AEW = 1034 | 0.0 | 5.0 | 0.0 | 0.0 | 0.0 | 0.0 | 0.0 | 0.0 |
| 15/85 DMAEAMC/MA; AEW = 1385 | 0.0 | 0.0 | 5.1 | 0.0 | 0.0 | 0.0 | 0.0 | 0.0 |
| 70/25/5 BA/DMAEAMC/AM-90G; AEW = 831 | 0.0 | 0.0 | 0.0 | 14.6 | 0.0 | 0.0 | 0.0 | 0.0 |
| 73/25/2 BA/DMAEAMC/AM-90G; AEW = 831 | 0.0 | 0.0 | 0.0 | 0.0 | 15.0 | 0.0 | 0.0 | 0.0 |
| 70/30 BA/DMAEAMC; AEW = 692 | 0.0 | 0.0 | 0.0 | 0.0 | 0.0 | 12.0 | 0.0 | 0.0 |
| 65/5/30 BA/DMAEAMS/AM-90G; AEW = 5380 | 0.0 | 0.0 | 0.0 | 0.0 | 0.0 | 0.0 | 4.9 | 0.0 |
| 63/7/30 BA/DMAEAMS/AM-90G; AEW = 3840 | 0.0 | 0.0 | 0.0 | 0.0 | 0.0 | 0.0 | 0.0 | 4.5 |
| PVP-I | 7.5 | 7.5 | 7.5 | 9.0 | 6.5 | 5.0 | 4.9 | 4.8 |
| Ethanol | 5.0 | 5.0 | 5.0 | 5.4 | 0.0 | 0.0 | 4.7 | 0.0 |
| 2-propanol | 0.0 | 0.0 | 0.0 | 0.0 | 4.4 | 0.0 | 0.0 | 0.0 |
| Citric Acid | 8.0 | 3.0 | 3.0 | 2.0 | 1.7 | 1.0 | 0.0 | 0.0 |
| Lactic Acid | 5.0 | 10.0 | 9.0 | 0.0 | 0.0 | 0.0 | 5.0 | 6.7 |
| WITCONATE 60T | 0.0 | 0.0 | 0.0 | 0.0 | 0.0 | 0.0 | 3.0 | 5.4 |
| NIKKOL TL-10 | 5.0 | 3.0 | 4.0 | 0.0 | 0.0 | 0.0 | 4.9 | 5.8 |
| Water | 64.5 | 66.5 | 66.4 | 69.0 | 72.4 | 82.0 | 77.6 | 72.8 |
| pH | | 4 | 4 | | 4 | 1.6 | 4 | 4 |
| Substantivity | Poor compatibility | Poor compatibility | | Good | Good | Low | Low | Low |
| Tack | | | Moderate | | | | | |

TABLE 14b

Compositions and Results of the Substantivity Test for Examples 69–76

| Components (Amount in weight percent) | 69 | 70 | 71 | 72 | 73 | 74 | 75 | 76 |
|---|---|---|---|---|---|---|---|---|
| 70/25/5 2-EHA/DMAEAMC/AM-90G/MA; AEW = 831 | 13.0 | 0.0 | 0.0 | 0.0 | 0.0 | 0.0 | 0.0 | 0.0 |
| 73/25/2 2-EHA/DMAEAMC/AM-90G; AEW = 831 | 0.0 | 16.0 | 0.0 | 0.0 | 0.0 | 0.0 | 0.0 | 0.0 |
| 75/25 2-EHA/DMAEAMC; AEW 831 | 0.0 | 0.0 | 5.0 | 0.0 | 0.0 | 0.0 | 0.0 | 0.0 |
| 70/30 2-EHA/DMAEAMC; AEW = 692 | 0.0 | 0.0 | 0.0 | 12.0 | 0.0 | 0.0 | 0.0 | 0.0 |
| 73/25/2 2-EHA/DMAEAMC/AM-90G; AEW = 831 | 0.0 | 0.0 | 0.0 | 0.0 | 4.0 | 0.0 | 0.0 | 0.0 |
| 75/20/5 2-EHA/DMAEAMC/AM-90G; AEW = 1039 | 0.0 | 0.0 | 0.0 | 0.0 | 0.0 | 5.0 | 0.0 | 0.0 |
| 77/18/5 2-EHA/DMAEAMC/AM-90G; AEW = 1154 | 0.0 | 0.0 | 0.0 | 0.0 | 0.0 | 0.0 | 6.1 | 0.0 |
| 75/20/5 2-EHA/DMAEAMC/AM-90G; AEW = 1039 | 0.0 | 0.0 | 0.0 | 0.0 | 0.0 | 0.0 | 0.0 | 5.0 |
| PVP-I | 6.6 | 8.9 | 7.5 | 5.2 | 6.5 | 7.5 | 7.6 | 7.5 |
| Ethanol | 0.0 | 4.8 | 0.0 | 0.0 | 0.0 | 1.0 | 4.1 | 0.0 |
| 2-propanol | 4.4 | 0.0 | 0.0 | 0.0 | 0.0 | 0.0 | 0.0 | 0.0 |
| Citric Acid | 1.6 | 1.6 | 1.0 | 1.0 | 0.0 | 0.0 | 0.0 | 0.0 |
| Lactic Acid | 0.0 | 0.0 | 0.0 | 0.0 | 0.0 | 6.0 | 5.2 | 6.0 |
| POLYSTEP B22 | 0.0 | 0.0 | 0.0 | 0.0 | 1.9 | 5.0 | 5.0 | 5.0 |
| NIKKOLTL-10 | 0.0 | 0.0 | 0.0 | 0.0 | 0.0 | 0.0 | 0.0 | 5.0 |
| PLURONIC F-38 | 0.0 | 0.0 | 0.0 | 0.0 | 0.0 | 0.0 | 0.0 | 0.6 |
| Water | 74.4 | 68.7 | 86.5 | 81.8 | 87.6 | 75.5 | 72.0 | 70.9 |
| pH | 4 | 4 | 3 | 1.6 | | | 4 | 3.9 |
| Substantivity | Good | Good | Low | Low | Good | Good | Good | Good |

TABLE 14c

Compositions and Results of the Substantivity and Tack Test for Examples 77–82

| Components | Example Number | | | | | |
|---|---|---|---|---|---|---|
| (Amount in weight percent) | 77 | 78 | 79 | 80 | 81 | 82 |
| 25/20/5/50 2-EHA/DMAEAMC/AM-90G/MA/IBOA; AEW = 1039 | 5.00 | 0.00 | 0.00 | 0.00 | 0.00 | 0.00 |
| 65/20/5/10 2-EHA/DMAEAMC/AM-90G/MMA; AEW = 1039 | 0.00 | 3.50 | 0.00 | 0.00 | 0.00 | 0.00 |
| 55/20/5/20 2-EHA/DMAEAMC/AM-90G/MMA; AEW = 1039 | 0.00 | 0.00 | 3.50 | 0.00 | 0.00 | 0.00 |
| 45/20/5/30 2-EHA/DMAEAMC/AM-90G/MMA; AEW = 1039 | 0.00 | 0.00 | 0.00 | 3.50 | 0.00 | 0.00 |
| 55/25/20 2-EHA/DMAEAMC/MMA; AEW = 831 | 0.00 | 0.00 | 0.00 | 0.00 | 3.50 | 0.00 |
| 5/10/40/45 LMA/BA/DMAEAMC/MMA; AEW = 519 | 0.00 | 0.00 | 0.00 | 0.00 | 0.00 | 3.5 |
| PVP-I | 7.50 | 7.50 | 7.50 | 7.50 | 7.50 | 7.5 |
| Ethanol | 5.00 | 0.00 | 0.00 | 0.00 | 0.00 | 0.00 |
| Citric Acid | 8.00 | 0.00 | 0.00 | 0.00 | 0.00 | 0.00 |
| Lactic Acid | 5.00 | 5.00 | 5.00 | 5.00 | 5.00 | 5.00 |
| Malic Acid | 0.00 | 2.00 | 2.00 | 2.00 | 2.00 | 2.00 |
| NIKKOLTL-10 | 5.00 | 2.50 | 2.50 | 2.50 | 2.00 | 1.50 |
| MACKAM L | 0.00 | 0.25 | 0.25 | 0.25 | 0.00 | 0.00 |
| Water | 64.5 | 79.25 | 79.25 | 79.25 | 80.0 | 88.0 |
| Substantivity | Good | Good | Good | Good | Good | Good |
| Tack | Moderate | Moderate | Moderate | Moderate | Moderate | Low |

Every composition performed much better in the substantivity test than BETADINE Surgical Solution (10% povidone-iodine) and were believed to have substantivity values greater than 15 sec. Examples judged as "low substantivity" were believed to have a substantivity value of 15–30 seconds or as "good substantivity" were believed to have a substantivity value of greater than 30 seconds.

Comparative Examples C1 and C2 illustrate that quaternary polymers with low quaternary amine content (high quaternary amine equivalent weights) in the absence of other hydrophilic monomers cannot produce stable compositions. "Poor Compatibility" refers to compositions that were not stable, i.e., had precipitate present or were very cloudy in appearance. Example 77 had a ratio of hydrophobic monomer to amine monomer higher than Comparative Example C2; however, due to the presence of the additional hydrophilic monomer the polymer was stable in the composition. The polymer of Example 63 had a high amine equivalent weight, which can produce a stable aqueous composition (very low lower alcohol content) in the absence of other hydrophilic monomers. Examples 64–73 illustrate various polymer compositions of the present invention. While the substantivity is judged as "low" it is substantially and demonstrably better than BETADINE Surgical Solution. Examples 67 and 68 incorporated polymers with the methosulfate salt of trimethylaminoethylmethacrylate in combination with lower levels of butyl acrylate and relatively high levels of AM-90G. The hydrophilic polyethoxylated AM-90G monomer helped to produce stable compositions at even very low amine content (high amine equivalent weight) but the compositions had low substantivity. This appears to yield less substantivity than Examples 63–65 which had higher levels of butyl acrylate. Surprisingly, Examples 71 and 72, which did not incorporate an additional hydrophilic monomer had less substantivity than Examples 69–70 which incorporated AM-90G. This indicates that some hydrophilic monomers may aid substantivity. While not being bound by theory it is believed that this may be due to either ensuring good film formation during dry down or interaction with the active ingredient povidone-iodine or both. Examples 73–76 illustrate PSA type film-forming polymers, which when incorporated into compositions of the present invention produced dry compositions with good substantivity. Examples 77–82 illustrate film-forming polymers with various levels of higher Tg comonomers (IBOA and MMA). Low levels of these monomers did not reduce tack significantly. Only when the level of the higher Tg comonomers was increased to over 30% (45% in Example 82) did the tack become significantly reduced.

Example 83

Example 83 illustrates the antimicrobial activity of a polymer based on trimethylaminoethylmethacrylate and laurylmethacrylate. The polymer and composition used were prepared in accordance with Example 14. The antimicrobial activity of the polymer in Example 14 was determined by the following method.

The composition of Example 14 was absorbed to saturation in gauze and applied to the inner forearm of a volunteer by simply painting the formulation on the arm 3 times in a continuous circular motion. The prep was allowed to stay in place for at least 2 minutes after which time a glass-sampling cylinder with an area of 5.04 $cm^2$ was pressed to the skin over the prep. Into this sampling cylinder was dispensed 2.5 mL sterile sampling solution. The sampling solution was mixed thoroughly in the glass cylinder on the arm using a TEFLON policeman for 1 minute making certain to rub over the skin in the entire area within the cylinder. The solution was removed and placed into a sterile test tube using a pipet. A second aliquot of 2.5 mL of sampling solution was added to the cylinder and the process repeated. The two 2.5-mL aliquots were combined into one tube. To the test tube was added 50 microliters of *Siaphylococcus epidermidis* ATCC Number 12228 at a concentration sufficient to yield a diluted concentration in the combined sampling solution of *Staphylococcus epidermidis* ATCC Number 12228 at a concentration sufficient to yield a diluted concentration in the combined sampling solution of approximately 20–50 colony forming units (CFU)/mL Control samples of both the Standard Sterile Solution (SSS) and Modified Sterile Solution (MSS) were also run. In one set of controls the bacteria were inoculated directly into SSS and MSS as well as into Butterfield's phosphate buffered water (PBW) (*Journal of Bacteriology*, Vol. 23, No. 355, (1932)) to determine if the sampling solutions were toxic to the bacteria.

PBW was made by making a 0.25M stock solution by putting 34 g $KH_2PO_4$ into 500 mL of DI water, adjusting the pH to 7.2 with 10N NaOH, and adding enough DI water to make 1 liter. The solution was filtered, sterilized, dispensed into a 1 liter sterile bottle, and stored under refrigeration. Butterfield's PBW was made by adding 1.25 mL of the stock solution to 900 mL of DI water and adding neutralizers, stirring, heating to dissolve the components, and diluting to 1 liter with DI water. The solution was mixed well, dispensed into two 500-mL bottles. The bottles containing the solution were autoclaved for 25 minutes at 121° C. The contents were carefully swirled after removing the bottles from the autoclave.

The inoculated samples were plated immediately and again after 30 minutes exposure to the solutions by adding 1 mL of the inoculated sampling solution to 13 mL Trypticase Soy Agar (TSA)media to check for growth. The plates were incubated at 35° C. for 3 days and the number of colonies counted using an illuminated magnified colony counter.

The sampling solutions were prepared as follows. A Standard Sampling Solution (SSS) contained: 0.4 g potassium dihydrogen phosphate, 10.1 g sodium hydrogen phosphate, 1.0 g TRITON X100 surfactant available from Union Carbide Corp., Houston Tex., 3.0 g lecithin (CAS No. 8002-43-5, available from Fisher Scientific, Fairlawn, N.J. as Cat No. 03376-250), 30.0 g TWEEN 80 (ICI), 1.0 g sodium thiosulfate, and deionized water to bring the total volume to 1 liter. The pH of the sampling solution was about 7.9 and ordinarily no adjustment was necessary. In addition, a Modified Sampling Solution (MSS) was prepared in the same manner as the SSS by addition of 70 g of a 30% by weight dispersion of Eastman AQ55S polymer to water followed by dilution to 1 liter. The sampling solution was prepared by adding all components together and heating with stirring to approximately 60° C. until dissolved. It was then placed in bottles and steam sterilized. The results of the antimicrobial activity are shown in Table 15a.

TABLE 15a

Results of Antimicrobial Activity of Control Solutions for Example 83

| Controls | Initial (0 min) No. of Colonies | % of PBW | 30 min No. of Colonies | % of PBW |
|---|---|---|---|---|
| SSS | 22 | 116 | 27 | 142 |
| MSS | 18 | 95 | 20 | 105 |
| PBW | 19 | — | 19 | — |

These results show that both the SSS and MSS were not toxic to the cells in the absence of any polymer-containing compositions.

Next, Example 14 was prepped on skin and removed with both SSS and MSS as described above. The results are shown in Table 15b.

TABLE 15b

The Results of Antimicrobial Activity for Example 83

| Controls | Initial (0 min) No. of Colonies | % of PBW | 30 min No. of Colonies | % of PBW |
|---|---|---|---|---|
| SSS | 16 | 84 | 1 | 5 |
| MSS | 21 | 110 | 22 | 116 |
| PBW | 19 | — | 19 | — |

The results showed that for the standard sampling solution (SSS) there was immediate and long term kill as compared to PBW. This was due to the presence of the quaternary amine polymer and not iodine since the sodium thiosulfate was in sufficient concentration to completely neutralize the iodine present. All samples were clear and colorless. The results further indicated that there was no antimicrobial activity after exposure to the MSS. The sulfonated AQ polymer MSS has been shown to precipitate the quaternary amine-containing polymer, thereby, neutralizing the activity. The lack of activity in MSS further supports the fact that the iodine was neutralized.

This example showed surprising activity of a 95% reduction in only 30 minutes. In this example the polymer concentration was not known but was likely very low. For purposes of evaluating the antimicrobial properties of polymers directly, 5 mL of 2 wt-% polymer in water was directly inoculated and checked for antimicrobial activity in the same manner. By this method the polymers preferably showed at least a 50% reduction, more preferably at least a 75% reduction, and most preferably at least a 90% reduction in bacteria in 30 minutes. These polymers may find utility as active antimicrobials for topical application such as treatment of acne, athletes foot, and the like, preservatives for cosmetics and foods, as well hard-surface disinfectants.

Examples 84–99

Examples 84–99 illustrate that most of the film-forming polymers form clear solutions in water. The polymers were dissolved at 1 wt-% in water and the percent transmission was measured at 650 nm. A water blank was used to calibrate the percent transmission to 100% for the water sample. The data is presented in Tables 16a, 16b, 16c, 16d, 16e, and 16f. The high percent transmission indicated that these polymers form solutions in water. Polymer compositions are given in weight percent monomer used to prepare the polymer.

TABLE 16a

Compositions and Results of Light Transmission at 650 nm for Examples 84–87

| Example Number | Monomers | | | | Percent Transmission at 650 nm |
|---|---|---|---|---|---|
| | 2-EHA | DMAEAMC | AM-90G | MMA | |
| 84 | 75 | 20 | 5 | | 96.5 |
| 85 | 15 | 35 | | 50 | 91.4 |
| 86 | 25 | 35 | 40 | | 94.1 |
| 87 | 55 | 25 | 20 | | 96.7 |

TABLE 16b

Compositions and Results of Light Transmission at 650 nm for Examples 88–89

| Example Number | Monomers | | | | Percent Transmission at 650 nm |
|---|---|---|---|---|---|
| | LMA | BA | DMAEAMC | MMA | |
| 88 |  | 15 | 40 | 45 | 100.5 |
| 89 | 5 | 10 | 40 | 45 | 99.5 |

TABLE 16c

Compositions and Results of Light Transmission at 650 nm for Examples 90–94

| Example Number | Monomers | | | | Percent Transmission at 650 nm |
|---|---|---|---|---|---|
| | SMA | IBMA | DMAEMA Oxide | MMA | |
| 90 | 10 | 20 | 45 | 25 | 100.6 |
| 91 | 6.5 | 18.5 | 55 | 20 | 100.7 |
| 92 | 15 | 15 | 55 | 15 | 100.7 |
| 93 | 11 | 23.5 | 42.5 | 23 | 101 |
| 94 | 5 | 30 | 35 | 30 | 99.2 |

TABLE 16d

Compositions and Results of Light Transmission at 650 nm for Example 95

| Example Number | Monomers | | | | Percent Transmission at 650 nm |
|---|---|---|---|---|---|
| | LMA | BA | DMAEMA Oxide | MMA | |
| 95 | 5 | 25 | 35 | 35 | 100 |

TABLE 16e

Compositions and Results of Light Transmission at 650 nm for Examples 96–97

| Example Number | DIAFORMER Polymers (See Examples 51–53) | Percent Transmission at 650 nm |
|---|---|---|
| 98 | DIAFORMER Z731 | 101 |
| 99 | DIAFORMER Z711 | 101 |

TABLE 16f

Compositions and Results of Light Transmission at 650 nm for Examples 98–99

| Example Number | Monomers | | | | Percent Transmission at 650 nm |
|---|---|---|---|---|---|
| | BA | 2-EHA | DMAEAMC | AM-90G | |
| 98 | 65 |  | 5 | 30 | 93.9 |
| 99 |  | 80 | 20 |  | 94 |

Comparative Examples C3–C20

Comparative Examples C3–C20 use highly charged quaternary amine side-chain functional group containing polymers comprised of only hydrophilic monomers. The polymer descriptions are shown in Table 17a.

TABLE 17a

Descriptions of Polymers used to make Comparative Examples C3–C20

| Polymer | Percent Solids | Description | Source |
|---|---|---|---|
| LUVIQUAT FC 550 | 40 | Polyquaternium-16 (vinylpyrrolidone/vinyl3-methylimidazolium chloride, 50/50, MW=80,000 by GPC) | BASF Corp., Mt. Olive, NJ |
| LUVIQUAT FC 370 | 40 | Polyquaternium-16 (vinylpyrrolidone/vinyl3-methylimidazolium chloride, 70/30, MW = 100,000 by GPC) | BASF Corp |
| LUVIQUAT Care | 7 | Polyquaternium-44 (vinylpyrrolidone/vinyl3-methylimidazolium methosulfate, 70/30, MW = 1,000,000 by GPC) | BASF Corp |
| MERQUAT 550 | 8 | Polyquaternium-7 (dimethyldiallylammonium chloride/acrylamide, MW= $10^6$–$10^7$) | Calgon Cor., Merck, Pittsburgh, PA |
| MERQUAT 295 | 40 | Polyquaternium-22 (95% dimethyldiallylammonium chloride/5% acrylic acid | Calgon Cor., Merck, Pittsburgh, PA |
| GAFQUAT 734 | 50 | Vinyl pyrrolidone/dimethylaminoethylmethacrylate quaternized with dimethosulfate | ISP Corp., Wayne, NJ |
| GAFQUAT HS-100 | 20 | Vinyl pyrrolidone/dimethylaminoethylmethacrylate quaternized with methyl chloride | ISP Corp. |
| GAFQUAT 755 | 20 | Vinyl pyrrolidone/dimethylaminoethylmethacrylate quaternized with dimethosulfate | ISP Corp. |
| ISP Copolymer 825 | 20 | Vinyl pyrrolidone/dimethylaminoethylmethacrylate | ISP Corp. |

The compositions were prepared according to the General Composition Preparation using the components listed in Tables 17b, 17c, 17d, and 17e. Compositions were evaluated for stability as described for Examples 25–33. The compositions were also evaluated for substantivity as described in the test protocols. The results are shown in Tables 17b, 17c, 17d, and 17e.

TABLE 17b

Compositions and Results of Stability and Substantivity Test for Comparative Examples C3–C7

| Component (Amount in grams and percent solids) | C3 grams | C3 % solids | C4 grams | C4 % solids | C5 grams | C5 % solids | C6 grams | C6 % solids | C7 grams | C7 % solids |
|---|---|---|---|---|---|---|---|---|---|---|
| LUVIQUAT FC 550 (40% solids) | 0.5 | 1.0 | 2.5 | 5.0 | 0.0 | | 0.0 | | 0.0 | |
| LUVIQUAT FC 370 (40% solids) | 0.0 | | 0.0 | | 0.5 | 1.0 | 2.5 | 5.0 | 0.0 | |
| LUVIQUAT Care polymer (7% solids) | 0.0 | | 0.0 | | 0.0 | | 0.0 | | 2.8 | 1.0 |
| Water | 14.5 | | 12.5 | | 14.5 | | 12.5 | | 12.2 | |
| PVP-I (30% solids) | 5.0 | 7.5 | 5.0 | 7.5 | 5.0 | 7.5 | 5.0 | 7.5 | 5.0 | 7.5 |
| Total | 20.0 | | 20.0 | | 20.0 | | 20.0 | | 20.0 | |
| Stability (after 23° C. for 2 days) | precipitated chunks | | stable | | very cloudy | | precipitate | | precipitated chunks | |
| Substantivity (seconds) | | | 8 | | | | | | | |

TABLE 17c

Compositions and Results of Stability and Substantivity Test for Comparative Examples C8–C12

| Component (Amount in grams and percent) | C8 grams | C8 % solids | C9 grams | C9 % solids | C10 grams | C10 % solids | C11 grams | C11 % solids | C12 grams | C12 % solids |
|---|---|---|---|---|---|---|---|---|---|---|
| LUVIQUAT Care polymer (7% solids) | 14.2 | 5.0 | 0.0 | | 0.0 | | 0.0 | | 0.0 | |
| MERQUAT 550 (8% solids) | 0.0 | | 2.6 | 1.0 | 12.5 | 5.0 | 0.0 | | 0.0 | |
| MERQUAT 295 (40% solids) | 0.0 | | 0.0 | | 0.0 | | 0.5 | 1.0 | 2.5 | 5.0 |
| Water | 0.8 | | 12.4 | | 2.5 | | 14.5 | | 12.5 | |
| PVP-I (30% solids) | 5.0 | 7.5 | 5.0 | 7.5 | 5.0 | 7.5 | 5.0 | 7.5 | 5.0 | 7.5 |
| Total | 20.0 | | 20.0 | | 20.0 | | 20.0 | | 20.0 | |
| Stability (after 23° C. for 2 days) | precipitated chunks | | stable | | stable | | very cloudy | | precipitate | |
| Substantivity (seconds) | | | 11.5 | | 14 | | | | | |

TABLE 17d

Compositions and Results of Stability and Substantivity Test for Comparative Examples C13–C17

| Component (Amount in grams and percent) | C13 grams | C13 % solids | C14 grams | C14 % solids | C15 grams | C15 % solids | C16 grams | C16 % solids | C17 grams | C17 % solids |
|---|---|---|---|---|---|---|---|---|---|---|
| GAFQUAT 734 (50% solids) | 0.4 | 1.0 | 2.5 | 5.0 | 0.0 | | 0.0 | | 0.0 | |
| GAFQUAT HS-100 (20% solids) | 0.0 | | 0.0 | | 1.0 | 1.0 | 5.0 | 5.0 | 0.0 | |
| GAFQUAT 755 (20% solids) | 0.0 | | 0.0 | | 0.0 | | 0.0 | | 1.0 | 1.0 |
| Water | 14.6 | | 13.0 | | 14.0 | | 10.0 | | 14.0 | |
| PVP-I (30% solids) | 5.0 | 7.5 | 5.0 | 7.5 | 5.0 | 7.5 | 5.0 | 7.5 | 5.0 | 7.5 |
| Total | 20.0 | | 20.0 | | 20.0 | | 20.0 | | 20.0 | |
| Stability | stable | | stable | | precipitate | | cloudy gel | | precipitated | |

TABLE 17d-continued

Compositions and Results of Stability and Substantivity Test for Comparative Examples C13–C17

| Component | Example Number | | | | | | | | | |
|---|---|---|---|---|---|---|---|---|---|---|
| (Amount in grams and | C13 | | C14 | | C15 | | C16 | | C17 | |
| percent) | grams | % solids | grams | % solids | grams | % solids | grams | % solids | grams | % solids |
| (after 23° C. for 2 days) | | | | | | | | | chunks | |
| Substantivity (seconds) | 20.3 | | 8.5 | | | | | | | |

TABLE 17e

Compositions and Results of Stability and Substantivity Test for Comparative Examples C18–C20

| Component | Example Number | | | | | |
|---|---|---|---|---|---|---|
| (Amount in grams | C18 | | C19 | | C20 | |
| and percent solids) | grams | % solids | grams | % solids | grams | % solids |
| GAFQUAT 755 (20% solids) | 5.0 | 5.0 | 0.0 | | 0.0 | |
| ISP Copolymer 825 (20% solids) | 0.0 | | 1.0 | 1.0 | 5.0 | 5.0 |
| Water | 10.0 | | 14.0 | | 10.0 | |
| PVP-I (30% solids) | 5.0 | 7.5 | 5.0 | 7.5 | 5.0 | 7.5 |
| Total | 20.0 | | 20.0 | | 20.0 | |
| Stability (after 23° C. for 2 days) | not miscible | | stable | | stable | |
| Substantivity (seconds) | | | 15 | | 14.8 | |

The pH was less than 3 for every example. Stable compositions were evaluated for substantivity according to the Substantivity Test. Compositions containing Polyquaternium-16 (C8–C11) were mostly unstable. Only C9 produced a stable composition, however, its substantivity was poor. Similarly Polyquaternium 44 did not produce stable compositions. Polyquaternium 7 did produce stable compositions; however, the substantivity was relatively low. Polyquaternium 22 samples did not produce stable compositions. The only other stable samples were produced using GAFQUAT 734 and Copolymer 825. The substantivity of these samples was relatively low—less than about 20 seconds. The stable compositions formed very brittle compositions on skin once dry and would likely flake off in a short period of time.

Examples 100–109

Examples 100–109 were prepared using an amine oxide functional polymer, DIAFORMER Z731. The DIAFORMER Z731 was received in ethanol. The water was added and the ethanol stripped out on a rotary evaporator to yield a solution, which was 17% solids. The DIAFOMER Z731 amine oxide groups can be protonated at low pH to yield a polymer which will be positively charged. A sample was titrated to determine the pKa of the polymer. This was determined by starting at high pH (e.g. 8) and titrating with HCl to low pH and then back again. Multiple pKa values were obtained. This would be expected due to the multiple arrangements of the amine oxide groups in the copolymer. The data was analyzed and it was found that at a pH of 4 close to 100% of the amine oxide groups are protonated. The amine equivalent weight also was calculated and found to be approximately 330 g polymer/equivalent amine. Despite the fact that this polymer would be highly charged it is surprising compatible with moderate levels (less than 2%) of many anionic surfactants. The level of surfactant was not increased too far to ensure the formulations had adequate substantivity on skin.

The anionic detergent type surfactants used in these examples are described in Table 18a. The compositions, pH, stability, and substantivity for these examples are listed in Tables 18b and 18c. In Tables 18b and 18c the amounts of all components are given on a solids basis. By this it is meant that if a particular component is added as a solution in water the water is not included in the quantity of this component but rather reflected in the total amount of water in the composition.

TABLE 18a

Detergent type surfactants used in Examples 100–109

| Trade Mark Name | Chemical Description | CAS Number | Source | Address |
|---|---|---|---|---|
| ALPHASTEP PC-48 | Sodium methyl-2-sulfoC12–16 ester and disodium2-sulfo C12–16 fatty acid | 149458-07-1 | Stepan | Northfield, IL |
| MACKAM 50-SB | Cocoamidopropylhydroxy sultaine | 68139-30-0 | McIntyre Group Ltd | University Park, IL |
| AMMONYX LMDO | C12–14 amidopropyldimethylamine oxide | Confidential | Stepan | Northfield, IL |
| AMMONYX LO | lauryldimethylamine oxide | 1643-20-5 | Stepan | Northfield, IL |
| POLYSTEP A16 | sodium dodecylbenzenesulfonate | 68608-89-9 | Stepan | Northfield, IL |
| POLYSTEP B11 | Ammonium lauryl ether sulphate (4 moles ethyleneoxide) | | Stepan | Northfield, IL |
| WITCONATE 60T | C10–C13 alkylbenzenesulfonic acid, Triethanolamine salt | 68411-31-4 | Crompton Corp | Greenwich CT |
| STEPANOL WAT | TEA laurylsulfate | 139-96-8 | Stepan | Northfield, IL |

TABLE 18a-continued

Detergent type surfactants used in Examples 100–109

| Trade Mark Name | Chemical Description | CAS Number | Source | Address |
|---|---|---|---|---|
| STEPANMILD SL3 | disodium laureth (3 mole) sulfosuccinate | 39354-45-5 | Stepan | Northfield, IL |
| STEOL CS330 | Ammonium laureth sulfate | | Stepan | Northfield, IL |
| HOSTAPHAT KL 340D | Mono, di and tri-lauryltetraglcyolether-o-phosphoric acid esters | mixture | Clariant | Charlotte, NC |
| ISOFOL 12 SULFATE | 2butyloctylsulfate, sodium salt | 94200-74-5 | Condea Vista | Houston TX |
| ISOFOL 16 SULFATE | 2hexyldecyl sulfate sodium salt | 25542-86-3 | Condea Vista | Houston TX |
| MASKAM JS | Sodium caprylamphohydroxysulfonate | 68610-39-9 | McIntyre | University Park, IL |
| CRODAFOS SG | PPG-5-Ceteth 10 phosphate | 73361-29-2 | Croda, Inc | Parsippany, NJ |
| RHODAPEX CO-436 | Ammonium nonylphenol ether sulfate, branched | 68649-55-8 | Rhodia | Dayton, NJ |
| HOSTAPON CT | sodium methylcocoyltaurate | 61791-42-2 | Clariant | Charlotte, NC |
| HOSTAPUR SAS-60 | sodium C14–17 sec alkylsulfonate | 85711-69-9 | Clariant | Charlotte, NC |
| HOSTAPON SCI 85 | Sodium cocoylisethionate (85% actives) | 61789-32-0 | Clariant | Charlotte, NC |

TABLE 18b

Compositions, pH, Stability, and Substantivity for Examples 100–107

| Component | 100 wt-% | 101 wt-% | 102 wt-% | 103 wt-% | 104 wt-% | 105 wt-% | 106 wt-% | 107 wt-% |
|---|---|---|---|---|---|---|---|---|
| DIAFORMER Z-731 | 5.00 | 5.00 | 5.00 | 5.00 | 5.00 | 5.00 | 5.00 | 5.00 |
| Povidone-Iodine USP | 7.50 | 7.50 | 7.50 | 7.50 | 7.50 | 7.50 | 7.50 | 7.50 |
| Lactic Acid | 6.50 | 5.00 | 5.00 | 5.00 | 5.00 | 5.00 | 5.00 | 5.00 |
| Malic Acid | 2.50 | 2.00 | 2.00 | 2.00 | 2.00 | 2.00 | 2.00 | 2.00 |
| NIKKOL TL10 | 1.50 | 0.00 | 0.00 | 0.00 | 0.00 | 0.00 | 1.50 | 0.00 |
| BRIJ 700 | 2.00 | 1.00 | 1.00 | 1.00 | 0.00 | 0.00 | 2.00 | 1.00 |
| ALPHASTEP PC-48 | 1.00 | 0.00 | 0.00 | 0.00 | 0.00 | 0.00 | 0.00 | 0.00 |
| MACKAM 50-SB | 0.00 | 1.00 | 0.00 | 0.00 | 0.00 | 0.00 | 0.00 | 0.00 |
| CRODAPHOS SG | 0.00 | 0.00 | 0.00 | 1.00 | 0.00 | 0.00 | 0.00 | 0.00 |
| AMMONYX LMDO (30%) | 0.00 | 0.00 | 0.00 | 1.00 | 1.00 | 1.00 | 1.00 | 1.00 |
| STEPANMILD SL3 | 0.00 | 0.00 | 0.67 | 0.00 | 0.00 | 0.00 | 0.00 | 0.00 |
| POLYSTEP A16 | 0.00 | 0.00 | 0.00 | 0.00 | 0.00 | 1.00 | 0.00 | 0.00 |
| WITCONATE 60T | 0.00 | 0.00 | 0.00 | 0.00 | 0.57 | 0.00 | 0.00 | 0.00 |
| STEPANOL WAT | 0.00 | 0.00 | 0.00 | 0.00 | 0.00 | 0.00 | 1.00 | 0.00 |
| RHODAPEX CO-436 | 0.00 | 0.00 | 0.00 | 0.00 | 0.00 | 0.00 | 0.00 | 1.16 |
| Water | 74.00 | 78.50 | 78.83 | 77.5 | 78.93 | 78.5 | 75 | 77.34 |
| pH | 3.5–4 | 3.5–4 | 3.5–4 | 3.5–4 | 3.5–4 | 3.5–4 | 3.5–4 | 3.5–4 |
| Stability at 23° C. after 4 days | transparent/dark | transparent/dark | transparent/dark | transparent/dark | transparen/dark | transparent/dark | transparent/dark | transparent/dark |
| Stability at 60° C. after 4 days | transparent/dark | transparent/dark | transparent/dark/ | transparent/dark | transparent/dark | transparent/dark | transparent/dark | transparent/dark |
| Substantivity (sec) | >>60 | >>60 | 50–60 | 50 | 60 | >60 | >60 | 40 |

TABLE 18c

Compositions, pH, Stability, and Substantivity for Examples 108–109

| Component | 108 wt-% | 109 wt-% |
|---|---|---|
| DIAFORMER Z-731 | 5.00 | 5.00 |
| Povidone-Iodine USP | 7.50 | 7.50 |
| Lactic Acid | 5.00 | 5.00 |
| Malic Acid | 5.00 | 2.00 |
| NIKKOL TL10 | 1.50 | 0.00 |
| BRIJ 700 | 0.00 | 1.00 |
| CRODAPHOS SG | 1.00 | 0.00 |
| MACKAM JS | 0.00 | 1.00 |
| Water | 75.00 | 78.50 |
| pH | 3.5–4 | 3.5–4 |
| Stability at 23° C. after 4 days | transparent/dark | transparent/dark |
| Stability at 60° C. after 4 days | transparent/dark | transparent/dark |
| Substantivity (sec) | >60 | >>60 |

The data indicates that the amine oxide side-chain functional substantive polymer, DIAFORMER Z731, is surprisingly compatible with a wide variety of anionic surfactants. The presence of a co-surfactant such as an amine oxide (AMMONYX LMDO) appears to help stability as it did for the quaternary polymers as well. Despite the addition of these detergent type surfactants, which are widely used in shampoos, soaps and other cleaners to facilitate removal of dirt, oil, etc. the substantivity to skin was excellent.

Examples 110–115

Examples 110–115 illustrate the use of high levels of an organic acid buffer in combination with an amine oxide side-chain functional substantive film-forming polymer. The polymer used in Examples 110–112 was a commercially available poly(amine oxide acrylate) available as DIAFORMER Z-731 (Clariant Corp.). The polymer used in Examples 113–115 was prepared as outlined above for Preparation of Polymer C (LMA). The polymer included SMA (10%)/IBMA (25%)/DMAEMA (55%)/MMA(10%). The monomers were polymerized at a temperature of 65° C. using 0.3% by weight VAZO 67. The DMAEMA was oxidized to the amine oxide using a molar ratio of DMAEMA to hydrogen peroxide used was 0.9. Residual monomer was scavenged with vitamin C in place of SFS. After distillation the residual level of hydrogen peroxide was measured and found to be less than 100 ppm. The polymer had an inherent viscosity of 0.7. The compositions were prepared according to the General Composition Preparation using the components listed in Table 23.

Compositions were evaluated for human skin antimicrobial activity on human volunteers as described in the test protocol using the 30 second scrub application technique. Compositions were also evaluated for substantivity, drape adhesion, and tack as outlined in the test protocols. The results are shown in Table 23.

TABLE 23

Compositions and Results of the Antimicrobial Activity, Substantivity, and Tack for Examples 110–115

| Component (Amount in wt-% solids) | 110 | 111 | 112 | 113 | 114 | 115 |
| --- | --- | --- | --- | --- | --- | --- |
| 5/10/40/45 SMA/iBMA/DMAEMA oxide/MMA | 0.00 | 0.00 | 0.00 | 5.00 | 5.00 | 5.00 |
| DIAFORMER Z-731 | 5.00 | 5.00 | 5.00 | 0.00 | 0.00 | 0.00 |
| PVP-I | 7.50 | 7.50 | 7.50 | 0.00 | 7.50 | 0.00 |
| Lactic Acid | 5.00 | 5.00 | 5.00 | 5.00 | 5.00 | 5.00 |
| Malic Acid | 2.00 | 2.00 | 2.00 | 2.00 | 2.00 | 2.00 |
| BRIJ 700 | 1.00 | 1.00 | 1.00 | 1.00 | 1.00 | 1.00 |
| Mackam 50-SB | 1.00 | 0.00 | 0.00 | 1.00 | 0.00 | 0.00 |
| Crodaphos SG | 0.00 | 0.00 | 1.00 | 0.00 | 0.00 | 1.00 |
| Stepanmild SL3 | 0.00 | 0.67 | 0.00 | 0.00 | 0.67 | 0.00 |
| Ammnoyx LMDO | 0.00 | 0.00 | 1.00 | 0.00 | 0.00 | 1.00 |
| Water | 78.5 | 78.83 | 77.50 | 78.5 | 78.83 | 77.50 |
| pH | 3.5–4 | 3.5–4 | 3.5–4 | 3.5–4 | 3.5–4 | 3.5–4 |
| Microbial kill (log reduction) | 1.9 | 2.6 | 2.5 | | | |
| BETADINIE kill (log reduction) | 1.7 | 1.7 | 1.7 | | | |
| Drape Adhesion | Good | Good | Good | | | |
| Substantivity (sec) | >60 | 50–60 | 50 | >60 | >60 | 30 |
| Tack | Very low | Very low | Very low | Very low | Very low | Very low |

The results indicate that Examples 110–112 had very good antimicrobial activity. Examples 110, 113, and 114 had exceptional substantivity. The substantivity of Examples 111, 112, and 115 was far greater than that of BETADINE which typically lasts less than 10 seconds. The tack of all samples was very low. The adhesion of IOBAN 2 Incise drape (Drape Adhesion) was good for Examples 110–112 and judge equivalent to that over dry Betadine Solution. All samples were transparent and dark (stable) at room temperature.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A film-forming composition comprising:
   a water-soluble or water-dispersible vinyl polymer comprising amine group-containing side-chains and at least two a-copolymerized hydrophobic monoethylenically unsaturated alkyl (meth)acrylic monomers; wherein one of the hydrophobic monomers includes an alkyl group of 1 to 4 carbon atoms and one of the hydrophobic monomers includes an alkyl group of 6 to 22 carbon atoms; wherein the amine equivalent weight of the polymer is at least about 300 grams polymer per equivalent of amine group;
   water; and
   a surfactant;
   wherein
   a dry film of the composition is substantive.

2. The composition of claim 1 further comprising an active agent.

3. The composition of claim 2 wherein the active agent comprises an antimicrobial agent, a pharmaceutical, or a cosmetic agent.

4. The composition of claim 3 wherein the active agent comprises an iodophor, iodine, chlorhexidine, chlorhexidine salts, fatty acid monoesters of glycerin and propylene glycol, chlorinated phenols, triclosan, octenidine, or mixtures thereof.

5. The composition of claim 4 wherein the active agent is iodine or an iodophor.

6. The composition of claim 2 wherein the ratio of vinyl polymer to active agent is about 0.25:1 to about 5:1.

7. The composition of claim 1 wherein the amine equivalent weight of the polymer is no greater than about 3000 grams polymer per equivalent of amine group.

8. The composition of claim 1 wherein the surfactant is a nonionic surfactant.

9. The composition of claim 8 wherein the nonionic surfactant has an HLB of at least about 14.

10. The composition of claim 9 wherein the nonionic surfactant has an HLB or no greater than about 19.

11. The composition of claim 10 further comprising a surfactant having an HLB of less than about 14 or greater than about 19.

12. The composition of claim 8 further comprising an anionic or amphoteric surfactant.

13. The composition of claim 12 where the anionic or amphoteric surfactant is selected from the group consisting of sulfates, sulfonates, phosphates, phosphonates, ammonium sulfonate amphoterics, and mixtures thereof.

14. The composition of claim 1 wherein the surfactant is an amine oxide surfactant.

15. The composition of claim 1 wherein the surfactant is an anionic surfactant.

16. The composition of claim 1 further comprising a hydroxycarboxylic acid buffer.

17. The composition of claim 16 wherein the hydroxycarboxylic acid buffer comprises an alpha-hydroxycarboxylic acid.

18. The composition of claim 17 wherein the hydroxycarboxylic acid buffer comprises lactic acid, malic acid, citric acid, or a mixture thereof.

19. The composition of claim 1 wherein the composition has a Brookfield viscosity of no greater than about 1000 cps.

20. The composition of claim 1 wherein the vinyl polymer has a glass transition temperature of at least about 30° C.

21. The composition of claim 20 wherein the vinyl polymer has a glass transition temperature of at least about 50° C.

22. The composition of claim 1 further comprising a polymer having a higher Tg than that of the vinyl polymer having amine groups.

23. The composition of claim 22 wherein the polymer having a higher Tg than that of the vinyl polymer having amine groups is polyvinyl alcohol.

24. The composition of claim 1 wherein the composition is stable.

25. The composition of claim 1 having a flashpoint of greater than about 60° C. measured according to test method ASTM D3278-96.

26. The composition of claim 1 wherein the amine groups are selected from the group consisting of quaternary ammonium groups, protonated tertiary amine groups, amine oxide groups, and combinations thereof.

27. The composition of claim 1 having a dry time of no greater than about 2 minutes.

28. The composition of claim 1 wherein the surfactant is a silicone copolyol surfactant.

29. The composition of claim 1 wherein a dry film of the composition is substantially nontacky.

30. The composition of claim 1 further comprising a (C1–C4)alcohol.

31. A film-forming composition comprising:
    a water-soluble or water-dispersible vinyl polymer comprising amine group-containing side-chains and a copolymerized hydrophobic monomer; wherein the amine equivalent weight of the polymer is about 300 grams to about 3000 grams polymer per equivalent of amine group;
    an active agent present is an amount of at least about 0.25% by weight of the total composition;
    water; and
    a surfactant;
    wherein
        the composition is substantially free of volatile organic solvents.

32. The composition of claim 31 wherein the active agent is an antimicrobial agent.

33. The composition of claim 31 wherein the composition possesses two or more of the following characteristics:
    the polymer is present in an amount greater than the surfactant;
    the polymer to active agent weight ratio is at least about 0.25:1; or
    a dry film of the composition is substantive.

34. The composition of claim 33 wherein the composition possesses all of the following characteristics:
    the polymer is present in an amount greater than the surfactant;
    the polymer to active agent weight ratio is at least about 0.25:1; and
    a dry film of the composition is substantive.

35. The composition of claim 31 wherein the vinyl polymer comprises dimethylamine oxide methacrylate, isobutyl methacrylate, methyl methacrylate, and a (C12–18) alkyl methacrylate.

36. The compositions of claim 31 wherein the vinyl polymer comprises trimethylaminioethyl acrylate chloride, butyl acrylate, methyl methacrylate, and a (C12–18)alkyl methacrylate.

37. A film-forming composition comprising:
    a water-soluble or water-dispersible vinyl polymer prepared from monomers comprising:
        an amine group-containing monomer;
        about 1 wt-% to about 30 wt-% of a (C6–C22)alkyl (meth)acrylic monomer; and
        about 15 wt-% to about 75 wt-% of a (C1–C4)alkyl (meth)acrylic monomer;
            wherein the amine equivalent weight of the polymer is about 300 to about 3000 grams polymer per equivalent of amine group;
        a surfactant;
        water; and
        an active agent;
        wherein a dry film of the composition is substantive.

38. The composition of claim 37 wherein the active agent comprises an antimicrobial agent, a pharmaceutical, or a cosmetic agent.

39. The composition of claim 37 wherein the active agent comprises an iodophor, iodine, chlorhexidine, chlorhexidine salts, fatty acid monoesters of glycerin and propylene glycol, chlorinated phenols, triclosan, octenidine, or mixtures thereof.

40. The composition of claim 39 wherein the active agent is iodine or an iodophor.

41. The composition of claim 37 wherein the amine equivalent weight of the polymer is no greater than about 1500 grams polymer per equivalent of amine group.

42. The composition of claim 37 further comprising a surfactant.

43. The composition of claim 42 wherein the surfactant is a nonionic, anionic, or amphoteric surfactant.

44. The composition of claim 43 where the anionic or amphoteric surfactant is selected from the group consisting of sulfates, sulfonates, phosphates, phosphonates, ammonium sulfonate amphoterics, and mixtures thereof.

45. The composition of claim 37 wherein the surfactant is an amine oxide surfactant.

46. The composition of claim 37 wherein the surfactant is an anionic surfactant.

47. The composition of claim 37 further comprising a hydroxycarboxylic acid buffer.

48. The composition of claim 37 wherein the composition is stable.

49. The composition of claim 37 wherein the amine groups are selected from the group consisting of quaternary ammonium groups, protonated tertiary amine groups, amine oxide groups, and combinations thereof.

50. The composition of claim 31 wherein the active agent is iodine or an iodophor.

51. The composition of claim 50 wherein the active agent is povidone iodine.

52. A film-forming composition comprising:
    a water-soluble or water-dispersible vinyl polymer comprising amine group-containing side-chains and a copolymerized hydrophobic monomer;

wherein the amine equivalent weight of the polymer is at least about 300 grams polymer per equivalent of amine group;

water;

a surfactant; and a buffer.

53. The composition of claim 52 which has a pH of about 2 to about 6.

54. The composition of claim 53 which has a pH of about 3 to about 5.

55. The composition of claim 52 further comprising an active agent.

56. The composition of claim 55 wherein the active agent is an antimicrobial agent.

57. The composition of claim 56 wherein the antimicrobial agent is an iodophore.

58. The composition of claim 57 wherein the iodophore is povidone iodine.

59. The composition of claim 52 wherein the buffer is a hydroxycarboxylic acid.

60. A film-forming composition comprising:

a water-soluble or water-dispersible vinyl polymer comprising amine group-containing side-chains and a copolymerized hydrophobic monomer;

wherein the amine equivalent weight of the polymer is at least about 300 grams polymer per equivalent of amine group;

water; and a surfactant present in an amount of no greater than about 10% by weight based on the total weight of the composition;

wherein a medical adhesive product adheres to a dry film of the composition on skin.

61. The composition of claim 60 wherein the surfactant is present in an amount of no greater than about 7% by weight based on the total weight of the composition.

62. The composition of claim 61 wherein the surfactant is present in an amount of no greeter than about 5% by weight based on the total weight of the composition.

63. A dry film on skin formed from a film-forming composition comprising;

a water-soluble or water-dispersible vinyl polymer comprising amine group-containing side-chains and a copolymerized hydrophobic monomer;

wherein the amine equivalent weight of the polymer is at least about 300 grams polymer per equivalent of amine group;

a surfactant.

64. A film-forming composition comprising;

a water-soluble or water-dispersible vinyl polymer comprising amine group-containing side-chains and a copolymerized hydrophobic monomer;

wherein the amine equivalent weight of the polymer is at least about 300 grams polymer per equivalent of amine group;

water; and a surfactant;

wherein a dry film of the composition on skin can be removed with water soaked gauze.

65. A film-forming composition comprising:

a water-soluble or water-dispersible vinyl polymer comprising amine group-containing side-chains and a copolymerized hydrophobic monomer; wherein the amine equivalent weight of the polymer is at least about 300 grams polymer per equivalent of amine group;

water; and a surfactant selected from the group consisting of alkyl polyglucosides, ammonium sulfonate amphoterics, alkyl phosphates, alkylether phosphates, aralkylphosphates, and aralkylether phosphates.

66. The composition of claim 1 wherein the surfactant is an amphoteric surfactant.

67. The composition of claim 1 wherein the polymer is present in an amount greater than the surfactant.

68. The composition of claim 67 wherein the composition includes an active agent and the polymer to active agent weight ratio is at least about 0.25:1.

69. The composition of claim 31 wherein the composition possesses at least one of the following characteristics:

the polymer is present in amount greater than the surfactant; or a dry film of the composition is substantive.

* * * * *

UNITED STATES PATENT AND TRADEMARK OFFICE
CERTIFICATE OF CORRECTION

PATENT NO. : 6,838,078 B2
APPLICATION NO. : 10/052158
DATED : January 4, 2005
INVENTOR(S) : Danli Wang It is certified that error appears in the above-identified patent and that said Letters Patent is hereby corrected as shown below:

Title Page
Item [56], References Cited, OTHER PUBLICATIONS, delete "CELV0L" and insert -- CELVOL --, therefore.

Column 4
Line 46, delete "milliggrams" and insert -- milligrams --, therefore.

Column 9
Line 33, delete "polymer," and insert -- polymer. --, therefore.

Column 11
Line 46, delete "previsouly" and insert -- previously --, therefore.

Column 12
Line 44, delete "certan" and insert -- certain --, therefore.
Line 44, delete "quatemary" and insert -- quaternary --, therefore.

Column 14
Line 59, delete "lodophors" and insert -- Iodophors --, therefore.
Line 63, delete "lodophors" and insert -- Iodophors --, therefore.
Line 65, delete "lactanis" and insert -- lactams --, therefore.

Column 15
Line 20, delete "moncaprate" and insert -- monocaprate --, therefore.

Column 16
Line 6, delete "ran" and insert -- run --, therefore.

Column 17
Line 2, delete "BRU" and insert -- BJIJ --, therefore.

Column 19
Line 58-62, delete "Optionally, the ........aklylamidopropyl group." and insert the same in Col. 19, Line 57 after "different.".

Column 22
Line 7, delete "hydroxycarboxyiic" and insert -- hydroxycarboxylic --, therefore.

Column 28
Line 48, delete "30x7.8" and insert -- 30X7.8 --, therefore

UNITED STATES PATENT AND TRADEMARK OFFICE
CERTIFICATE OF CORRECTION

PATENT NO. : 6,838,078 B2
APPLICATION NO. : 10/052158
DATED : January 4, 2005
INVENTOR(S) : Danli Wang It is certified that error appears in the above-identified patent and that said Letters Patent is hereby corrected as shown below:

Column 29
Line 52, delete "neturalization" and insert -- neutralization --, therefore.

Column 31
Line 34, delete "fluorscein" and insert -- fluoroscein --, therefore.

Column 42
Line 41, delete "Povidone-Iodine" and insert -- Povidone-lodine --, therefore.
Line 66, delete "DMAEMA.C1" and insert -- DMAEMA.CI --, therefore.

Column 43
Col. 1, Row 1, Table 8, delete "Cl/AM90G" and insert -- CI/AM90G --, therefore.

Column 44
Line 11, delete "DMAEME.C1" and insert -- DMAEME.CI --, therefore.

Column 43/44
Col. 1, Row 2, Table 9, delete "DMAEMA.C1" and insert -- DMAEMA.CI --, therefore.
Col. 1, Row 3, Table 9, delete "DMAEMA.C1" and insert -- DMAEMA.CI --, therefore.

Column 45
Col. 1, Row 1, Table 10, delete "DMAEMA.Cl" and insert -- DMAEMA.CI --, therefore.

Column 52
Line 61, delete "Siaphylococcus" and insert -- "Staphylococcus --, therefore.

Column 61/62
Col. 6, Row 18, Table 18b, delete "transparen/dark" and insert -- transparent/dark --, therefore.

Column 63
Col. 1, Row 14, Table 23, delete "BETADINIE" and insert -- BETADINE --, therefore.

Column 64
Line 23, delete "a-copolymerized" and insert -- copolymerized --, therefore.

UNITED STATES PATENT AND TRADEMARK OFFICE
CERTIFICATE OF CORRECTION

PATENT NO. : 6,838,078 B2
APPLICATION NO. : 10/052158
DATED : January 4, 2005
INVENTOR(S) : Danli Wang It is certified that error appears in the above-identified patent and that said Letters Patent is hereby corrected as shown below:

<u>Column 65</u>
Line 49, delete "is" and insert -- in --, therefore.

<u>Column 67</u>
Line 39, delete "greeter" and insert -- greater --, therefore.

<u>Column 68</u>
Line 19, delete "comprising:" and insert -- comprising; --, therefore.
Line 41, after "in" insert -- an --.

Signed and Sealed this

Thirteenth Day of November, 2007

JON W. DUDAS
*Director of the United States Patent and Trademark Office*